(12) United States Patent
Hugot et al.

(10) Patent No.: US 7,592,437 B2
(45) Date of Patent: Sep. 22, 2009

(54) GENES INVOLVED IN INTESTINAL INFLAMMATORY DISEASES AND USE THEREOF

(75) Inventors: Jean Pierre Hugot, Paris (FR); Gilles Thomas, Paris (FR); Mohamed Zouali, Bagneux (FR); Suzanne Lesage, Sainte-Honorine (FR); Mathias Chamaillard, Joue-les-Tours (FR)

(73) Assignee: Fondation Jean Dausset-CEPH, Paris (FR)

( * ) Notice: Subject to any disclaimer, the term of this patent is extended or adjusted under 35 U.S.C. 154(b) by 734 days.

(21) Appl. No.: 10/240,046

(22) PCT Filed: Mar. 27, 2001

(86) PCT No.: PCT/FR01/00935

§ 371 (c)(1),
(2), (4) Date: Jan. 15, 2003

(87) PCT Pub. No.: WO01/72822

PCT Pub. Date: Oct. 4, 2001

(65) Prior Publication Data

US 2003/0190639 A1    Oct. 9, 2003

(30) Foreign Application Priority Data

Mar. 27, 2000 (FR) .................................. 00 03832

(51) Int. Cl.
*C07H 21/04* (2006.01)
*C12N 1/19* (2006.01)
*C12N 1/21* (2006.01)
*C12N 16/63* (2006.01)
*C12N 5/10* (2006.01)

(52) U.S. Cl. ...................... 536/23.5; 536/23.1; 530/350; 435/69.1; 435/252.3; 435/320.1; 435/7.16; 435/7.1

(58) Field of Classification Search ........................ None
See application file for complete search history.

(56) References Cited

U.S. PATENT DOCUMENTS 6,812,339 B1 * 11/2004 Venter et al. ............. 536/24.31
6,835,815 B2   12/2004 Nunez et al.
6,858,391 B2    2/2005 Nunez et al.

FOREIGN PATENT DOCUMENTS

| EP | 1 074 617 A | 2/2001 |
| WO | WO 99 23255 A | 5/1999 |
| WO | WO 99 40102 A | 8/1999 |
| WO | WO 99 64576 A | 12/1999 |
| WO | WO 00 58473 A | 10/2002 |

OTHER PUBLICATIONS

Ogura et al., J. Biol. Chemistry, vol. 276, (70): 4812-4818, Feb. 16, 2001.*
Phillips, A., J Pharm Pharmacology 53: 1169-1174, 2001.*
Campbell et al. Theriology 47(1): 63-72, 1997.*
Wigley et al. Reprod fert. Dev. 6: 585-588, 1994.*
,Kaufman et al., Blood 94: 3178-3184, 1999.*
Wang et al., Nuc. Acids Res. 27: 4609-4618, 1999.*
Check Nature 422:7, 2003.*
Touchette, Nat. Med. 2(1) 7-8, 1996.*
Verma et al Nature 389:239-242, 1997.*
Rosenberg et al, Science 287:1751, 2000.*
Juengst BMJ, 326:1410-11, 2003.*
Couzin et al, Science 307:1028, 2005.*
Anderson et al., Nature, 392 :25-30, Supp, Apr. 30, 1998.*
Goncalves, Bioassays. 27(5):506-517, 2005.*
Bowie et al (Science, Mar. 16, 1990, vol. 247, pp. 1307-1310).*
Suggs et al. PNAS, 1981, vol. 78, pp. 6613-6617.*
Database EMBL Accession No. AC007728, Jun. 7, 1999, DOE Joint Genome Institute: "*Homo sapiens* chromosome 16 clone, RP11-327F22, Working Draft Sequence, 1 ordered pieces.", XP002156657.
Database EMBL Accession No. AC007608, May 21, 1999, DOE Joint Genome Institute, "*Homo sapiens* chromosome 16 clone RP11-401P9, Working Draft Sequence, 8 ordered pieces.", XP002156658.
Database EMBL Accession No. AQ534686, May 18, 1999, Zhao, S., et al.,: "RPCI-11-384F21.TJ RPCI-11 *Homo sapiens* genomic clone RPCI-11-384F21, genomic survey sequence.", XP002156659.
Database EMBL Accession No. AI681116, May 27, 1999, NCI-CGAP: "tx44b02.x1 NCI_CGAP_Lu24 *Homo sapiens* cDNA clone Image:2272395 3', mRNA sequence.", XP002156660.
Database EMBL Accession No. AQ585409, Jun. 9, 1999, Zhao, S., et al.: "RPCI-11-459C5.TV RPCI-11 *Homo sapiens* genomic clone RPCI-11-459C5, genomic survey sequence.", XP002156661.
Database EMBL Accession No. AI090427, Aug. 19, 1998, NCI-CGAP: "oy82d10.s1 NCI_CGAP_CLL1 *Homo sapiens* cDNA clone Image:1672339 3', mRNA sequence.", XP002156662.
Database EMBL Accession No. AQ176547, Sep. 21, 1998, Mahairas, G.G., et al., "HS_3213_B1_CO5_T7 CIT Approved Human Genomic Sperm Library D *Homo sapiens* genomic clone Plate=3213 Col=9 Row=F, genomic survey sequence.", XP002156663.
Database EMBL Accession No. AF178930, Nov. 23, 2000, Ogura, Y. et al.: "*Homo sapiens* NOD2 protein (NOD2) mRNA, complete cds.", XP002177310; Ogura, Y. et al., "Nod2, a Nod1/Apaf-1 Family Member that is Restricted to Monocytes and Activates NF-kappa B", The Journal of Biological Chemistry, vol. 276, No. 7, Feb. 16, 2001, pp. 4812-4818.
Hugot, Jean-Pierre et al., "Association of NOD2 leucine-rich repeat variants with susceptibility to Crohn's disease", Nature (London), vol. 411, No. 6837, 2001, pp. 599-603, XP002177308, ISSN: 0028-0836.

(Continued)

*Primary Examiner*—Gary B Nickol
*Assistant Examiner*—Nirmal S Basi
(74) *Attorney, Agent, or Firm*—Townsend and Townsend and Crew LLP

(57) ABSTRACT

The invention concerns genes involved in inflammatory and/or immune diseases and some cancers, in particular intestinal cryptogenic inflammatory diseases, and proteins coded by said genes. The invention also concerns methods for diagnosing inflammatory diseases.

18 Claims, 4 Drawing Sheets

OTHER PUBLICATIONS

Database EMBL Accession No. AW082334, Oct. 18, 1999, NCI-CGAP: "xb65f03.x1 Soares_NFL_T_GBC_S1 *Homo sapiens* cDNA clone Image:2581181 3' similar to contains LTR1.t3 LTR1 repetitive element;, mRNA sequence.", XP002156664.

Database EMBL Accession No. AA282390, Apr. 4, 1997, NCI-CGAP: "zs89a11.r1 NCI_CGAP_GCB1 *Homo sapiens* cDNA clone Image: 704636 5', mRNA sequence.", XP002156665.

Database EMBL Accession No. AA278249, Apr. 3, 1997, NCI-CGAP: "zs77c05.r1 NCI_CGAP_GCB1 *Homo sapiens* cDNA clone Image: 703496 5', mRNA sequence.", XP002156666.

Database EMBL Accession No. AW134842, Oct. 29, 1999, NCI-CGAP: "UI-H-BI1-abs-e-09-0-UI.s1, NCI_CGAP_Sub3 *Homo sapiens* cDNA clone Image:2713048 3', mRNA sequence.", XP002156667.

Database EMBL Accession No. AW104269 Oct. 21, 1999, NCI-CGAP: "xd70h07.x1 Soares_NFL_T_GBC_S1 *Homo sapiens* cDNA clone Image:2603005 3' similar to contains Alu repetitive element; contains element MER22 repetitive element;, mRNA sequence", XP002156668.

Database EMBL Accession No. AI377313, Jan. 28, 1999, NCI-CGAP: "te60b02.x1 Soares_NFL_T_GBC_S1 *Homo sapiens* cDNA clone Image:2091051 3' similar to contains element MSR1 MSR1 repetitive element;, mRNA sequence.", XP002156669.

Hugot, Jean-Pierre et al., "Mapping of a susceptibility locus for Crohn's disease on chromosome 16.", Nature (London), vol. 379, No. 6568, 1996, pp. 821-823, XP002156655, ISSN: 0028-0836.

Mirza Muddassar M. et al., "Evidence of linkage of the inflammatory bowel disease susceptibility locus on chromosome 16 (IBD1) to ulcerative colitis", Journal of Medical Genetics, vol. 35, No. 3, Mar. 1998, pp. 218-221, XP000971943, ISSN: 0022-2593.

Hugot, J.P. et al., "Fine mapping of the inflammatory bowel disease susceptibility locus 1 (IBD1) in the pericentromeric region of chromosome 16.", Gastroenterology, vol. 114, No. 4, Part 2, Apr. 15, 1998, p. A999, XP000971941, Digestive Diseases Week and the 99th Annual Meeting of the American Gastroenterological Association; New Orleans, Louisiana, USA; May 16-22, 1998; ISSN: 0016-5085.

Database Swissprot Accession No. Q9Y239, Inohara, N. et al., "NOD1 protein", XP002156670; Inohara, N. et al., "Nod 1, an Apaf-1-like activator of caspase-9 and nuclear factor-kappaB", The Journal of Biological Chemistry, vol. 274, No. 21, May 21, 1999, pp. 14560-14567, XP002156656.

\* cited by examiner

GENES INVOLVED IN INTESTINAL INFLAMMATORY DISEASES AND USE THEREOF

The present invention relates to genes involved in inflammatory and/or immune diseases and certain cancers, in particularly cryptogenetic inflammatory bowel diseases, and also to the proteins encoded by these genes. The present invention also relates to methods for diagnosing inflammatory diseases.

Cryptogenetic inflammatory bowel diseases (IBDs) are diseases characterized by an inflammation of the digestive tract, the cause of which is unknown. Depending on the location and the characteristics of the inflammation, two different nosological entities are distinguished: ulcerative colitis (UC) and Crohn's disease (CD). UC was described by S Wilkes in 1865, whereas the first case of regional ileitis was reported by Crohn in 1932. In reality, it is possible that these two diseases go back much further.

IBDs are chronic diseases which evolve throughout life and which affect approximately 1 to 2 individuals per 1 000 inhabitants in western countries, which represents between 60 000 and 100 000 individuals suffering from these diseases in France. They are diseases which appear in young individuals (peak instance is in the third decade), progressing via attacks interspersed with remissions, with frequent complications such as undernutrition, retarded growth in children, bone demineralization and, in the end, malignant degeneration to colon cancer. No specific treatment exists. Conventional therapeutics make use of anti-inflammatories, of immunosuppressors and of surgery. All these therapeutic means are, themselves, a source of considerable iatrogenic morbidity. For all these reasons, IBDs appear to be a considerable public health problem.

The etiology of IBDs is currently unknown. Environmental factors are involved in the occurrence of the disease, as witnessed by the secular increase in incidence of the disease and the incomplete concordance in monozygous twins. The only environmental risk factors currently known are 1) tobacco, the role of which is harmful in CD and beneficial in UC, and 2) appendectomy which has a protective role for UC.

Genetic predisposition has been suspected for a long time due to the existence of ethnic and familial aggregation of these diseases. In fact, IBDs are more common in the Caucasian population, and in particular in the Jewish population of central Europe. Familial forms represent from 6 to 20% of IBD cases. They are particularly common when the disease begins early. However, it is studies in twins which have made it possible to confirm the genetic nature of these diseases. In fact, the concordance rate between twins for these diseases is greater in monozygous twins than in dizygous twins, which pleads strongly in favor of a hereditary component to IBDs, in particular to CD. In all probability, IBDs are complex genetic diseases involving several different genes, interacting with one another and with environmental factors. IBDs can therefore be classified within the context of multifactor diseases.

Two major strategies have been developed in order to demonstrate the IBD-susceptibility genes. The first is based on the analysis of genes which are candidates for physiopathological reasons. Thus, many genes have been proposed as potentially important for IBDs. They are often genes which have a role in inflammation and the immune response. Mention may be made of the HLA, TAP, TNF and MICA genes, lymphocyte T receptor, ICAM1, interleukin 1, CCR5, etc. Other genes participate in diverse functions, such as GAI2, motilin, MRAMP, HMLH1, etc. In reality, none of the various candidate genes studied has currently definitively proved itself to have a role in the occurrence of IBDs.

The recent development of human genome maps using highly polymorphic genetic markers has enabled geneticists to develop a nontargeted approach over the entire genome. This approach, also called reverse genetics or positional cloning, makes no hypothesis regarding the genes involved in the disease and attempts to discover them through systematic screening of the genome. The method most used for complex genetic diseases is based on studying identity by decendance of the affected individuals of the same family. This value is calculated for a large number (300-400) of polymorphism markers distributed evenly (every 10 cM) over the genome. In the case of excess identity between affected individuals, the marker(s) tested indicate(s) a region supposed to contain a gene for susceptibility to the disease. In the case of complex genetic diseases, since the model underlying the genetic predisposition (number of genes and relative importance of each of them) is unknown, the statistical methods to be used will have to be adjusted.

The present invention relates to the demonstration of the nucleic acid sequence of genes involved in IBDs, and other inflammatory diseases, and also the use of these nucleic acid sequences.

In the context of the present invention, preliminary studies by the inventors have already made it possible to locate a CD-susceptibility gene. Specifically, the inventors (Hugot et al., 1996) have shown that a CD-susceptibility gene is located in the pericentromeric region of chromosome 16 (FIG. 1). It was the first gene for susceptibility to a complex genetic disease located by positional cloning and satisfying the strict criteria proposed in the literature (Lander and Kruglyak, 1995). This gene was named IBD1 (for inflammatory bowel disease 1). Since then, other locations have been proposed by other authors, in particular on chromosomes 12, 1, 3, 6 and 7 (Satsangi et al., 1996; Cho et al., 1998). Although they have been located, it has currently not been possible to identify any of these IBD-susceptibility genes.

Some authors have not been able to replicate this location (Pioux et al., 1998). This is not, however, surprising in the case of complex genetic diseases in which genetic heterogeneity is probable.

It is interesting to note that, according to the same approach of positional cloning, locations have also been proposed on chromosome 16 for several immune and inflammatory diseases, such as ankylosing spondylarthritis, Blau's syndrome, psoriasis, etc. (Becker et al., 1998; Tromp et al., 1996). All these diseases may then share the same gene (or the same group of genes) located on chromosome 16.

A maximum of genetic linkage tests is virtually always located at the same position, in the region of D16S409 or D16S411, separated only by 2 cM. This result contradicts the considerable size (usually greater than 20 cM) of the confidence interval which can be attributed to the genetic location according to an approach using nonparametric linkage analyses.

Comparison of the statistical tests used in the studies by the inventors shows that the tests based on complete identity by decendance (Tz2) are better than the tests based on the mean of identity by decendance (Tz) (FIG. 1). Such a difference can be explained by a recessive effect of IBD1.

Several genes known to be in the pericentromeric region of chromosome 16, such as the interleukin 4 receptor, CD19, CD43 or CD11, appear to be good potential candidates for CD. Preliminary results do not however plead in favor of these genes being involved in CD.

In particular, the present invention provides not only the sequence of IBD1 gene, but also the partial sequence of another gene, called IBD1prox due to it being located in proximity to IBD, and demonstrated as reported in the examples below. These genes, the cDNA sequence of which corresponds, respectively, to SEQ ID No. 1 and SEQ ID No. 4, are therefore potentially involved in many inflammatory and/or immune diseases and also in cancers.

The peptide sequence expressed by the IBD1 and IBD1prox genes is represented by SEQ ID No. 2 and SEQ ID No. 5, respectively; the genomic sequence of these genes is represented by SEQ ID No. 3 and SEQ ID No. 6, respectively.

Thus, a subject of the present invention is a purified or isolated nucleic acid, characterized in that it comprises a nucleic acid sequence chosen from the following group of sequences:

a) SEQ ID No. 1, SEQ ID No. 3, SEQ ID No. 4 and SEQ ID No. 6;
b) the sequence of a fragment of at least 15 consecutive nucleotides of a sequence chosen from SEQ ID No. 1, SEQ ID No. 3, SEQ ID No. 4 or SEQ ID No. 6;
c) a nucleic acid sequence having a percentage identity of at least 80%, after optimal alignment, with a sequence defined in a) or b);
d) a nucleic acid sequence which hybridizes, under high stringency conditions, with a nucleic acid sequence defined in a) or b);
e) the complementary sequence or the RNA sequence corresponding to a sequence as defined in a), b), c) or d).

The nucleic acid sequence according to the invention defined in c) has a percentage identity of at least 80%, after optimal alignment, with a sequence as defined in a) or b) above, preferably 90%, most preferably 98%.

The terms "nucleic acid", "nucleic acid sequence", "polynucleotide", "oligonucleotide", "polynucleotide sequence" and "nucleotide sequence", terms which will he employed indifferently in the present description, are intended to denote a precise series of nucleotides, which may or may not be modified, making it possible to define a fragment or a region of a nucleic acid, which may or may not comprise unnatural nucleotides, and which may correspond equally to a double-stranded DNA, a single-stranded DNA and transcription products of said DNAs. Thus, the nucleic acid sequences according to the invention also encompass PNAs (Peptide Nucleic Acids), or the like.

It should be understood that the present invention does not relate to the nucleotide sequences in their natural chromosomal environment, that is to say in the natural state. They are sequences which have been isolated and/or purified, that is to say they have been taken directly or indirectly, for example by copying, their environment having been at least partially modified. Thus, nucleic acids obtained by chemical synthesis are also intended to be denoted.

For the purpose of the present invention, the term "percentage identity" between two nucleic acid or amino acid sequences is intended to denote a percentage of nucleotides or of amino acid residues which are identical between the two sequences to be compared, obtained after the best alignment, this percentage being purely statistical and the differences between the two sequences being distributed randomly and over their entire length. The term "best alignment" or "optimal alignment" is intended to denote the alignment for which the percentage identity determined as below is highest. Sequence comparisons between two nucleic acid or amino acid sequences are conventionally carried out by comparing these sequences after having aligned them optimally, said comparison being carried out by segment or by "window of comparison" so as to identify and compare local regions of sequence similarity. The optimal alignment of the sequences for the comparison may be carried out, besides manually, by means of the local homology algorithm of Smith and Waterman (1981), by means of the local homology algorithm of Neddleman and Wunsch (1970), by means of the similarity search method of Pearson and Lipman (1988), by means of computer programs using these algorithms (GAP, BESTFIT, BLAST P, BLAST N, FASTA and TFASTA in the Wisconsin Genetics Software Package, Genetics Computer Group, 575 Science Dr., Madison, Wis.). In order to obtain the optimal alignment, the BLAST program is preferably used, with the BLOSUM 62 matrix. The PAN or PAM250 matrices may also be used.

The percentage identity between two nucleic acid or amino acid sequences is determined by comparing these two sequences aligned optimally, the nucleic acid or amino acid sequence to be compared possibly comprising additions or deletions with respect to the reference sequence for optimal alignment between these two sequences. The percentage identity is calculated by determining the number of identical positions for which the nucleotide or the amino acid residue is identical between the two sequences, dividing this number of identical positions by the total number of positions compared and multiplying the resultant number by 100 so as to obtain the percentage identity between these two sequences.

The expression "nucleic acid sequences having a percentage identity of at least 80%, preferably 90%, more preferably 98%, after optimal alignment with a reference sequence" is intended to denote the nucleic acid sequences which, compared to the reference nucleic acid sequence, have certain modifications, such as in particular a deletion, a truncation, an extension, a chimeric fusion and/or a substitution, in particular of the point type, and the nucleic acid sequence of which exhibits at least 80%, preferably 90%, more preferably 98%, identity, after optimal alignment, with the reference nucleic acid sequence. They are preferably sequences whose complementary sequences are capable of hybridizing specifically with the sequence SEQ ID No. 1 or SEQ ID No. 4 of the invention. Preferably, the specific or high stringency hybridization conditions will be such that they ensure at least 80%, preferably 90%, more preferably 98%, identity, after optimal alignment, between one of the two sequences and the sequence complementary to the other.

Hybridization under high stringency conditions means that the conditions of temperature and of ionic strength are chosen such that they allow the hybridization between two complementary DNA fragments to be maintained. By way of illustration, high stringency conditions for the hybridization step for the purposes of defining the polynucleotide fragments described above are advantageously as follows.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a solution of 0.15 M NaCl+0.015 M sodium citrate), 50% of formamide, 7% of sodium dodecyl sulfate (SDS), 10× Denhardt's, 5% of dextran sulfate and 1% of salmon sperm DNA; (2) hybridization per se for 20 hours at a temperature which depends on the length of the probe (i.e.: 42° C. for a probe >100 nucleotides in length), followed by 2 washes of 20 minutes at 20° C. in 2×SSC+2% SDS and 1 wash of 20 minutes at 20° C. in 0.1×SSC+0.1% SDS. The final wash is carried out in 0.1×SSC+0.1% SDS for 30 minutes at 60° C. for a probe >100 nucleotides in length. The high stringency hybridization conditions described above for a polynucleotide of defined length may be adjusted by those skilled in the art for longer or shorter oligonucleotides, according to the teaching of Sambrook et al., 1989.

Among the nucleic acid sequences having a percentage identity of at least 80%, preferably 90%, more preferably 98%, after optimal alignment, with the sequence according to the invention, preference is also given to the variant nucleic acid sequences of SEQ ID No. 1 or of SEQ ID No. 4, or of fragments thereof, that is to say all the nucleic acid sequences corresponding to allelic variants, that is to say individual variations of the sequence SEQ ID No. 1 or SEQ ID No. 4. These natural mutated sequences correspond to polymorphisms present in mammals, in particular in humans and, in particular, to polymorphisms which may lead to the occurrence of a pathological condition. Preferably, the present invention relates to the variant nucleic acid sequences in which the mutations lead to a modification of the amino acid sequence of the polypeptide, or of fragments thereof, encoded by the normal sequence of SEQ ID No. 1 or SEQ ID No. 4.

The expression "variant nucleic acid sequence" is also intended to denote any RNA or cDNA resulting from a mutation and/or variation of a splice site of the genomic nucleic acid sequence the cDNA of which has the sequence SEQ ID No. 1 or SEQ ID No. 4.

The invention preferably relates to a purified or isolated nucleic acid according to the present invention, characterized in that it comprises or consists of one of the sequences SEQ ID No. 1 or SEQ ID No. 4, of the sequences complementary thereto, or of the RNA sequences corresponding to SEQ ID No. 1 or SEQ ID No. 4.

The probes or primers, characterized in that they comprise a sequence of a nucleic acid according to the invention, are also part of the invention.

Thus, the present invention also relates to the primers or the probes according to the invention which may make it possible in particular to demonstrate or to distinguish the variant nucleic acid sequences, or to identify the genomic sequence of the genes the cDNA of which is represented by SEQ ID No. 1 or SEQ ID No. 4, in particular using an amplification method such as the PCR method or a related method.

The invention also relates to the use of a nucleic acid sequence according to the invention, as a probe or primer, for detecting, identifying, assaying or amplifying a nucleic acid sequence.

According to the invention, the polynucleotides which can be used as a probe or as a primer in methods for detecting, identifying, assaying or amplifying a nucleic acid sequence are a minimum of 15 bases, preferably 20 bases, or better still 25 to 30 bases in length.

The probes and primers according to the invention may be labeled directly or indirectly with a radioactive or nonradioactive compound using methods well known to those skilled in the art, in order to obtain a detectable and/or quantifiable signal.

The polynucleotide sequences according to the invention which are unlabeled can be used directly as a probe or primer.

The sequences are generally labeled so as to obtain sequences which can be used in many applications. The primers or the probes according to the invention are labeled with radioactive elements or with nonradioactive molecules.

Among the radioactive isotopes used, mention may be made of $^{32}P$, $^{33}P$, $^{35}S$, $^{3}H$ or $^{125}I$. The nonradioactive entities are selected from ligands such as biotin, avidin, streptavidin or dioxygenin, haptens, dyes and luminescent agents, such as radioluminescent, chemiluminescent, bioluminescent, fluorescent or phosphorescent agents.

The polynucleotides according to the invention may thus be used as a primer and/or probe in methods using in particular the PCR (polymerase chain reaction) technique (Rolfs et al., 1991). This technique requires choosing pairs of oligonucleotide primers bordering the fragment which must be amplified. Reference may, for example, be made to the technique described in U.S. Pat. No. 4,683,202. The amplified fragments can be identified, for example after agarose or polyacrylamide gel electrophoresis, or after a chromatographic technique such as gel filtration or ion exchange chromatography, and then sequenced. The specificity of the amplification can be controlled using, as primers, the nucleotide sequences of polynucleotides of the invention and, as matrices, plasmids containing these sequences or else the derived amplification products. The amplified nucleotide fragments may be used as reagents in hybridization reactions in order to demonstrate the presence, in a biological sample, of a target nucleic acid of sequence complementary to that of said amplified nucleotide fragments.

The invention is also directed toward the nucleic acids which can be obtained by amplification using primers according to the invention.

Other techniques for amplifying the target nucleic acid may advantageously be employed as an alternative to PCR (PCR-like) using a pair of primers of nucleotide sequences according to the invention. The term "PCR-like" is intended to denote all the methods using direct or indirect reproductions of nucleic acid sequences, or else in which the labeling systems have been amplified; these techniques are, of course, known. In general, they involve amplifying the DNA with a polymerase; when the sample of origin is an RNA a reverse transcription should be carried out beforehand. A large number of methods currently exist for this amplification, such as, for example, the SDA (strand displacement amplification) technique (Walker et al., 1992), the TAS (transcription-based amplification system) technique described by Kwoh et al. (1989), the 3SR (self-sustained sequence replication) technique described by Guatelli et al. (1990), the NASBA (nucleic acid sequence based amplification) technique described by Kievitis et al. (1991), the TMA (transcription mediated amplification) technique, the LCR (ligase chain reaction) technique described by Landegren et al. (1988), the RCR (repair chain reaction) technique described by Segev (1992), the CPR (cycling probe reaction) technique described by Duck et al. (1990), and the Q-beta-replicase amplification technique described by Miele et al. (1983). Some of these techniques have since been improved.

When the target polynucleotide to be detected is an mRNA, an enzyme of the reverse transcriptase type is advantageously used, prior to carrying out an amplification reaction using the primers according to the invention or to carrying out a method of detection using the probes of the invention, in order to obtain a cDNA from the mRNA contained in the biological sample. The cDNA obtained will then serve as a target for the primers or the probes used in the amplification or detection method according to the invention.

The probe hybridization technique may be carried out in many ways (Matthews et al., 1988). The most general method consists in immobilizing the nucleic acid extracted from the cells of various tissues or from cells in culture, on a support (such as nitrocellulose, nylon or polystyrene), and in incubating the immobilized target nucleic acid with the probe, under well-defined conditions. After hybridization, the excess probe is removed and the hybrid molecules formed are detected using the appropriate method (measuring the radioactivity, the fluorescence or the enzymatic activity linked to the probe).

According to another embodiment of the nucleic acid probes according to the invention, the latter may be used as capture probes. In this case, a probe, termed "capture probe", is immobilized on a support and is used to capture, by specific hybridization, the target nucleic acid obtained from the biological sample to be tested, and the target nucleic acid is then detected using a second probe, termed "detection probe", labeled with a readily detectable element.

Among the advantageous nucleic acid fragments, mention should thus be made in particular of antisense oligonucleotides, i.e. oligonucleotides, the structure of which ensures, by hybridization with the target sequence, inhibition of expression of the corresponding product. Mention should also be made of sense oligonucleotides, which, by interacting with proteins involved in regulating the expression of the corresponding product, will induce either inhibition or activation of this expression.

In both cases (sense and antisense), the oligonucleotides of the invention may be used in vitro and in vivo.

The present invention also relates to an isolated polypeptide, characterized in that it comprises a polypeptide chosen from:
a) a polypeptide of sequence SEQ ID No. 2 or SEQ ID No. 5;
b) a variant polypeptide of a polypeptide of sequence defined in a);
c) a polypeptide homologous to a polypeptide defined in a) or b), comprising at least 80% identity with said polypeptide of a);
d) a fragment of at least 15 consecutive amino acids of a polypeptide defined in a), b) or c);
e) a biologically active fragment of a polypeptide defined in a), b) or c).

For the purpose of the present invention, the term "polypeptide" is intended to denote proteins or peptides.

The expression "biologically active fragment" is intended to mean a fragment having the same biological activity as the peptide fragment from which it is deduced, preferably within the same order of magnitude (to within a factor of 10). Thus, the examples show that the IBD1 protein (SEQ ID No. 2) has a potential role in apoptosis phenomena. A biologically active fragment of the IBD1 protein therefore consists of a polypeptide derived from SEQ ID No. 2, also having a role in apoptosis. The examples below propose biological functions for the IBD1 and IBD1prox proteins, as a function of the peptide domains of these proteins, and thus allow those skilled in the art to identify the biologically active fragments.

Preferably, a polypeptide according to the invention is a polypeptide consisting of the sequence SEQ ID No. 2 (corresponding to the protein encoded by the IBD1 gene) or of the sequence SEQ ID No. 5 (corresponding to the protein encoded by IBD1prox) or of a sequence having at least 80% identity with SEQ ID No. 2 or SEQ ID No. 5 after optimal alignment.

The sequence of the polypeptide has a percentage identity of at least 80%, after optimal alignment, with the sequence SEQ ID No. 2 or SEQ ID No. 5, preferably 90%, more preferably 98%.

The expression "polypeptide, the amino acid sequence of which has a percentage identity of at least 80%, preferably 90%, more preferably 98%, after optimal alignment, with a reference sequence" is intended to denote the polypeptides having certain modifications compared to the reference polypeptide, such as in particular one or more deletions and/or truncations, an extension, a chimeric fusion and/or one or more substitutions.

Among the polypeptides, the amino acid sequence of which has a percentage identity of at least 80%, preferably 90%, more preferably 98%, after optimal alignment, with the sequence SEQ ID No. 2 or SEQ ID No. 5 or with a fragment thereof according to the invention, preference is given to the variant polypeptides encoded by the variant nucleic acid sequences as defined previously, in particular the polypeptides, the amino acid sequence of which has at least one mutation corresponding in particular to a truncation, deletion, substitution and/or addition of at least one amino acid residue compared with the sequence SEQ ID No. 2 or SEQ ID No. 5 or with a fragment thereof, more preferably the variant polypeptides having a mutation associated with the pathological condition.

The present invention also relates to the cloning and/or expression vectors comprising a nucleic acid or encoding a polypeptide according to the invention. Such a vector may also contain the elements required for the expression and, optionally, the secretion of the polypeptide in a host cell. Such a host cell is also a subject of the invention.

The vectors characterized in that they comprise a promoter and/or regulator sequence according to the invention are also part of the invention.

Said vectors preferably comprise a promoter, translation initiation and termination signals, and also regions suitable for regulating transcription. It must be possible for them to be maintained stably in the cell and they may optionally contain particular signals specifying secretion of the translated protein.

These various control signals are chosen as a function of the cellular host used. To this effect, the nucleic acid sequences according to the invention may be inserted into vectors which replicate autonomously in the chosen host, or vectors which integrate in the chosen host.

Among the systems which replicate autonomously, use is preferably made, depending on the host cell, of systems of the plasmid or viral type, the viral vectors possibly being in particular adenoviruses (Perricaudet et al., 1992), retroviruses, lentiviruses, poxyiruses or herpesviruses (Epstein et al., 1992). Those skilled in the art are aware of the technology which can be used for each of these systems.

When integration of the sequence into the chromosomes of the host cell is desired, use may he made, for example, of systems of the plasmid or viral type; such viruses are, for example, retroviruses (Temin, 1986), or AAVs (Carter, 1993).

Among the nonviral vectors, preference is given to naked polynucleotides such as naked DNA or naked RNA according to the technology developed by the company VICAL, bacterial artificial chromosomes (BACs), yeast artificial chromosomes (YACs) for expression in yeast, mouse artificial chromosomes (MACs) for expression in murine cells and, preferably, human artificial chromosomes (HACs) for expression in human cells.

Such vectors are prepared according to the methods commonly used by those skilled in the art, and the clones resulting therefrom can be introduced into a suitable host using standard methods, such as, for example, lipofection, electroporation, heat shock, transformation after chemical permeabilization of the membrane, or cell fusion.

The invention also comprises host cells, in particular the eukaryotic and prokaryotic cells, transformed with the vectors according to the invention, and also the transgenic animals, preferably the mammals, except humans, comprising one of said transformed cells according to the invention. These animals may be used as models, for studying the etiology of inflammatory and/or immune diseases, in particular of the inflammatory diseases of the digestive tract, or for studying cancers.

Among the cells which can be used for the purpose of the present invention, mention may be made of bacterial cells (Olins and Lee, 1993), but also yeast cells (Buckholz, 1993)

as well as animal cells, in particular mammalian cell cultures (Edwards and Aruffo, 1993), and especially Chinese hamster ovary (CHO) cells. Mention may also be made of insect cells in which it is possible to use methods employing, for example, baculo viruses (Luckow, 1993). A preferred cellular host for expressing the proteins of the invention consists of COS cells.

Among the mammals according to the invention, animals such as rodents, in particular mice, rats or rabbits, expressing a polypeptide according to the invention are preferred.

Among the mammals according to the invention, preference is also given to animals such as mice, rats or rabbits, characterized in that the gene encoding the protein of sequence SEQ ID No. 2 or SEQ ID No. 5, or the sequence of which is encoded by the homologous gene in these animals, is not functional, has been knocked out or has at least one mutation.

These transgenic animals are obtained, for example, by homologous recombination on embryonic stem cells, transfer of these stem cells to embryos, selection of the chimeras affected in the reproductive lines, and growth of said chimeras.

The transgenic animals according to the invention may thus overexpress the gene encoding the protein according to the invention, or their homologous gene, or express said gene into which a mutation is introduced. These transgenic animals, in particular mice, are obtained, for example, by transfection of a copy of this gene under the control of a promoter which is strong and ubiquitous, or selective for a tissue type, or after viral transcription.

Alternatively, the transgenic animals according to the invention may be made deficient for the gene encoding one of the polypeptides of sequence SEQ ID No. 2 or SEQ ID No. 5, or their homologous genes, by inactivation using the LOXP/CRE recombinase system (Rohlmann et al., 1996) or any other system for inactivating the expression of this gene.

The cells and mammals according to the invention can be used in a method for producing a polypeptide according to the invention, as described below, and may also be used as a model for analysis.

The cells or mammals transformed as described above can also be used as models in order to study the interactions between the polypeptides according to the invention, and the chemical or protein compounds involved directly or indirectly in the activities of the polypeptides according to the invention, this being in order to study the various mechanisms and interactions involved.

They may in particular be used for selecting products which interact with the polypeptides according to the invention, in particular the protein of sequence SEQ ID No. 2 or SEQ ID No. 5 or variants thereof according to the invention, as a cofactor or as an inhibitor, in particular a competitive inhibitor, or which have an agonist or antagonist activity with respect to the activity of the polypeptides according to the invention. Preferably, said transformed cells or transgenic animals are used as a model in particular for selecting products for combating pathological conditions associated with abnormal expression of this gene.

The invention also relates to the use of a cell, of a mammal or of a polypeptide according to the invention, for screening chemical or biochemical compounds which may interact directly or indirectly with the polypeptides according to the invention, and/or which are capable of modulating the expression or the activity of these polypeptides.

Similarly, the invention also relates to a method for screening compounds capable of interacting, in vitro or in vivo, with a nucleic acid according to the invention, using a nucleic acid, a cell or a mammal according to the invention, and detecting the formation of a complex between the candidate compounds and the nucleic acid according to the invention.

The compounds thus selected are also subjects of the invention.

The invention also relates to the use of a nucleic acid sequence according to the invention, for synthesizing recombinant polypeptides.

The method for producing a polypeptide of the invention in recombinant form, which is itself included in the present invention, is characterized in that the transformed cells, in particular the cells or mammals of the present invention, are cultured under conditions which allow the expression of a recombinant polypeptide encoded by a nucleic acid sequence according to the invention, and in that said recombinant polypeptide is recovered.

The recombinant polypeptides, characterized in that they can be obtained using said method of production, are also part of the invention.

The recombinant polypeptides obtained as indicated above can be in both glycosylated and nonglycosylated form, and may or may not have the natural tertiary structure.

The sequences of the recombinant polypeptides may also be modified in order to improve their solubility, in particular in aqueous solvents.

Such modifications are known to those skilled in the art, such as, for example, deletion of hydrophobic domains or substitution of hydrophobic amino acids with hydrophilic amino acids.

These polypeptides may be produced using the nucleic acid sequences defined above, according to the techniques for producing recombinant polypeptides known to those skilled in the art. In this case, the nucleic acid sequence used is placed under the control of signals which allow its expression in a cellular host An effective system for producing a recombinant polypeptide requires having a vector and a host cell according to the invention.

These cells can be obtained by introducing into host cells a nucleotide sequence inserted into a vector as defined above, and then culturing said cells under conditions which allow the replication and/or expression of the transfected nucleotide sequence.

The methods used for purifying a recombinant polypeptide are known to those skilled in the art. The recombinant polypeptide may be purified from cell lysates and extracts or from the culture medium supernatant, by methods used individually or in combination, such as fractionation, chromatography methods, immunoaffinity techniques using specific monoclonal or polyclonal antibodies, etc.

The polypeptides according to the present invention can also be obtained by chemical synthesis using one of the many known forms of peptide synthesis, for example techniques using solid phases (see in particular Stewart et al., 1984) or techniques using partial solid phases, by fragment condensation or by conventional synthesis in solution.

The polypeptides obtained by chemical synthesis and which may comprise corresponding unnatural amino acids are also included in the invention.

The mono- or polyclonal antibodies, or fragments thereof, chimeric antibodies or immunoconjugates, characterized in that they are capable of specifically recognizing a polypeptide according to the invention, are part of the invention.

Specific polyclonal antibodies may be obtained from a serum of an animal immunized against the polypeptides according to the invention, in particular produced by genetic recombination or by peptide synthesis, according to the usual procedures.

The advantage of antibodies which specifically recognize certain polypeptides, variants or immunogenic fragments thereof according to the invention is in particular noted.

The mono- or polyclonal antibodies, or fragments thereof, chimeric antibodies or immunoconjugates characterized in that they are capable of specifically recognizing the polypeptides of sequence SEQ ID No. 2 or SEQ ID No. 5 are particularly preferred.

The specific monoclonal antibodies may be obtained according to the conventional method of hybridoma culture described by Köhler and Milstein (1975).

The antibodies according to the invention are, for example, chimeric antibodies, humanized antibodies, or Fab or F(ab')$_2$ fragments. They may also be in the form of immunoconjugates or of labeled antibodies, in order to obtain a detectable and/or quantifiable signal.

The invention also relates to methods for detecting and/or purifying a polypeptide according to the invention, characterized in that they use an antibody according to the invention.

The invention also comprises purified polypeptides, characterized in that they are obtained using a method according to the invention.

Moreover, besides their use for purifying the polypeptides, the antibodies of the invention, in particular the monoclonal antibodies, may also he used for detecting these polypeptides in a biological sample.

They thus constitute a means for the immunocytochemical or immunohistochemical analysis of the expression of the polypeptides according to the invention, in particular the polypeptides of sequence SEQ ID No. 2 or SEQ ID No. 5, or a variant thereof, on specific tissue sections, for example using immunofluorescence, gold labeling and/or enzymatic immunoconjugates.

They may in particular make it possible to demonstrate abnormal expression of these polypeptides in the biological specimens or tissues.

More generally, the antibodies of the invention may advantageously be used in any situation where the expression of a polypeptide according to the invention, normal or mutated, must be observed.

Thus, a method for detecting a polypeptide according to the invention, in a biological sample, comprising the steps of bringing the biological sample into contact with an antibody according to the invention and demonstrating the antigen-antibody complex formed, is also a subject of the invention, as is a kit for carrying out such a method. Such a kit in particular contains:

a) a monoclonal or polyclonal antibody according to the invention;
b) optionally, reagents for constituting a medium suitable for the immunoreaction;
c) the reagents for detecting the antigen-antibody complex produced during the immunoreaction.

The antibodies according to the invention may also be used in the treatment of an inflammatory and/or immune disease, or of a cancer, in humans, when abnormal expression of the IBD1 gene or of the IBD1prox gene is observed. Abnormal expression means overexpression or the expression of a mutated protein.

These antibodies may be obtained directly from human serum, or may be obtained from animals immunized with polypeptides according to the invention, and then "human-ized", and may be used as such or in the preparation of a medicinal product intended for the treatment of the above-mentioned diseases.

The methods for determining an allelic variability, a mutation, a deletion, a loss of heterozygocity or any genetic abnormability of the gene according to the invention, characterized in that they use a nucleic acid sequence, a polypeptide or an antibody according to the invention, are also part of the invention.

The invention in fact provides the sequence of the IBD1 and IBD1prox genes involved in inflammatory and/or immune diseases, and in particular IBDs. One of the teachings of the invention is to specify the mutations, in these nucleic acid or polypeptide sequences, which are associated with a phenotype corresponding to one of these inflammatory and/or immune diseases.

These mutations can be detected directly by analysis of the nucleic acid and of the sequences according to the invention (genomic DNA, RNA or cDNA), but also via the polypeptides according to the invention. In particular, the use of an antibody according to the invention which recognizes an epitope bearing a mutation makes it possible to distinguish between a "healthy" protein and a protein "associated with a pathological condition".

Thus, the study of the IBD1 gene in various inflammatory and/or immune human diseases thus shows that sequence variants of this gene exist in Crohn's disease, ulcerative colitis and Blau's syndrome, as demonstrated by the examples. These sequence variations result in considerable variations in the deduced protein sequence. In fact, they are either located on very conserved sites of the protein in important functional domains, or they result in the synthesis of a truncated protein. It is therefore extremely probable that these deleterious modifications lead to a modification of the function of the protein and therefore have a causal effect in the occurrence of these diseases.

The variety of diseases in which these mutations are observed suggests that the IBD1 gene is potentially important in many inflammatory and/or immune diseases. This result should be compared with the fact that the pericentromeric region of chromosome 16 has been described as containing genes for susceptibility to various human diseases, such as ankylosing spondylarthritis or psoriatic arthropathy. It may therefore be considered that IBD1 has an important role in a large number of inflammatory and/or immune diseases.

In particular, IBD1 can be associated with granulomatous inflammatory diseases. Blau's syndrome and CD are in fact diseases which are part of this family. It is therefore hoped that variations in the IBD1 gene will be found for the other diseases of the same family (sarcoidosis, Behcet's disease, etc.).

In addition, the involvement of IBD1 in the cellular pathways leading to apoptosis raises the question of its possible carcinogenic role. In fact, it is expected that a dysregulation of IBD1 may result in a predisposition to cancer. This hypothesis is supported by the fact that a predisposition to colon cancer exists in inflammatory bowel diseases. IBD1 may in part explain this susceptibility to cancer and define new carcinogenic pathways.

The precise description of the mutations which can be observed in the IBD1 gene thus makes it possible to lay down the foundations of a molecular diagnosis for the inflammatory or immune diseases in which this role is demonstrated. Such an approach, based on searching for mutations in the gene, will make it possible to contribute to the diagnosis of these diseases and possibly to reduce the extent of certain additional examinations which are invasive or expensive. The invention lays down the foundations of such a molecular diagnosis based on searching for mutations in IBD1.

The molecular diagnosis of inflammatory diseases should also make it possible to improve the nosological classification of these diseases and to more clearly define subgroups of particular diseases by their clinical characteristics, the progressive nature of the disease or the response to certain treatments. By way of example, the dismantling of the existing mutations may thus make it possible to classify the currently undetermined forms of colitis which represent more than 10% of inflammatory bowel diseases. Such an approach will make it possible to propose an early treatment suitable for each patient. In general, such an approach makes it possible to hope that it will eventually be possible to define an individualized treatment for the disease, depending on the genetic area of each disease, including curative and preventive measures.

In particular, preference is given to a method of diagnosis and/or of prognostic assessment of an inflammatory disease or of a cancer, characterized in that the presence of at least one mutation and/or a deleterious modification of expression of the gene corresponding to SEQ ID No. 1 or SEQ ID No. 4 is determined, using a biological specimen from a patient, by analyzing all or part of a nucleic acid sequence corresponding to said gene. The genes SEQ ID No. 3 or SEQ ID No. 6 may also be studied.

This method of diagnosis and/or of prognostic assessment may be used preventively (a study of predisposition to inflammatory diseases or to cancer), or in order to serve in establishing and/or confirming a clinical condition in a patient.

Preferably, the inflammatory disease is an inflammatory disease of the digestive tract, and the cancer is a cancer of the digestive tract (small intestine or colon).

The teaching of the invention in fact makes it possible to determine the mutations which exhibit a linkage disequilibrium with inflammatory diseases of the digestive tract, and which are therefore associated with such diseases.

The analysis may be carried out by sequencing all or part of the gene, or by other methods known to those skilled in the art. Methods based on PCR, for example PCR-SSCP, which makes it possible to detect point mutations, may in particular be used.

The analysis may also be carried out by attaching a probe according to the invention, corresponding to one of the sequences SEQ ID No. 1, 3, 4 or 6, to a DNA chip, and hybridization on these microplates. A DNA chip containing a sequence according to the invention is also one of the subjects of the invention.

Similarly, a protein chip containing an amino acid sequence according to the invention is also a subject of the invention. Such a protein chip makes it possible to study the interactions between the polypeptides according to the invention and other proteins or chemical compounds, and may thus be useful for screening compounds which interact with the polypeptides according to the invention. The protein chips according to the invention may also be used to detect the presence of antibodies directed against the polypeptides according to the invention in the serum of patients. A protein chip containing an antibody according to the invention may also be used.

Those skilled in the art are also able to carry out techniques for studying the deleterious modification of the expression of a gene, for example by studying the mRNA (in particular by Northern blotting or with RT-PCR experiments, with probes or primers according to the invention), or the protein expressed, in particular by Western blotting, using antibodies according to the invention.

The gene tested is preferably the gene of sequence SEQ ID No. 1, the inflammatory disease for which the intention is to predict susceptibility being a disease of the digestive tract, in particular Crohn's disease or ulcerative colitis. If the intention is to detect a cancer, it is preferably colon cancer.

The invention also relates to methods for obtaining an allele of the IBD1 gene, associated with a detectable phenotype, comprising the following steps:

a) obtaining a nucleic acid sample from an individual expressing said detectable phenotype;

b) bringing said nucleic acid sample into contact with an agent capable of specifically detecting a nucleic acid encoding the IBD1 protein;

c) isolating said nucleic acid encoding the IBD1 protein.

Such a method may be followed by a step of sequencing all or part of the nucleic acid encoding the IBD1 protein, which makes it possible to predict susceptibility to inflammatory disease or of a cancer.

The agent capable of specifically detecting a nucleic acid encoding the IBD1 protein is advantageously an oligonucleotide probe according to the invention, which may be made up of DNA, RNA or PNA, which may or may not be modified. The modifications may include radioactive or fluorescent labeling, or may be due to modifications in the bonds between the bases (phosphorothioates or methyl phosphonates, for example). Those skilled in the art are aware of the protocols for isolating a specific DNA sequence. Step b) of the method described above may also be an amplification step as described above.

The invention also relates to a method for detecting and/or assaying a nucleic acid according to the invention, in a biological sample, comprising the following steps of bringing a probe according to the invention into contact with a biological sample, and detecting and/or assaying the hybrid formed between said polynucleotide and the nucleic acid of the biological sample.

Those skilled in the art are capable of carrying out such a method, and may in particular use a kit of reagents, comprising:

a) a polynucleotide according to the invention, used as a probe;

b) the reagents required for carrying out a hybridization reaction between said probe and the nucleic acid of the biological sample;

c) the reagents required for detecting and/or assaying the hybrid formed between said probe and the nucleic acid of the biological sample;

which is also a subject of the invention.

Such a kit may also contain positive or negative controls in order to ensure the quality of the results obtained.

However, in order to detect and/or assay a nucleic acid according to the invention, those skilled in the art may also perform an amplification step using primers chosen from the sequences according to the invention.

Finally, the invention also relates to the compounds chosen from a nucleic acid, a polypeptide, a vector, a cell or an antibody according to the invention, or the compounds obtained using the screening methods according to the invention, as a medicinal product, in particular for preventing and/or treating an inflammatory and/or immune disease, or a cancer, associated with the presence of at least one mutation of the gene corresponding to SEQ ID No. 1 or SEQ ID No. 4, preferably an inflammatory disease of the digestive tract, in particular Crohn's disease or ulcerative colitis.

The following examples make it possible to understand more clearly the advantages of the invention, and should not be considered to limit the scope of the invention.

A: The translation produced deduced from the cDNA sequence of the IBD1 candidate gene is identical to that of NOD2 (Ogura et al., 2000). The polypeptide contains 2 CARD domains (CAspase Recruitment Domains), a nucleotide-binding domain (NBD) and 10 repeats of 27 amino acids, leucine-rich motifs (LRR). The consensus sequence of the ATP/GTP-binding site of the motif A (P loop) of the NBD is indicated with a black circle. The sequence changes encoded by the three main variants associated with CD are SNP 8 (R675W), SNP 12 (G881R) and SNP 13 (frame shift 980). The frame shift changes a leucine codon to a proline codon at position 980, which is immediately followed by a stop codon.

B: Rare missense variants of NOD2 in 457 CD patients, 159 UC patients and 103 unaffected, unrelated individuals. The positions of the rare missense variants are indicated for the three groups. The scale on the left indicates the number of each variant identified in the groups under investigation and that on the right measures the frequency of the mutation. The allelic frequencies of the polymorphism V9281 was not significantly different (0.92:0.08) in the three groups and the corresponding genotypes were in Hardy-Weinberg equilibrium.

EXAMPLES

Example 1

Fine Location of IBD1

Figure 1:
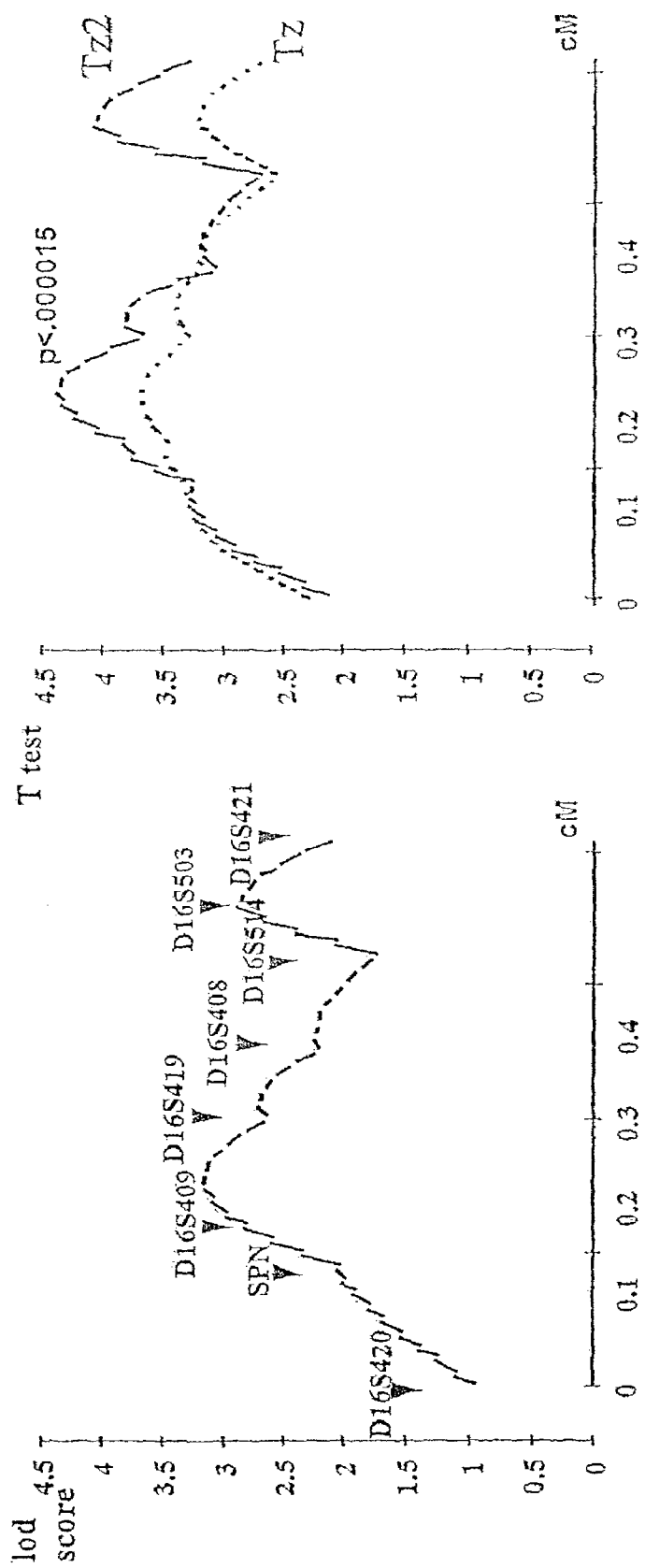
FIG. 1: Nonparametric genetic linkage tests for Crohn's disease in the pericentromeric region of chromosome 16 (according to Hugot et al., 1996). Multipoint linkage analysis based on identity by decendance for the markers of the pericentromeric region of chromosome 16. The genetic distances between markers were estimated using the CRIMAP program. The lod score (MAPMAKER/SIBS) is indicated on the left-hand figure. Two pseudoprobability tests were developed and reported on the right-hand figure. The first (Tz) is analogous to the test of the means. The second (Tz2) is analogous to the test of the proportion of affected pairs sharing two alleles.

The first step toward identifying the IBD1 gene was to reduce the size of the genetic region of interest, initially centered on the marker D16S411 located between D16S409 and D16S419 (Hugot et al., 1996 and FIG. 1). A group of close markers (high resolution genetic map) was used in order to more clearly specify the genetic region, and made it possible to complete the genetic linkage analyses and to search for a genetic linkage disequilibrium with the disease.

The study related to 78 families comprising at least 2 relatives suffering from CD, which corresponded to 119 affected pairs. The families comprising sick individuals suffering from UC were excluded from the study.

Twenty-six genetic polymorphism markers of the microsatellite type were studied. These markers together made up a high resolution map with an average distance between markers of the order of 1 cM in the genetic region of interest. The characteristics of the markers studied are given in table 1.

TABLE 1

Polymorphic markers of the microsatellite type used for the fine location of IBD1

| Name of polymorphism marker | Cumulative distance (cM) | PCR primers |
|---|---|---|
| D16S3120 | 0 | SEQ ID No. 7 |
| (AFM326vc5) | | SEQ ID No. 8 |
| D16S298 | 2.9 | SEQ ID No. 9 |
| (AFMa189wg5) | | SEQ ID No. 10 |
| D16S299 | 3.4 | SEQ ID No. 11 |
| | | SEQ ID No. 12 |
| SPN | 3.9 | SEQ ID No. 13 |
| | | SEQ ID No. 14 |
| D16S383 | 4.3 | SEQ ID No. 15 |
| | | SEQ ID No. 16 |
| D16S753 | 4.9 | SEQ ID No. 17 |
| (GGAA3G05) | | SEQ ID No. 18 |
| D16S3044 | 5.8 | SEQ ID No. 19 |
| (AFMa222za9) | | SEQ ID No. 20 |
| D16S409 | 5.8 | SEQ ID No. 21 |
| (AFM161xa1) | | SEQ ID No. 22 |
| D16S3105 | 6.1 | SEQ ID No. 23 |
| (AFMb341zc5) | | SEQ ID No. 24 |
| D16S261 | 6.8 | SEQ ID No. 25 |
| (MFD24) | | SEQ ID No. 26 |
| D16S540 | 6.9 | SEQ ID No. 27 |
| (GATA7B02) | | SEQ ID No. 28 |
| D16S3080 | 7 | SEQ ID No. 29 |
| (AFMb068zb9) | | SEQ ID No. 30 |
| D16S517 | 7 | SEQ ID No. 31 |
| (AFMa132we9) | | SEQ ID No. 32 |
| D16S411 | 8 | SEQ ID No. 33 |
| (AFM186xa3) | | SEQ ID No. 34 |
| D16S3035 | 10.4 | SEQ ID No. 35 |
| (AFMa189wg5) | | SEQ ID No. 36 |
| D16S3136 | 10.4 | SEQ ID No. 37 |
| (AFMa061xe5) | | SEQ ID No. 38 |
| D16S541 | 11.4 | SEQ ID No. 39 |
| (GATA7E02) | | SEQ ID No. 40 |
| D16S3117 | 11.5 | SEQ ID No. 41 |
| (AFM288wb1) | | SEQ ID No. 42 |
| D16S416 | 12.4 | SEQ ID No. 43 |
| (AFM210yg3) | | SEQ ID No. 44 |
| D16S770 | 13.2 | SEQ ID No. 45 |
| (GGAA20G02) | | SEQ ID No. 46 |
| D16S2623 | 15 | SEQ ID No. 47 |
| (GATA81B12) | | SEQ ID No. 48 |
| D16S390 | 16.5 | SEQ ID No. 49 |
| | | SEQ ID No. 50 |

TABLE 1-continued

Polymorphic markers of the microsatellite type used for the fine location of IBD1

| Name of polymorphism marker | Cumulative distance (cM) | PCR primers |
|---|---|---|
| D16S419 | 20.4 | SEQ ID No. 51 |
| (AFM225zf2) | | SEQ ID No. 52 |
| D16S771 | 21.8 | SEQ ID No. 53 |
| (GGAA23C09) | | SEQ ID No. 54 |
| D16S408 | 25.6 | SEQ ID No. 55 |
| (AFM137xf8) | | SEQ ID No. 56 |
| D16S508 | 38.4 | SEQ ID No. 57 |
| (AFM304xf1) | | SEQ ID No. 58 |

Each marker is listed according to international nomenclature and mostly by the name proposed by the laboratory of origin. The markers appear according to their order on the chromosome (from 16p to 16q). The genetic distance between the markers (in Kosambi centiMorgans, calculated from the experimental data using the Crimap program) is indicated in the second column. The first polymorphic marker is taken randomly as a reference point. The oligonucleotides which were used for the polymerase chain reaction (PCR) are indicated in the third column.

The genotyping of these microsatellite markers was based on automatic sequencer technology using fluorescent primers. Briefly, after amplification, the fluorescent polymerase chain reaction (PCR) products were loaded onto a polyacrylamide gel on an automatic sequencer according to the manufacturer's recommendations (Perkin Elmer). The size of the alleles for each individual was deduced using the Genescan® and Genotyper® software. The data were then kept on an integrated computer base containing the genealogical, phenotypic and genetic data. They were then used for the genetic linkage analyses.

Several quality controls were carried out throughout the genotyping procedure:
  independent double reading of the genotyping data,
  use of a standard DNA as an internal control for each electrophoretic migration,
  control of the size range for each allele observed,
  search for mendelian transmission errors,
  calculation of the genetic distance between markers (CRI-MAP program) and comparison of this distance with the data from the literature,
  further typing of the markers for which recombination between close markers was observed.

Figure 2:
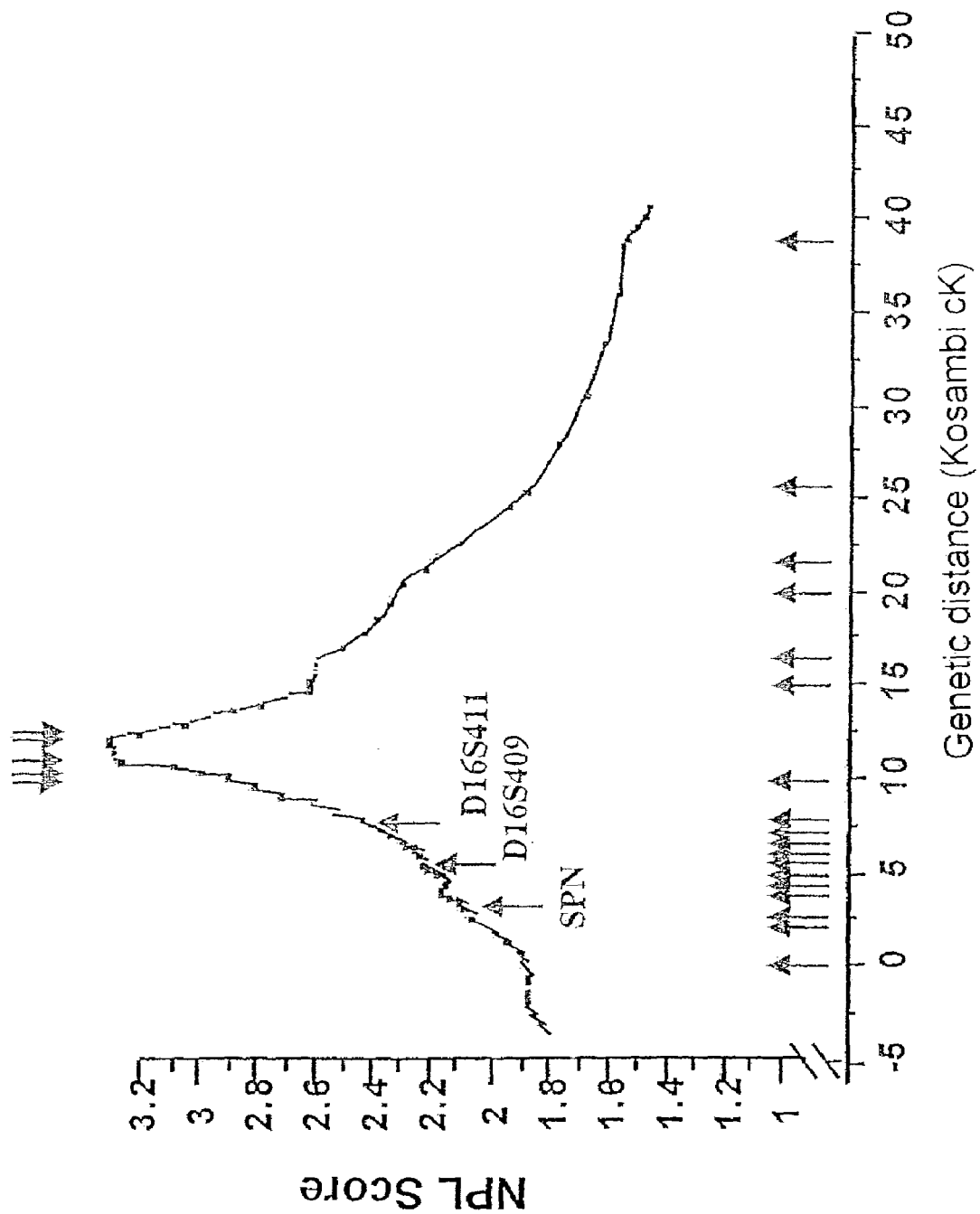
FIG. 2: Multipoint nonparametric genetic linkage analysis. 78 families with several relatives suffering from Crohn's disease were genotyped for 26 polymorphism markers in the pericentromeric region of chromosome 16. The location of each marker is symbolized by an arrow. The order of the markers and the distance separating them derive from the analysis of the experimental data with the Crimap software. The arrows under the curve indicate the markers SPN, D16S409 and D16S411 used in the first study published (Hugot et al., 1996). The arrows located at the top of the figure correspond to the markers D16S3136, D16S541, D16S3117, D16S416 and D16S770 located at the maximum of the genetic linkage test. The typing data were analyzed using the multipoint nonparametric analysis program of the Genehunter software version 1.3. The maximum NPL score is 3.33 (p=0.0004)

The genotyping data were analyzed by multipoint nonparametric genetic linkage methods (GENEHUNTER program version 1.3). The informativeness of the marker system was greater than 80% for the region studied. The test maximum (NPL=3.33; P=0.0004) was obtained for the markers D16S541, D16S3117, D16S770 and D16S416 (FIG. 2).

The typing data for these 26 polymorphism markers were also analyzed so as to search for a transmission disequilibrium. Two groups of 108 and 76 families with one or more sick individuals suffering from CD were studied. The statistical test for transmission disequilibrium has been described by Spielman et al. (1993). In this study, only one sick individual per family was taken into account, and the value of p was corrected by the number of alleles tested for each marker studied.

A transmission disequilibrium was observed for alleles 4 and 5 (size 205 and 207 base pairs, respectively) of the marker D16S3136 (p=0.05 and p=0.01, respectively).

These results, which suggest an association between the marker D16S3136 and CD, led to the construction of a physical map of the genetic region centered on D16S3136 and to establishment of the sequence of a large genomic DNA segment (BAC) containing this polymorphic site. It was then possible to identify and analyze a larger number of polymorphism markers in the region of D16S3136, and also to define and study the transcribed sequences present in the region.

Example 2

Physical Mapping of the IBD1 Region

A contig of genomic DNA fragments, centered on the markers D16S3136, D16S3117, D16S770 and D16S416, was generated from the human genomic DNA libraries of the Jean Dausset foundation/CEPH. The chromosomal DNA segments were identified based on certain polymorphism markers used in fine genetic mapping (D16S411, D16S416, D16S541, D16S770, D16S2623, D16S3035, D16S3117 and D16S3136). For each marker, a bacterial artificial chromosome (BAC) library was screened by PCR so as to search for clones containing the marker sequence. Depending on whether or not the sequences tested were present on the BAC clones, it was then possible to organize the clones among one another using the Segmap software version 3.35.

It was possible to establish, for the BACs, a continuous organization (contig) covering the genetic region of interest, according to a method known to those skilled in the art (Rouquier et al., 1994; Kim et al., 1996; Asakawa et al., 1997). To do this, the ends of the BACs identified were sequenced and these new sequence data were then used to repeatedly screen the BAC libraries. At each screening, the BAC contig then progressed by a step until a continuum of overlapping clones was obtained. The size of each BAC contributing to the contig was deduced from its migration profile on a pulsed field agarose gel.

A BAC contig containing 101 BACs and extending over an overall distance of more than 2.5 Mb, with an average redundancy of 5.5 BACs at each point of the contig, was thus constructed. The average size of the BACs is 136 kb.

Example 3

Sequencing of BAC hb87b10

The BAC of this contig containing the polymorphism marker D16S3136 (called hb87b10), the size of which was 163761 bp, was sequenced according to the "shotgun" method. Briefly, the BAC DNA was fragmented by sonication. The DNA fragments thus generated were subjected to agarose gel electrophoresis and those with a size greater than 1.5 kb were eluted in order to be analyzed. These fragments were then cloned into the m13 phage, which was itself introduced into bacteria made competent, by electroporation. After culturing, the DNA of the clones was recovered and sequenced by automatic sequencing methods using fluorescent primers of the m13 vector on an automatic sequencer.

1526 different sequences with an average size of 600 bp were generated, which were organized with respect to one another using the Polyphredphrap® software, resulting in a sequence contig covering the entire BAC. The sequence thus generated had an average redundancy of 5.5 genomic equivalents. The rare (n=5) sequence gaps not represented in the m13 clone library were filled by generating specific PCR primers, on either side of these gaps, and analyzing the PCR product derived from the genomic DNA of a healthy individual.

Sequence homologies with sequences available in public genetic databases (Genbank) were sought No known gene could be identified in this region of 163 kb. Several ESTs were positioned, suggesting that unknown genes were contained in this sequence. These ESTs derived from the public genetic databases (Genbank, GDB, Unigene, dbEST) bore the following references: AI167910, AI011720, Rn24957, Mm30219, hs132289, AA236306, hs87296, AA055131, hs151708, AA417809, AA417810, hs61309, hs116424, HUMGS01037, AA835524, hs105242, SHGC17274, hs146128, hs122983, hs87280 and hs135201. The search for putative exons using the GRAIL computer program made it possible to identify several potential exons, polyadenylation sites and promoter sequences.

Example 4

Transmission Disequilibrium Studies 12 biallelic polymorphism markers (SNPs) were identified in a region extending over approximately 250 kb and centered on the BAC hb87b10. These polymorphisms were generated by analyzing the sequence of ten or so independent sick individuals suffering from CD. The sequencing was mostly carried out at known ESTs positioned on the BAC or in the region thereof. Putative exons, predicted by the GRAIL computer program, were also analyzed. The characteristics of the polymorphic markers thus identified are given in table 2.

the size of the products expected during typing (column VI)

199 families comprising 1 or more sick individuals suffering from CD were typed for these 12 polymorphism markers and also for the markers D16S3035 and D16S3136 located on the BAC hb87b10. The families comprising sick individuals suffering from UC were not taken into account. The methods for typing the polymorphisms studied were variable depending on the type of polymorphism, using:

the PCR-RFLP technique (amplification followed by enzymatic digestion of the PCR product) when the polymorphism was located on an enzymatic restriction site.

PCR with primers specific for the polymorphic site: differential amplification of two alleles using primers specific for each allele.

Oligoligation test: differential ligation using oligonucleotides specific for each allele, followed by polyacrylamide gel electrophoresis.

The typing data were then analyzed using a transmission disequilibrium test (TDT computer program of the GENE-HUNTER software version 2). For the families comprising several affected relatives, a single sufferer was taken into account for the analysis. In fact, if several related sufferers are taken into account, this poses the problem of nonindependence of the data in the statistical calculations and can induce an inflation of the value of the test. The sufferer used for the analysis was drawn by lots, within each family, using an automatic randomization procedure. Given this randomiza-

TABLE 2

Characteristics of biallelic polymorphism markers studied in the region of IBD1

| I | II | III | IV | V | VI |
|---|---|---|---|---|---|
| 1 | KIAA0849ex9 | AS-PCR | | SEQ ID No. 88 to 90 | 116 |
| 2 | hb27G11F | PCR-RFLP | BsrI | SEQ ID No. 86, 87 | 185 |
| | | | | | 116 |
| | | | | | 69 |
| 3 | Ctg22Ex1 | PCR-RFLP | RsaI | SEQ ID No. 84, 85 | 381 |
| | | | | | 313 |
| | | | | | 69 |
| 4 | SNP1 | AS-PCR | | SEQ ID No. 81 to 83 | 410 |
| 5 | ctg2931-3ac/ola | LO | | SEQ ID No. 78 to 80 | 51 |
| | | | | | 49 |
| 6 | ctg2931-5ag/ola | LO | | SEQ ID No. 75 to 77 | 44 |
| | | | | | 42 |
| 7 | SNP3-2931 | AS-PCR | | SEQ ID No. 72 to 74 | 245 |
| 8 | Ctg25Ex1 | PCR-RFLP | BsteII | SEQ ID No. 70, 71 | 207 |
| | | | | | 122 |
| | | | | | 85 |
| 9 | CTG35ExA | AS-PCR | | SEQ ID No. 67 to 69 | 333 |
| 10 | ctg35ExC | AS-PCR | | SEQ ID No. 64 to 66 | 198 |
| 11 | D1653136 | | | SEQ ID No. 37, 38 | |
| 12 | hb133D1f | PCR-RFLP | TaqI | SEQ ID No. 62, 63 | 369 |
| | | | | | 295 |
| | | | | | 74 |
| 13 | D16S3035 | | | SEQ ID No. 35, 36 | |
| 14 | ADCY7int7 | AS-PCR | | SEQ ID No. 59 to 61 | 140 |

AS-PCR: allele-specific PCR; LO: ligation of oligo-nucleotides

The 12 biallelic polymorphism markers newly described in this study are listed in this table. For each one of them, the following are indicated:

the locus (column I)
the name (column II)
the genotyping technique used (column III)
the restriction enzyme possibly used (column IV)
the oligonucleotide primers used for the polymerase chain reaction or for the ligation (column V)

tion, the value of the statistical test obtained represented only one possible sample derived from the group of families studied. So as not to limit the analysis to this one possible sample, and in order to understand more clearly the soundness of the results obtained, for each test, about one hundred random samples were thus generated and analyzed.

The markers were studied separately and then grouped according to their order on the chromosomal segment (KIAA0849ex9 (locus 1), hb27G11F (locus 2), Ctg22Ex1

(locus 3), SNP1 (locus 4), ctg2931-3ac/ola (locus 5), ctg2931-5ag/ola (locus 6), SNP3-2931 (locus 7), Ctg25Ex1 (locus 8), CTG35ExA (locus 9), ctg35ExC (locus 10), d16s3136 (locus 11), hb133D1f (locus 12), D16S3035 (locus 13), ADCY7int7 (locus 14)) (table 2). The haplotypes comprising 2, 3 and 4 consecutive markers were thus analyzed still using the same strategy (100 random samples, taking a single affected individual for each family).

For each sample tested, only the genotypes (or haplotypes) carried by at least 10 parental chromosomes were taken into account. On average, 250 different tests were thus carried out for each sample. It was then possible to deduce the number of tests expected to be positive for each significance threshold and to compare this distribution to the distribution observed. For the healthy individuals, the distribution of the tests is not different from that expected on a random basis ($\chi^2$=2.85, ddl=4, p=0.58). For the sick individuals, on the other hand, there is an excess of positive tests, reflecting the existence of a transmission disequilibrium in the region studied.

The results of the transmission disequilibrium test for each polymorphism marker taken separately or for the haplotypes showing the strongest transmission disequilibriums showed that the following markers and the disease are in linkage disequilibrium: Ctg22Ex1 (locus 3), SNP1 (locus 4), ctg2931-5ag/ola (locus 6), SNP3-2931 (locus 7), Ctg25Ex1 (locus 8) and ctg35ExC (locus 10). These markers extend over a region of approximately 50 kb (positions 74736 to 124285 on the sequence of hb87b10).

The haplotypes the most strongly associated with Crohn's disease themselves also extend over this region. Thus, for the majority of the random samples, the transmission test was positive (p<0.01) for haplotypes combining the following markers:

locus 5-6, locus 6-7, locus 7-8, locus 8-9, locus 9-10, locus 10-11 locus 5-6-7, locus 6-7-8, locus 7-8-9, locus 8-9-10, locus 9-10-11 locus 5-6-7-8, locus 6-7-8-9, locus 7-8-9-10.

The susceptibility haplotype most at risk is defined by the loci 7 to 10. This is the haplotype 1-2-1-2 (table 2).

The markers tested are, as expected, in linkage disequilibrium with respect to one another.

More recently, a new test, the Pedigree Disequilibrium Test (PDT), published in July 2000 (Martin et al., 2000), was used to understand more clearly the meaning of the results obtained with the TDT computer program. This new statistic in fact makes it possible to use all of the information available in a family, both from the sick individuals and from the healthy individuals, and to counterbalance the importance of each relative in an overall statistic for each family. The values of p corresponding to the PDT tests and obtained for an enlarged group of 235 families with one or more relatives suffering from Crohn's disease are given in table 3. This new analysis confirms that the region of the BAC hb87b10 is indeed associated with Crohn's disease.

TABLE 3

Results of the PDT tests carried out on 235 families suffering from Crohn's disease (NS: not significant)

| LOCUS | VALUE p OF THE PDT TEST |
|---|---|
| KIAA0849ex9 | NS |
| hb27g11f | 0.05 |
| ctg22ex1 | 0.01 |
| SNP1 | 0.001 |

TABLE 3-continued

Results of the PDT tests carried out on 235 families suffering from Crohn's disease (NS: not significant)

| LOCUS | VALUE p OF THE PDT TEST |
|---|---|
| ctg2931-3ac/ola | NS |
| ctg2931-5ag/ola | 0.0001 |
| SNP3-2931 | 0.0001 |
| ctg25ex1 | 0.0006 |
| ctg35exA | NS |
| ctg35exC | 0.00002 |
| D16S3136 | NS |
| hb133d1f | NS |
| D16S3035 | NS |

Example 5

Identification of the IBD1 Gene

The published EST groups (Unigene references: Hs 135201, Hs87280, Hs122983, Hs146128, Hs105242, Hs116424, Hs61309, Hs151708, Hs 87296 and Hs132289) present on the BAC hb87b10 were studied in the search for a more complete complementary DNA (cDNA) sequence. For IBD1prox, the clones available in public libraries were sequenced and the sequences were organized with respect to one another. For IBD1, a peripheral blood complementary DNA library (Stratagene human blood cDNA lambda zapexpress ref 938202) was screened with the PCR products generated from known ESTs according to the methods proposed by the manufacturer. The sequence of the cDNAs thus identified was then used for further screening of the cDNA library, and so on, until the presented cDNA was obtained.

The EST hs135201 (UniGene) made it possible to identify a cDNA not appearing on the available genetic databases (Genbank). It therefore corresponds to a new human gene. Comparison of the sequence of the cDNA and of the genomic DNA showed that this gene consists of 11 exons and 10 introns. An additional exon, positioned 5' to the cDNA identified, is predicted by analysis of the sequence with the Grail program. These exons are very homologous to the first exons of the CARD4/NOD1 gene. Taking into consideration all of the exons identified and the putative additional exon, this new gene appears to have a genomic structure very close to that of CARD4/NOD1. Moreover, a transcription initiation site appears upstream of the first putative exon. For all of these reasons, the putative exon was considered to contribute to this new gene. The cDNA reproduced in the annex (SEQ ID No. 1) therefore comprises all of the identified sequence plus the sequence predicted by the computer modeling, the complementary DNA beginning randomly at the first ATG codon of the predicted coding sequence. On this basis, the gene would therefore comprise 12 exons and 11 introns. The intron-exon structure of the gene is reported on SEQ ID No. 3.

The protein sequence deduced from the nucleotide sequence comprises 1041 amino acids (SEQ ID No. 2). This sequence has not been found on the biological databases either (Genpept, pir, swissprot).

Now, more recently, it has not been possible to confirm the putative exon described above. The IBD1 gene therefore effectively comprises only 11 exons and 10 introns and encodes a protein of 1013 amino acids (i.e. 28 amino acids less than initially determined).

Figure 3:
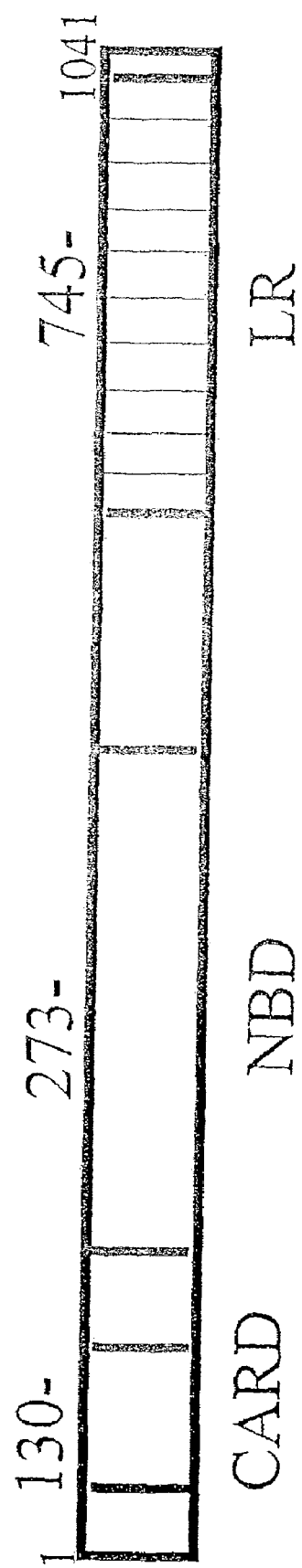
FIG. 3: Diagrammatic representation of the protein encoded by IBD1. The protein encoded by IBD1 is represented horizontally. The various domains of which it is composed are indicated on the figure with the amino acid reference number corresponding to the start and to the end of each domain. The protein consists of a CARD domain, a nucleotide-binding domain (NBD) and leucine-rich motifs (LRR).

The study of the deduced protein sequence shows that this gene contains three different functional domains (FIG. 3):

A CARD domain (Caspase Recruitment Domain) known to be involved in the interaction between proteins regulating apoptosis and activation of the NFkappa B pathway. The CARD domain makes it possible to classify this new protein in the CARD protein family, the most longstanding members of which are CED4, APAF1 and RICK.

An NBD domain (Nucleotide-Binding Domain) comprising an ATP-recognition site and a magnesium-binding site. The protein should therefore very probably have kinase activity.

An LRR domain (Leucine-Rich Domain) presumed to participate in the interaction between proteins, by analogy with other described protein domains.

Moreover, the LRR domain of the protein makes it possible to affiliate the protein to a family of proteins involved in intracellular signaling and present both in plants and in animals.

Comparison of this new gene with previously identified genes available in the public databases shows that this gene is very homologous to CARD4/NOD1 (Bertin et al., 1999; Inohara et al., 1999). This homology relates to the sequence of the complementary DNA, the intron-exon structure of the gene and the protein sequence. The sequence identity of the two complementary DNAs is 58%. A similarity is also observed at the level of the intron-exon structure. The sequence homology at the protein level is of the order of 40%.

The similarity between this new gene and CARD4/NOD1 suggests that, like CARD4/NOD1, the IBD1 protein is involved in the regulation of apoptosis and of the activation of NF-kappa B (Bertin et al., 1999; Inohara et al., 1999). The regulation of cellular apoptosis and activation of NF-kappa B are intracellular signaling pathways which are essential in immune reactions. Specifically, these signal translation pathways are the effector pathways of the proteins of the TNF (Tumor Necrosis Factor) receptor family involved in cell-cell interactions and the cellular response to the various mediators of inflammation (cytokines) The new gene therefore appears to be potentially important in the inflammatory reaction in general.

Several bodies of proof support bacteria induced deregulation of NF-κB in Crohn's disease. First of all, spontaneous susceptibility to IBD in mice has been associated with mutations in Tlr4, a molecule known to bind to LPS via its LRR domain (Poltorak et al., 1998 and Sundberg et al., 1994) and to be a member of the activators of the NF-kB family. Second, treatment with antibiotics causes a provisional improvement in patients suffering from CD, giving credit to the hypothesis that enteric bacteria may play an etiological role in Crohn's disease (McKay, 1999). Third, NF-kB plays a pivotal role in inflammatory bowel diseases and is activated in lamina propria mononuclear cells in Crohn's disease (Schreiber et al., 1998). Fourth, the treatment of Crohn's disease is based on the use of sulfasalazine and glucocorticoids, which are both known to be NF-kB inhibitors (Auphan et al., 1995 and Wahl et al., 1998).

Even more recently, it has been shown that the IBD1 candidate gene encodes a protein very similar to NOD2, a member of the CED4/APAF1 superfamily (Ogura et al., 2000). The nucleotide and protein sequences of IBD1 and NOD2 in reality only diverge for a small portion right at the start of the two reported sequences. The tissue expressions of Nod2 and IBD1 can, in addition, be superimposed. These two genes (proteins) can therefore be considered to be identical. It has been demonstrated that the LRR domain of Nod2 has binding activity for bacterial lipopolysaccharides (LPS) (Inohara et al., 2000) and that deletion thereof stimulates the NFkB pathway. This result confirms the data of the invention.

The tissue expression of IBD1 was then studied by Northern blotting. A 4.5 kb transcript is visible in most human tissues. The size of the transcript is in accordance with the size predicted by the cDNA. The 4.5 kb transcript appears to be very poorly abundant in the small intestine and the colon. It is, on the other hand, very strongly expressed in white blood cells. This is in agreement with clinical data on transplants which suggest that Crohn's disease is potentially a disease associated with circulating immune cells. In fact, bowel transplantation does not prevent recurrence on the transplant in Crohn's disease, whereas bone marrow transplantation appears to have a beneficial effect on the progression of the disease.

Certain data also call to mind alternative splicing, which may prove to be an important element in the possibility of generating mutants which may play a role in the development of inflammatory diseases.

The promoter of the IBD1 gene has not currently been identified with precision. It is, however, reasonable to think, by analogy with a very large number of genes, that this promoter lies, at least partly, immediately upstream of the gene, in the 5' portion thereof. This genetic region contains transcribed sequences, as witnessed by the presence of ESTs (HUMGS01037, AA835524, hs.105242, SHGC17274, hs.146128, hs.122983, hs.87280). The ATCC clones containing these sequences were sequenced and analyzed in the laboratory, making it possible to demonstrate an exon and intron organization with possible alternative splicings. These data suggest the existence of another gene (named IBD1prox due to its proximity to IBD1). The partial sequence of the complementary DNA of IBD1prox is reported (SEQ ID No. 4), as is its intron-exon structure, on SEQ ID No. 6.

Translation of the cDNAs corresponding to IBD1prox results in a protein containing a homeobox. Analysis of several cDNAs of the gene suggests, however, the existence of alternative splicings. IBD1prox, according to one of the possible alternative splicings, corresponds to the anonymous EST HUMGS01037, the RNA of which is expressed more strongly in differentiated leukocytic lines than in undifferentiated lines.

Thus, it is possible that this gene may have a role in inflammation and cell differentiation. It may therefore also, itself, be considered to be a good candidate for susceptibility to IBD. The association between CD and the polymorphism ctg35ExC located on the coding sequence of IBD1prox supports this hypothesis even though this polymorphism does not cause any sequence variation at the protein level.

Finally, more recently, the existence of a genetic linkage in families suffering from Crohn's disease and not comprising any mutation in the IBD1 gene also, itself, suggests that IBD1prox has a role in addition to IBD1 in genetic predisposition to the disease.

The functional relationship between IBD1 and IBD1prox is not currently established. However, the considerable proximity between the two genes may reflect an interaction between them. In this case, the "head-to-tail" location of these genes suggests that they may have common or interdependent methods of regulation.

Example 6

Identification of IBD1 Gene Mutations in Inflammatory Diseases

In order to confirm the role of IBD1 in inflammatory diseases, the coding sequence and the intron-exon junctions of the gene were sequenced from exon 2 to exon 12 inclusive, in 70 independent individuals, namely: 50 sick individuals suffering from CD, 10 sick individuals suffering from UC, 1 sick individual suffering from Blau's syndrome and 9 healthy controls. The sick individuals studied were mostly familial forms of the disease and were often carriers of the susceptibility haplotype defined by the transmission disequilibrium studies. The healthy controls were of Caucasian origin.

It was thus possible to identify 24 sequence variants on this group of 70 unrelated individuals (table 3).

The nomenclature of the mutations reported refers to the initial sequence of the protein comprising 1 041 amino acids. The more recently proposed nomenclature is easily deduced by removing 28 amino acids from the initial sequence, and therefore corresponds to a protein comprising 1 013 amino acids (cf. example 5).

TABLE 4

Mutations observed in the IBD1 gene

| Exon | Nucleotide variant | Protein variant | Crohn's disease | Ulcerative colitis | Health controls |
|---|---|---|---|---|---|
| 1 | Not tested | | | | |
| 2 | G417A | Silent | | | |
| 2 | C537G | Silent | | | |
| 3 | None | | | | |
| 4 | T805C | S269P | 48/100 | 6/20 | 3/18 |
| 4 | A869G | N290S | 0 | 0 | 1/18 |
| 4 | C905T | A302V | 1/100 | 0 | 0 |
| 4 | C1283T | P428L | 1/100 | 0 | 0 |
| 4 | C1284A | Silent | | | |
| 4 | C1287T | Silent | | | |
| 4 | T1380C | Silent | | | |
| 4 | T1764G | Silent | | | |
| 4 | G1837A | A613T | 1/100 | 0 | 0 |
| 4 | C2107T | R703W | 10/10 | 1/20 | 1/18 |
| 4 | C2110T | R704C | 4/10 | 1/20 | 0 |
| 5 | G2365A | R792Q | 1/100 | 0 | 0 |
| 5 | G2370A | V794M | 0 | 1/20 | 0 |
| 5 | G2530A | E844K | 1/10 | 0 | 0 |
| 6 | A2558G | N853S | 1/100 | 0 | 0 |
| 6 | A2590G | M864V | 1/100 | 0 | 0 |
| 7 | None | | | | |
| 8 | G2725C | G909R | 7/100 | 0 | 0 |
| 8 | C2756A | A919D | 1/100 | 0 | 0 |
| 9 | G2866A | V956I | 2/100 | 1/20 | 3/18 |
| 10 | C2928T | Silent | | | |
| 11 | 3022insC | Stop | 20/100 | 0 | 0 |
| 12 | none | | | | |

The mutations other than silent mutations observed in each exon are reported. They are indicated by the variation in the peptide chain. For each mutation and for each phenotype studied, the number of times where the mutation is observed, related to the number of chromosomes tested, is indicated.

No functional sequence variant was identified in exons 1 to 3 (corresponding to the CARD domain of the protein). Exons 7 and 12 did not show any sequence variation either. Certain variants corresponded to polymorphisms already identified and typed for transmission disequilibrium studies, namely:

Snp3-2931: nucleotide variant T805C, protein variant S269P ctg2931-5ag/ola: nucleotide variant T1380C (silent)

ctg2931-3ac/ola: nucleotide variant T1746G (silent)

SNP1: nucleotide variant C2107T, protein variant R703W.

Several sequence variations were silent (G417A, C537G, C1284A, C1287T, T1380C, T1764G and C2928T) and did not lead to any modification of the protein sequence. They were not studied further here.

For the 16 non-silent sequence variations, protein sequence variants were observed in 43/50 CD versus 5/9 healthy controls, and 6/10 UC. The existence of one or more sequence variation(s) appeared to be associated with the CD phenotype. Several sequence variations often existed in the same individual suffering from CD, suggesting a sometimes recessive effect of the gene for CD. On the other hand, no composite heterozygote or homozygote was observed among the patients suffering from UC or among the healthy controls.

Some non-silent variants were present both in the sick individuals suffering from UC or from CD and in the healthy individuals. They were the variants S269P, N290S, R703W and V956I located in exons 2, 4 and 9. Further information therefore appears to be necessary before selecting a possible functional role for these sequence variants.

V956I is a conservative sequence variation (aliphatic amino acids).

The sequence variant S269P corresponds to a variation in amino acid class (hydroxylated to immuno acid) at the beginning of the nucleotide-binding domain. This sequence variant and CD are in transmission disequilibrium. It is in fact the polymorphism Snp3 (cf. above).

R703W results in a modification of the amino acid class (aromatic instead of basic). This modification occurs in the intermediate region between the NBD and LRR domains, which is a region conserved between IBD1 and CARD4/NOD1. A functional role may therefore be suspected for this polymorphism. This sequence variation (corresponding to the polymorphic site Snp1) is transmitted to sick individuals suffering from CD more often than at random (cf. above), confirming that this polymorphism is associated with CD. It is possible that the presence of this mutant in healthy individuals reflects incomplete penetration of the mutation as is expected for complex genetic diseases such as chronic inflammatory bowel diseases.

The variant R704C, located immediately next to R703W, could be identified in both CD and UC. It also, itself, corresponds to a nonconservative variation of the protein (sulfur-containing amino acid instead of basic amino acid) on the same protein region, suggesting a functional effect for R704C which is as important as that for R703W.

Other sequence variations are specific for CD, for UC or for Blau's syndrome.

Some sequence variations are, on the contrary, rare, present in one or a few sick individuals (A613T, R704C, E844K, N853S, M864V, A919D). They are always variations leading to nonconservative modifications of the protein in leucine-rich domains, at positions which are important within these domains. These various elements suggest that these variations have a functional role.

Two sequence variations (G909R and L1008P*) are found in quite a large number of Crohn's diseases (respectively 7/50 and 16/50) whereas they are not detected in the controls or in the individuals suffering from UC.

The deletion/insertion of a guanosine at codon 1008 results in transformation of the third leucine of the alpha helix of the last LRR to proline followed by a STOP codon (L1008P*). This sequence variation therefore leads to an important modification of the protein: decrease in size of the protein (protein having a truncated LRR domain) and modification of a very conserved amino acid (leucine). This sequence modification is associated with CD, as witnessed by a transmission disequilibrium study in 16 families carrying the mutation (P=0.008).

The mutation G909R occurs on the last amino acid of the sixth LRR motif. It replaces an aliphatic amino acid with a basic amino acid. This variation is potentially important given the usually neutral or polar nature of the amino acids in the terminal position of the leucine-rich motifs (both for IBD1 and for NOD1/CARD4) and the conserved nature of this amino acid on the IBD1 and NOD1/CARD4 proteins.

In Blau's syndrome, the sick individuals (n=2) of the family studied carried a specific sequence variation (L470F) located in exon 4 and corresponding to the NBD domain of the protein. In this series, this sequence variant was specific for Blau's syndrome.

In UC, several sequence variants not found in healthy individuals were also identified. The proportion of sick individuals carrying a mutation was smaller than for CD, as expected given the less strongly established linkage between IBD1 and UC, and the supposedly less genetic nature of the latter disease. Sequence variations were common to CD and to UC (R703W, R704C). Others, on the other hand, appeared to be specific for UC (V794M). This observation makes it possible to confirm that CD and UC are diseases which, at least partly, share the same genetic predisposition. It lays down the foundations of a nosological classification for IBDs.

The study of the sequence variants of the IBD1 gene has therefore made it possible to identify several variants having a very probable functional effect (for example: truncated protein) and associated with Crohn's disease, with UC and with Blau's syndrome.

The promoter of the gene is not currently determined. In all probability, however, it is likely to be located in the 5' region upstream of the gene. According to this hypothesis, the sequence variants observed in this region may have a functional effect. This may explain the very strong association between CD and certain polymorphic loci, such as ctg35ExC or Ctg25Ex1.

The invention thus provides the first description of mutations in the family of genes containing a CARD domain in humans. The frequency of these mutations in various inflammatory diseases shows that the IBD1 gene has an essential role in normal and pathological inflammatory processes. This invention provides new paths of understanding and of research in the field of the physiopathology of normal and pathological inflammatory processes. As a result, it makes it possible to envision the development of new pharmaceutical molecules which regulate the effector pathways controlled by IBD1 and which are useful in the treatment of inflammatory diseases and in the regulation of inflammatory processes in general.

Example 7

Bases for a Biological Diagnosis of Susceptibility to Crohn's Disease

More recently, 457 independent patients suffering from Crohn's disease, 159 independent patients suffering from ulcerative colitis and 103 healthy controls were studied in the search for mutations. This study made it possible to confirm the mutations previously reported and to identify additional mutations, reported in FIG. 4. The main mutations were then genotyped in 235 families suffering from Crohn's disease. This more recent study is reported using, as reference, the shorter protein sequence (1 013 amino acids, see example 5), but the prior nomenclature for the mutations is easily deduced from the latter by adding 28 to the number indicating the position of the amino acids.

Among the 5 most common mutations, the conservative mutation V928I (formerly V956I) is not significantly associated with one or the other of the inflammatory bowel diseases, and does not therefore appear to have an important role in the disease.

The mutation S241P (formerly S269P) is in linkage disequilibrium with the other main mutations and does not appear to play an important role, by itself, in susceptibility to inflammatory bowel diseases (data not shown).

Figure 4:
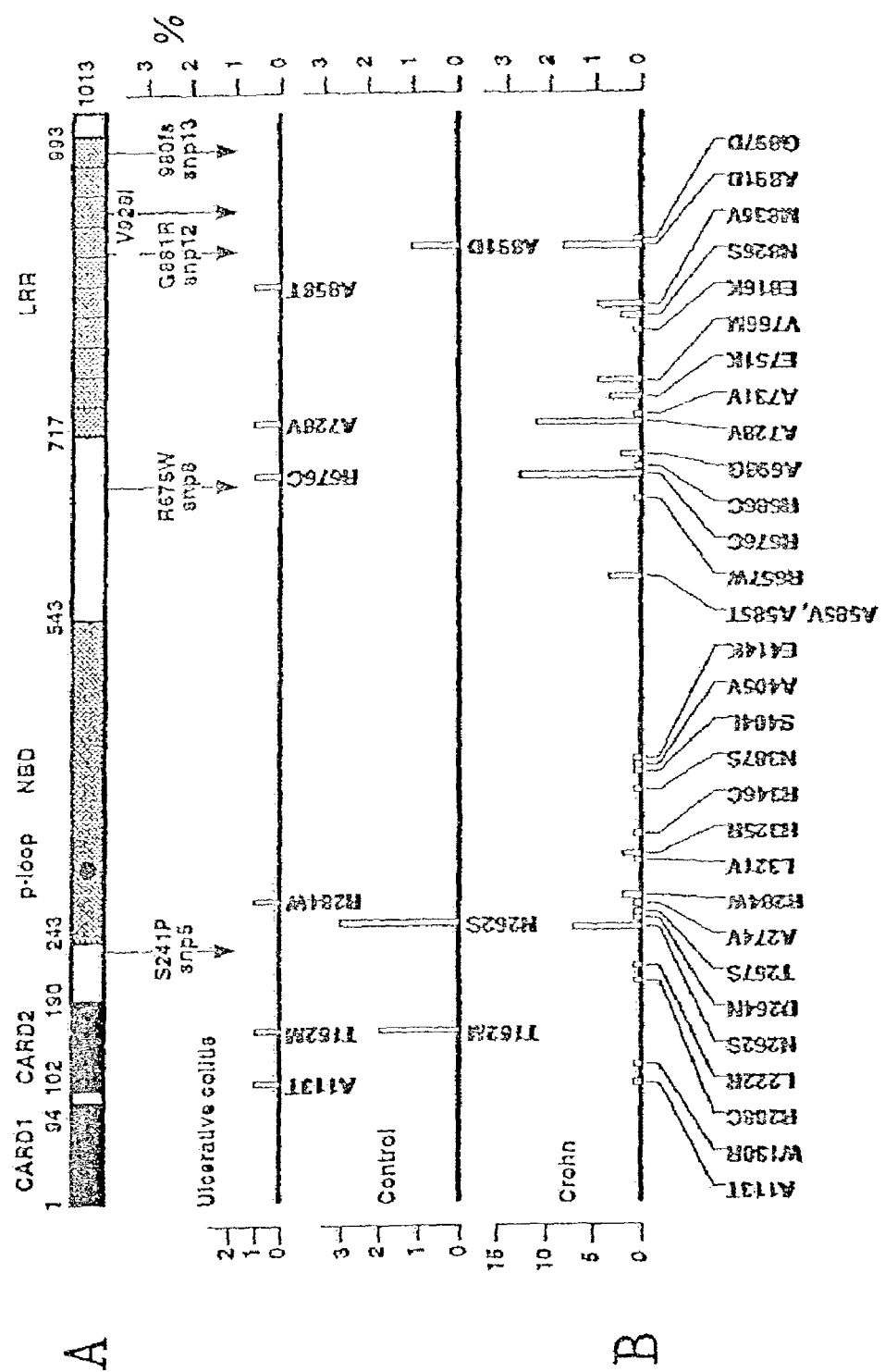
FIG. 4: Diagrammatic representation of the IBD1/NOD2 protein in three variants associated with CD.

Conversely, the other 3 mutations, R675W (formerly R703W), G881R (formerly G909R) and 980fs (formerly L1008P), are significantly associated with Crohn's disease but not with ulcerative colitis (cf. below). The location in the LRR, or in its immediate proximity, of the 3 common mutations pleads very strongly in favor of a functional mechanism involving this protein domain, probably via a defect in negative regulation of NFkB by the mutated protein. The other mutations are more rare (FIG. 4). These cumulative mutations are present in 17% of the individuals suffering from Crohn's disease versus, respectively, 4% and 5% of the healthy individuals or individuals suffering from ulcerative colitis. A large number of rare mutations are also located in the LRR.

The intrafamily studies of the three polymorphisms most common in Crohn's disease show that all three are associated with the disease (table 5). As expected, for a mutation supposed to be very deleterious, the polymorphism most strongly associated is the truncating mutation. These three polymorphisms are independently associated with Crohn's disease, since it was not possible to identify, on 235 families, chromosomes carrying more than one of these three mutations. The independent nature of these associations considerably supports the hypothesis that the IBD1 gene is clearly involved in genetic predisposition to Crohn's disease.

TABLE 5

Study of the 3 common polymorphisms of IBD1 in 235 families suffering from Crohn's disease

| MUTATION | VALUE p OF THE PDT TEST |
|---|---|
| R675W | 0.001 |
| G881R | 0.003 |
| 980fs | 0.000006 |

The case-control studies confirm this association (table 6). They show that the mutations most common in Crohn's disease are not common in ulcerative colitis.

TABLE 6

Case-control study of the 3 common polymorphisms of IBD1 in inflammatory bowel diseases

| MUTATION | No. OF CHROMO-SOMES STUDIED | FREQUENCY OF THE ALLELE AT RISK R675W | FREQUENCY OF THE ALLELE AT RISK G881R | FREQUENCY OF THE ALLELE AT RISK 980fs | TOTAL ALLELES AT RISK |
|---|---|---|---|---|---|
| Healthy controls | 206 | 0.04 | 0.01 | 0.02 | 0.07 |
| Ulcerative colitis | 318 | 0.03 | 0.00 | 0.01 | 0.05 |
| Crohn's disease | 936 | 0.11 | 0.06 | 0.12 | 0.29 |

The study of the dose-effect of these mutations shows that individuals carrying a mutation in the homozygous or composite heterozygous state exhibit a much greater risk of developing the disease than individuals who are not carrying or are heterozygous for these mutations (table 7).

TABLE 7

Relative and absolute risk of Crohn's disease attributable as a function of the genotype of IBD1 In the general population, a risk of Crohn's disease of 0.001 has been taken as a reference, and it has been presumed that the mutations are in Hardy-Weinberg equilibrium.

| Distribution | GENOTYPE | | | |
|---|---|---|---|---|
| | No VARIANT | SIMPLE HETEROZYGOTE | HOMOZYGOTE | COMPOSITE HETEROZYGOTE |
| Healthy | 88 | 15 | 0 | 0 |
| Ulcerative colitis | 145 | 13 | 1 | 0 |
| Crohn's disease | 267 | 133 | 20 | 40 |
| Attributable risk of CD: | | | | |
| Relative risk | 1 | 3 | 38 | 44 |
| Absolute risk | 0.0007 | 0.002 | 0.03 | 0.03 |

The studies mentioned above confirm the prior preliminary data and provide the detailed bases for a biological diagnosis of Crohn's disease by studying the IBD1 variants. In fact, this work:

1) defines the mutations, the frequency of which is greater than 0.001 in a mixed Caucasian population;
2) defines the frequency of the mutations observed and makes it possible to define 3 main mutations associated with Crohn's disease. Thus, it is possible, by virtue of this work, to define a strategy for studying the gene in order to search for morbid variants, namely: firstly, typing the 3 main mutations; secondly, searching for mutations in the last 7 exons; thirdly, searching for other sequence variants;
3) defines the practical modalities for searching for these mutations by pointing out their position and their nature. In fact, it is then easy for those skilled in the art to develop typing and sequencing methods according to their personal expertise. Mention may in particular be made of the possibility of genotyping the three main mutations by PCR followed by enzymatic digestion and electrophoresis, study of the migration profiles by dHPLC, DGGE or SSCP, oligoligation, microsequencing, etc.;
4) demonstrates the independence of the most common mutations which are not observed on the same chromosome in this extended and varied population. This information makes it possible to reliably classify the individuals who are composite heterozygotes (having two mutations) as carriers with a double dose of intragenic variations;
5) demonstrates that the great majority of the mutations only lead to a null or minimal effect on the risk of ulcerative colitis. This result makes it possible to envision assisting the clinician in the differential diagnosis between these two diseases. In fact, in approximately 10% of cases, inflammatory bowel diseases remain unclassified despite biological, radiological and endoscopic examination;
6) defines a relative and absolute risk of disease for the most common genotypes. This result lays down the foundations of a predictive diagnosis potentially useful in an approach of preventive monitoring and intervention in populations at risk, in particular the relatives of sick individuals;
7) demonstrates the existence of a dose-effect for the IBD1 gene and confirms the partly recessive nature of genetic predisposition to Crohn's disease. It therefore makes it possible to lay the foundations for genetic counseling and for intra-familial preclinical diagnosis.

Finally, it should be noted that an additional mutation of the NBD domain was isolated in a second family carrying Blau's syndrome. The rareness of the two events in 2 different families is sufficient to confirm the involvement of this gene in Blau's syndrome and in granulomatous diseases in general.

All of these data provide a diagnostic tool which is directly applicable and of use to the practitioner in his or her daily practice.

The IBD1prox gene, located in the promoter region of IBD1, and the partial sequence of which is disclosed in the present invention, may also, itself, have an important role in the regulation of cellular apoptosis and of the inflammatory process, as suggested by its differential expression in mature cells of the immune system. The strong association reported in this work between the polymorphism marker ctg35ExC (located in the transcribed region of the gene) and Crohn's disease also pleads very strongly in favor of this hypothesis.

Inflammatory bowel diseases are complex genetic diseases for which, until now, no susceptibility gene had been identified with certainty. The invention has made it possible to identify the first gene for susceptibility to Crohn's disease, using a positional cloning (or reverse genetics) approach. This is the first genetic location obtained using such an approach for a complex genetic disease, which demonstrates its usefulness and its feasibility, at least in certain cases in complex genetic diseases.

The present invention also relates to a purified or isolated nucleic acid, characterized in that it encodes a polypeptide possessing a continuous fragment of at least 200 amino acids of a protein chosen from SEQ ID No. 2 and SEQ ID No. 5.

REFERENCES

Auphan et al. (1995), Science 270, 286-90.
Asakawa et al. (1997), Gene, 191, 69.
Becker et al. (1998), Proc. Natl. Acad. Sci. USA, 95, 9979.
Bertin et al. (1999), J. Biol. Chem., 274, 12955.
Buckholz (1993), Curr. Op. Biotechnology 4, 538.
Carter, (1993), Curr. Op. Biotechnology 3, 533.
Cho et al. (1998), Proc. Natl. Acad. Sci. USA, 95, 7502.
Duck et al. (1990), Biotechniques, 9, 142.
Edwards and Aruffo (1993), Curr. Op. Biotechnology, 4, 558.
Epstein (1992), Médecine/Sciences, 8, 902.
Guatelli et al. (1990), Proc. Natl. Acad. Sci. USA 87: 1874.
Hugot et al. (1996), Nature, 379, 821.
Inohara et al. (1999), J. Biol. Chem., 274, 14560.
Inohara et al. (2000), J. Biol. Chem.
Kievitis et al. (1991), J. Virol. Methods, 35, 273.
Kim et al. (1996), Genomics, 34, 213.
Köhler and Milstein (1975), Nature, 256, 495.
Kwoh et al. (1989), Proc. Natl. Acad. Sci. USA, 86, 1173.
Landegren et al. (1988), Science 241, 1077.
Lander and Kruglyak (1995), Nat. Genet., 11, 241.
Luckow (1993), Curr. Op. Biotechnology 4, 564.
Martin et al. (2000), Am. J. Hum. Genet. 67: 146-54.
Matthews et al. (1988), Anal. Biochem., 169, 1-25.
McKay (1999), Gastroenterol. 13, 509-516.
Miele et al. (1983), J. Mol. Biol., 171, 281.
Neddleman and Wunsch (1970), J. Mol. Biol. 48: 443.
Ogura et al. (2000), J. Biol. Chem.
Olins and Lee (1993), Curr. Op. Biotechnology 4: 520.
Perricaudet et al. (1992), La Recherche 23: 471.
Pearson and Lipman (1988), Proc. Natl. Acad. Sci. USA 85: 2444.
Poltorak et al. (1998), Sciences 282, 2085-8.
Rioux et al. (1998), Gastroenterology, 115: 1062.
Rohlmann et al. (1996), Nature Biotech. 14: 1562.
Rolfs, A. et al., (1991), Berlin: Springer-Verlag.
Rouquier et al. (1994), Anal. Biochem. 217, 205.
Sambrook et al. (1989), Molecular cloning: a laboratory manual, 2nd ed. Cold Spring Harbor Lab., Cold Spring Harbor, N.Y.
Satsangi et al. (1996), Nat. Genet., 14: 199.
Schreiber et al. (1998), Gut 42, 477-84.
Segev (1992), Kessler C. Springer Verlag, Berlin, N.Y., 197-205.
Smith and Waterman (1981) Ad. App. Math. 2: 482.
Steward and Yound (1984), Solid phase peptides synthesis, Pierce Chem. Company, Rockford, Ill, 2nd ed. (1984).
Spielman et al. (1993), Am. J. Hum. Genet., 52, 506.
Sundberg et al. (1994), Gastroenterology, 107, 1726-35.
Temin (1986), Retrovirus vectors for gene transfer. In Kucherlapati R., ed. Gene Transfer, New York, Plenum Press, 149-187.
Tromp et al. (1996), Am. J. Hum. Genet., 59: 1097.
Wahl et al. (1998), B. J. Clin. Invest 101, 1163-74.
Walker (1992), Nucleic Acids Res. 20: 1691.

The invention claimed is:

1. A purified or isolated nucleic acid, comprising the nucleic acid sequence selected from the group of sequences consisting of:
   a) SEQ ID NO:1 or SEQ ID NO:3;
   b) the complete complementary sequence of SEQ ID NO:1 or SEQ ID NO:3; and
   c) the RNA sequence corresponding to SEQ ID NO:1 or SEQ ID NO:3.

2. The purified or isolated nucleic acid as claimed in claim 1, comprising a) SEQ ID NO:1, or b) the complete complementary sequence of SEQ ID NO:1 or c) the RNA sequence corresponding to SEQ ID NO:1.

3. An expression vector, comprising the nucleic acid of claim 1.

4. An isolated host cell transformed with the vector of claim 3.

5. A method of producing a polypeptide encoded by the nucleic acid of claim 1, said method comprising culturing a host cell transformed with a vector comprising said nucleic acid under conditions allowing expression of said polypeptide; and recovering said expressed polypeptide from said host cell culture.

6. A purified or isolated polypeptide produced by the method of claim 5.

7. The purified or isolated nucleic acid as claimed in claim 1, comprising SEQ ID NO:3.

8. An isolated polypeptide, comprising the polypeptide set forth in SEQ ID NO:2.

9. The polypeptide as claimed in claim 8, consisting of SEQ ID NO:2.

10. A method of diagnosing Crohn's disease in a subject, said method comprising:

a) contacting a biological specimen from said subject with a nucleic acid probe specific for a variant nucleic acid sequence selected from the group consisting of SEQ ID NO:3 having a C to T mutation at nucleotide 16467, SEQ ID NO:3 having a G to C mutation at nucleotide 27059, and SEQ ID NO:3 having a C insertion at nucleotide 34296;
   b) determining the presence of said variant nucleic acid sequence by detecting hybridization between said nucleic acid probe and said variant nucleic acid sequence; and
   c) associating the presence of said variant nucleic acid sequence with a diagnosis of Crohn's disease in said subject.

11. The method as claimed in claim 10, wherein said nucleic acid probe comprises a detectable label.

12. The method as claimed in claim 11, wherein said detectable label is a fluorescent label.

13. A purified or isolated nucleic acid comprising SEQ ID NO:1, wherein nucleotide 2107 has a C to T mutation.

14. A purified or isolated nucleic acid comprising SEQ ID NO: 1, wherein nucleotide 2725 has a G to C mutation.

15. A purified or isolated nucleic acid comprising SEQ ID NO: 1, wherein nucleotide 3022 has a C insertion.

16. An isolated polypeptide comprising SEQ ID NO:2, wherein amino acid 703 has a R to W substitution.

17. An isolated polypeptide comprising SEQ ID NO:2, wherein amino acid 909 has a G to R substitution.

18. An isolated polypeptide comprising amino acids 1-1008 of SEQ ID NO:2, wherein amino acid 1008 has a L to P substitution.

* * * * *

UNITED STATES PATENT AND TRADEMARK OFFICE
CERTIFICATE OF CORRECTION

| | | |
|---|---|---|
| PATENT NO. | : 7,592,437 B2 | Page 1 of 1 |
| APPLICATION NO. | : 10/240046 | |
| DATED | : September 22, 2009 | |
| INVENTOR(S) | : Hugot et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 734 days Delete the phrase "by 734 days" and insert -- by 1278 days --

Signed and Sealed this

Twentieth Day of July, 2010

David J. Kappos
*Director of the United States Patent and Trademark Office*

SEQUENCE LISTING

```
<160> NUMBER OF SEQ ID NOS: 90

<210> SEQ ID NO 1
<211> LENGTH: 4322
<212> TYPE: DNA
<213> ORGANISM: Homo sapiens
<220> FEATURE:
<221> NAME/KEY: CDS
<222> LOCATION: (1)..(3123)

<400> SEQUENCE: 1 atg gag aag aga agg ggt cta acc att gag tgc tgg ggc ccc caa agt      48
Met Glu Lys Arg Arg Gly Leu Thr Ile Glu Cys Trp Gly Pro Gln Ser
 1               5                  10                  15 ccc tca ctg acc ttg ttc tcc tcc cca ggt tgt gaa atg tgc tcg cag      96
Pro Ser Leu Thr Leu Phe Ser Ser Pro Gly Cys Glu Met Cys Ser Gln
             20                  25                  30 gag gct ttt cag gca cag agg agc cag ctg gtc gag ctg ctg gtc tca     144
Glu Ala Phe Gln Ala Gln Arg Ser Gln Leu Val Glu Leu Leu Val Ser
         35                  40                  45 ggg tcc ctg gaa ggc ttc gag agt gtc ctg gac tgg ctg ctg tcc tgg     192
```

```
                Gly Ser Leu Glu Gly Phe Glu Ser Val Leu Asp Trp Leu Leu Ser Trp
                     50                  55                  60 gag gtc ctc tcc tgg gag gac tac gag ggc ttc cac ctc ctg ggc cag                240
Glu Val Leu Ser Trp Glu Asp Tyr Glu Gly Phe His Leu Leu Gly Gln
 65                  70                  75                  80 cct ctc tcc cac ttg gcc agg cgc ctt ctg gac acc gtc tgg aat aag                288
Pro Leu Ser His Leu Ala Arg Arg Leu Leu Asp Thr Val Trp Asn Lys
                 85                  90                  95 ggt act tgg gcc tgt cag aag ctc atc gcg gct gcc caa gaa gcc cag                336
Gly Thr Trp Ala Cys Gln Lys Leu Ile Ala Ala Ala Gln Glu Ala Gln
            100                 105                 110 gcc gac agc cag tcc ccc aag ctg cat ggc tgc tgg gac ccc cac tcg                384
Ala Asp Ser Gln Ser Pro Lys Leu His Gly Cys Trp Asp Pro His Ser
        115                 120                 125 ctc cac cca gcc cga gac ctg cag agt cac cgg cca gcc att gtc agg                432
Leu His Pro Ala Arg Asp Leu Gln Ser His Arg Pro Ala Ile Val Arg
    130                 135                 140 agg ctc cac agc cat gtg gag aac atg ctg gac ctg gca tgg gag cgg                480
Arg Leu His Ser His Val Glu Asn Met Leu Asp Leu Ala Trp Glu Arg
145                 150                 155                 160 ggt ttc gtc agc cag tat gaa tgt gat gaa atc agg ttg ccg atc ttc                528
Gly Phe Val Ser Gln Tyr Glu Cys Asp Glu Ile Arg Leu Pro Ile Phe
                165                 170                 175 aca ccg tcc cag agg gca aga agg ctg ctt gat ctt gcc acg gtg aaa                576
Thr Pro Ser Gln Arg Ala Arg Arg Leu Leu Asp Leu Ala Thr Val Lys
            180                 185                 190 gcg aat gga ttg gct gcc ttc ctt cta caa cat gtt cag gaa tta cca                624
Ala Asn Gly Leu Ala Ala Phe Leu Leu Gln His Val Gln Glu Leu Pro
        195                 200                 205 gtc cca ttg gcc ctg cct ttg gaa gct gcc aca tgc aag aag tat atg                672
Val Pro Leu Ala Leu Pro Leu Glu Ala Ala Thr Cys Lys Lys Tyr Met
    210                 215                 220 gcc aag ctg agg acc acg gtg tct gct cag tct cgc ttc ctc agt acc                720
Ala Lys Leu Arg Thr Thr Val Ser Ala Gln Ser Arg Phe Leu Ser Thr
225                 230                 235                 240 tat gat gga gca gag acg ctc tgc ctg gag gac ata tac aca gag aat                768
Tyr Asp Gly Ala Glu Thr Leu Cys Leu Glu Asp Ile Tyr Thr Glu Asn
                245                 250                 255 gtc ctg gag gtc tgg gca gat gtg ggc atg gct gga tcc ccg cag aag                816
Val Leu Glu Val Trp Ala Asp Val Gly Met Ala Gly Ser Pro Gln Lys
            260                 265                 270 agc cca gcc acc ctg ggc ctg gag gag ctc ttc agc acc cct ggc cac                864
Ser Pro Ala Thr Leu Gly Leu Glu Glu Leu Phe Ser Thr Pro Gly His
        275                 280                 285 ctc aat gac gat gcg gac act gtg ctg gtg gtg ggt gag gcg ggc agt                912
Leu Asn Asp Asp Ala Asp Thr Val Leu Val Val Gly Glu Ala Gly Ser
    290                 295                 300 ggc aag agc acg ctc ctg cag cgg ctg cac ttg ctg tgg gct gca ggg                960
Gly Lys Ser Thr Leu Leu Gln Arg Leu His Leu Leu Trp Ala Ala Gly
305                 310                 315                 320 caa gac ttc cag gaa ttt ctc ttt gtc ttc cca ttc agc tgc cgg cag                1008
Gln Asp Phe Gln Glu Phe Leu Phe Val Phe Pro Phe Ser Cys Arg Gln
                325                 330                 335 ctg cag tgc atg gcc aaa cca ctc tct gtg cgg act cta ctc ttt gag                1056
Leu Gln Cys Met Ala Lys Pro Leu Ser Val Arg Thr Leu Leu Phe Glu
            340                 345                 350 cac tgc tgt tgg cct gat gtt ggt caa gaa gac atc ttc cag tta ctc                1104
His Cys Cys Trp Pro Asp Val Gly Gln Glu Asp Ile Phe Gln Leu Leu
        355                 360                 365
```

```
                                           -continued
ctt gac cac cct gac cgt gtc ctg tta acc ttt gat ggc ttt gac gag    1152
Leu Asp His Pro Asp Arg Val Leu Leu Thr Phe Asp Gly Phe Asp Glu
    370                 375                 380 ttc aag ttc agg ttc acg gat cgt gaa cgc cac tgc tcc ccg acc gac    1200
Phe Lys Phe Arg Phe Thr Asp Arg Glu Arg His Cys Ser Pro Thr Asp
385                 390                 395                 400 ccc acc tct gtc cag acc ctg ctc ttc aac ctt ctg cag ggc aac ctg    1248
Pro Thr Ser Val Gln Thr Leu Leu Phe Asn Leu Leu Gln Gly Asn Leu
                405                 410                 415 ctg aag aat gcc cgc aag gtg gtg acc agc cgt ccg gcc gct gtg tcg    1296
Leu Lys Asn Ala Arg Lys Val Val Thr Ser Arg Pro Ala Ala Val Ser
        420                 425                 430 gcg ttc ctc agg aag tac atc cgc acc gag ttc aac ctc aag ggc ttc    1344
Ala Phe Leu Arg Lys Tyr Ile Arg Thr Glu Phe Asn Leu Lys Gly Phe
            435                 440                 445 tct gaa cag ggc atc gag ctg tac ctg agg aag cgt cat cat gag ccc    1392
Ser Glu Gln Gly Ile Glu Leu Tyr Leu Arg Lys Arg His His Glu Pro
    450                 455                 460 ggg gtg gcg gac cgc ctc atc cgc ctg ctc caa gag acc tca gcc ctg    1440
Gly Val Ala Asp Arg Leu Ile Arg Leu Leu Gln Glu Thr Ser Ala Leu
465                 470                 475                 480 cac ggt ttg tgc cac ctg cct gtc ttc tca tgg atg gtg tcc aaa tgc    1488
His Gly Leu Cys His Leu Pro Val Phe Ser Trp Met Val Ser Lys Cys
                485                 490                 495 cac cag gaa ctg ttg ctg cag gag ggg ggg tcc cca aag acc act aca    1536
His Gln Glu Leu Leu Leu Gln Glu Gly Gly Ser Pro Lys Thr Thr Thr
            500                 505                 510 gat atg tac ctg ctg att ctg cag cat ttt ctg ctg cat gcc acc ccc    1584
Asp Met Tyr Leu Leu Ile Leu Gln His Phe Leu Leu His Ala Thr Pro
        515                 520                 525 cca gac tca gct tcc caa ggt ctg gga ccc agt ctt ctt cgg ggc cgc    1632
Pro Asp Ser Ala Ser Gln Gly Leu Gly Pro Ser Leu Leu Arg Gly Arg
    530                 535                 540 ctc ccc acc ctc ctg cac ctg ggc aga ctg gct ctg tgg ggc ctg ggc    1680
Leu Pro Thr Leu Leu His Leu Gly Arg Leu Ala Leu Trp Gly Leu Gly
545                 550                 555                 560 atg tgc tgc tac gtg ttc tca gcc cag cag ctc cag gca gca cag gtc    1728
Met Cys Cys Tyr Val Phe Ser Ala Gln Gln Leu Gln Ala Ala Gln Val
                565                 570                 575 agc cct gat gac att tct ctt ggc ttc ctg gtg cgt gcc aaa ggt gtc    1776
Ser Pro Asp Asp Ile Ser Leu Gly Phe Leu Val Arg Ala Lys Gly Val
            580                 585                 590 gtg cca ggg agt acg gcg ccc ctg gaa ttc ctt cac atc act ttc cag    1824
Val Pro Gly Ser Thr Ala Pro Leu Glu Phe Leu His Ile Thr Phe Gln
        595                 600                 605 tgc ttc ttt gcc gcg ttc tac ctg gca ctc agt gct gat gtg cca cca    1872
Cys Phe Phe Ala Ala Phe Tyr Leu Ala Leu Ser Ala Asp Val Pro Pro
    610                 615                 620 gct ttg ctc aga cac ctc ttc aat tgt ggc agg cca ggc aac tca cca    1920
Ala Leu Leu Arg His Leu Phe Asn Cys Gly Arg Pro Gly Asn Ser Pro
625                 630                 635                 640 atg gcc agg ctc ctg ccc acg atg tgc atc cag gcc tcg gag gga aag    1968
Met Ala Arg Leu Leu Pro Thr Met Cys Ile Gln Ala Ser Glu Gly Lys
                645                 650                 655 gac agc agc gtg gca gct ttg ctg cag aag gcc gag ccg cac aac ctt    2016
Asp Ser Ser Val Ala Ala Leu Leu Gln Lys Ala Glu Pro His Asn Leu
            660                 665                 670 cag atc aca gca gcc ttc ctg gca ggg ctg ttg tcc cgg gag cac tgg    2064
Gln Ile Thr Ala Ala Phe Leu Ala Gly Leu Leu Ser Arg Glu His Trp
        675                 680                 685
```

-continued

```
ggc ctg ctg gct gag tgc cag aca tct gag aag gcc ctg ctc cgg cgc    2112
Gly Leu Leu Ala Glu Cys Gln Thr Ser Glu Lys Ala Leu Leu Arg Arg
    690                 695                 700 cag gcc tgt gcc cgc tgg tgt ctg gcc cgc agc ctc cgc aag cac ttc    2160
Gln Ala Cys Ala Arg Trp Cys Leu Ala Arg Ser Leu Arg Lys His Phe
705                 710                 715                 720 cac tcc atc ccg cca gct gca ccg ggt gag gcc aag agc gtg cat gcc    2208
His Ser Ile Pro Pro Ala Ala Pro Gly Glu Ala Lys Ser Val His Ala
                725                 730                 735 atg ccc ggg ttc atc tgg ctc atc cgg agc ctg tac gag atg cag gag    2256
Met Pro Gly Phe Ile Trp Leu Ile Arg Ser Leu Tyr Glu Met Gln Glu
            740                 745                 750 gag cgg ctg gct cgg aag gct gca cgt ggc ctg aat gtt ggg cac ctc    2304
Glu Arg Leu Ala Arg Lys Ala Ala Arg Gly Leu Asn Val Gly His Leu
        755                 760                 765 aag ttg aca ttt tgc agt gtg ggc ccc act gag tgt gct gcc ctg gcc    2352
Lys Leu Thr Phe Cys Ser Val Gly Pro Thr Glu Cys Ala Ala Leu Ala
    770                 775                 780 ttt gtg ctg cag cac ctt cgg cgg ccc gtg gcc ctg cag ctg gac tac    2400
Phe Val Leu Gln His Leu Arg Arg Pro Val Ala Leu Gln Leu Asp Tyr
785                 790                 795                 800 aac tct gtg ggt gac att ggc gtg gag cag ctg ctg cct tgc ctt ggt    2448
Asn Ser Val Gly Asp Ile Gly Val Glu Gln Leu Leu Pro Cys Leu Gly
                805                 810                 815 gtc tgc aag gct ctg tat ttg cgc gat aac aat atc tca gac cga ggc    2496
Val Cys Lys Ala Leu Tyr Leu Arg Asp Asn Asn Ile Ser Asp Arg Gly
            820                 825                 830 atc tgc aag ctc att gaa tgt gct ctt cac tgc gag caa ttg cag aag    2544
Ile Cys Lys Leu Ile Glu Cys Ala Leu His Cys Glu Gln Leu Gln Lys
        835                 840                 845 tta gct cta ttc aac aac aaa ttg act gac ggc tgt gca cac tcc atg    2592
Leu Ala Leu Phe Asn Asn Lys Leu Thr Asp Gly Cys Ala His Ser Met
    850                 855                 860 gct aag ctc ctt gca tgc agg cag aac ttc ttg gca ttg agg ctg ggg    2640
Ala Lys Leu Leu Ala Cys Arg Gln Asn Phe Leu Ala Leu Arg Leu Gly
865                 870                 875                 880 aat aac tac atc act gcc gcg gga gcc caa gtg ctg gcc gag ggg ctc    2688
Asn Asn Tyr Ile Thr Ala Ala Gly Ala Gln Val Leu Ala Glu Gly Leu
                885                 890                 895 cga ggc aac acc tcc ttg cag ttc ctg gga ttc tgg ggc aac aga gtg    2736
Arg Gly Asn Thr Ser Leu Gln Phe Leu Gly Phe Trp Gly Asn Arg Val
            900                 905                 910 ggt gac gag ggg gcc cag gcc ctg gct gaa gcc ttg ggt gat cac cag    2784
Gly Asp Glu Gly Ala Gln Ala Leu Ala Glu Ala Leu Gly Asp His Gln
        915                 920                 925 agc ttg agg tgg ctc agc ctg gtg ggg aac aac att ggc agt gtg ggt    2832
Ser Leu Arg Trp Leu Ser Leu Val Gly Asn Asn Ile Gly Ser Val Gly
    930                 935                 940 gcc caa gcc ttg gca ctg atg ctg gca aag aac gtc atg cta gaa gaa    2880
Ala Gln Ala Leu Ala Leu Met Leu Ala Lys Asn Val Met Leu Glu Glu
945                 950                 955                 960 ctc tgc ctg gag gag aac cat ctc cag gat gaa ggt gta tgt tct ctc    2928
Leu Cys Leu Glu Glu Asn His Leu Gln Asp Glu Gly Val Cys Ser Leu
                965                 970                 975 gca gaa gga ctg aag aaa aat tca agt ttg aaa atc ctg aag ttg tcc    2976
Ala Glu Gly Leu Lys Lys Asn Ser Ser Leu Lys Ile Leu Lys Leu Ser
            980                 985                 990 aat aac tgc atc acc tac cta ggg gca gaa gcc ctc ctg cag gcc ctt    3024
Asn Asn Cys Ile Thr Tyr Leu Gly Ala Glu Ala Leu Leu Gln Ala Leu
```

-continued

```
                  995                 1000                1005
gaa agg aat gac acc atc ctg gaa gtc tgg ctc cga ggg aac act ttc    3072
Glu Arg Asn Asp Thr Ile Leu Glu Val Trp Leu Arg Gly Asn Thr Phe
    1010                1015                1020 tct cta gag gag gtt gac aag ctc ggc tgc agg gac acc aga ctc ttg    3120
Ser Leu Glu Glu Val Asp Lys Leu Gly Cys Arg Asp Thr Arg Leu Leu
1025                1030                1035                1040 ctt tgaagtctcc gggaggatgt tcgtctcagt ttgtttgtga caggctgtga         3173
Leu gtttgggccc cagaggctgg gtgacatgtg ttggcagcct cttcaaaatg agccctgtcc   3233
tgcctaaggc tgaacttgtt ttctgggaac accataggtc acctttattc tggcagagga   3293
gggagcatca gtgccctcca ggatagactt tcccaagcc tactttgcc attgacttct     3353 tcccaagatt caatcccagg atgtacaagg acagccccc tccatagtat gggactggcc    3413
tctgctgatc ctcccaggct tccgtgtggg tcagtgggc ccatggatgt gcttgttaac    3473
tgagtgcctt ttggtggaga ggcccggccc acataattca ggaagcagct ttccccatgt   3533
ctcgactcat ccatccaggc cattccccgt ctctggttcc tcccctcctc ctggactcct   3593
gcacacgctc cttcctctga ggctgaaatt cagaatatta gtgacctcag ctttgatatt   3653
tcacttacag cacccccaac cctggcaccc agggtgggaa gggctacacc ttagcctgcc   3713
ctcctttccg gtgtttaaga cattttggaa aggggacacg tgacagccgt tgttcccca    3773 agacattcta ggtttgcaag aaaaatatga ccacactcca gctgggatca catgtggact   3833
tttatttcca gtgaaatcag ttactcttca gttaagcctt tggaaacagc tcgactttaa   3893
aaagctccaa atgcagcttt aaaaaattaa tctgggccag aatttcaaac ggcctcacta   3953
ggcttctggt tgatgcctgt gaactgaact ctgacaacag acttctgaaa tagacccaca   4013
agaggcagtt ccatttcatt tgtgccagaa tgctttagga tgtacagtta tggattgaaa   4073
gtttacagga aaaaaaatta ggccgttcct tcaaagcaaa tgtcttcctg gattattcaa   4133
aatgatgtat gttgaagcct ttgtaaattg tcagatgctg tgcaaatgtt attattttaa   4193
acattatgat gtgtgaaaac tggttaatat ttataggtca ctttgtttta ctgtcttaag   4253
tttatactct tatagacaac atggccgtga actttatgct gtaaataatc agaggggaat   4313
aaactgttg                                                          4322
```

<210> SEQ ID NO 2
<211> LENGTH: 1041
<212> TYPE: PRT
<213> ORGANISM: Homo sapiens

<400> SEQUENCE: 2

```
Met Glu Lys Arg Arg Gly Leu Thr Ile Glu Cys Trp Gly Pro Gln Ser
  1               5                  10                  15

Pro Ser Leu Thr Leu Phe Ser Ser Pro Gly Cys Glu Met Cys Ser Gln
                 20                  25                  30

Glu Ala Phe Gln Ala Gln Arg Ser Gln Leu Val Glu Leu Val Ser
             35                  40                  45

Gly Ser Leu Glu Gly Phe Glu Ser Val Leu Asp Trp Leu Leu Ser Trp
         50                  55                  60

Glu Val Leu Ser Trp Glu Asp Tyr Glu Gly Phe His Leu Leu Gly Gln
 65                  70                  75                  80

Pro Leu Ser His Leu Ala Arg Arg Leu Leu Asp Thr Val Trp Asn Lys
                 85                  90                  95
```

-continued

```
Gly Thr Trp Ala Cys Gln Lys Leu Ile Ala Ala Gln Glu Ala Gln
                100                 105                 110

Ala Asp Ser Gln Ser Pro Lys Leu His Gly Cys Trp Asp Pro His Ser
            115                 120                 125

Leu His Pro Ala Arg Asp Leu Gln Ser His Arg Pro Ala Ile Val Arg
        130                 135                 140

Arg Leu His Ser His Val Glu Asn Met Leu Asp Leu Ala Trp Glu Arg
145                 150                 155                 160

Gly Phe Val Ser Gln Tyr Glu Cys Asp Glu Ile Arg Leu Pro Ile Phe
                165                 170                 175

Thr Pro Ser Gln Arg Ala Arg Arg Leu Leu Asp Leu Ala Thr Val Lys
            180                 185                 190

Ala Asn Gly Leu Ala Ala Phe Leu Leu Gln His Val Gln Glu Leu Pro
        195                 200                 205

Val Pro Leu Ala Leu Pro Leu Glu Ala Ala Thr Cys Lys Lys Tyr Met
    210                 215                 220

Ala Lys Leu Arg Thr Thr Val Ser Ala Gln Ser Arg Phe Leu Ser Thr
225                 230                 235                 240

Tyr Asp Gly Ala Glu Thr Leu Cys Leu Glu Asp Ile Tyr Thr Glu Asn
                245                 250                 255

Val Leu Glu Val Trp Ala Asp Val Gly Met Ala Gly Ser Pro Gln Lys
            260                 265                 270

Ser Pro Ala Thr Leu Gly Leu Glu Glu Leu Phe Ser Thr Pro Gly His
        275                 280                 285

Leu Asn Asp Asp Ala Asp Thr Val Leu Val Val Gly Glu Ala Gly Ser
    290                 295                 300

Gly Lys Ser Thr Leu Leu Gln Arg Leu His Leu Leu Trp Ala Ala Gly
305                 310                 315                 320

Gln Asp Phe Gln Glu Phe Leu Phe Val Phe Pro Phe Ser Cys Arg Gln
                325                 330                 335

Leu Gln Cys Met Ala Lys Pro Leu Ser Val Arg Thr Leu Leu Phe Glu
            340                 345                 350

His Cys Cys Trp Pro Asp Val Gly Gln Glu Asp Ile Phe Gln Leu Leu
        355                 360                 365

Leu Asp His Pro Asp Arg Val Leu Leu Thr Phe Asp Gly Phe Asp Glu
    370                 375                 380

Phe Lys Phe Arg Phe Thr Asp Arg Glu Arg His Cys Ser Pro Thr Asp
385                 390                 395                 400

Pro Thr Ser Val Gln Thr Leu Leu Phe Asn Leu Leu Gln Gly Asn Leu
                405                 410                 415

Leu Lys Asn Ala Arg Lys Val Val Thr Ser Arg Pro Ala Ala Val Ser
            420                 425                 430

Ala Phe Leu Arg Lys Tyr Ile Arg Thr Glu Phe Asn Leu Lys Gly Phe
        435                 440                 445

Ser Glu Gln Gly Ile Glu Leu Tyr Leu Arg Lys Arg His His Glu Pro
    450                 455                 460

Gly Val Ala Asp Arg Leu Ile Arg Leu Leu Gln Glu Thr Ser Ala Leu
465                 470                 475                 480

His Gly Leu Cys His Leu Pro Val Phe Ser Trp Met Val Ser Lys Cys
                485                 490                 495

His Gln Glu Leu Leu Leu Gln Glu Gly Gly Ser Pro Lys Thr Thr Thr
            500                 505                 510

Asp Met Tyr Leu Leu Ile Leu Gln His Phe Leu Leu His Ala Thr Pro
```

```
              515                 520                 525
Pro Asp Ser Ala Ser Gln Gly Leu Gly Pro Ser Leu Leu Arg Gly Arg
            530                 535                 540

Leu Pro Thr Leu Leu His Leu Gly Arg Leu Ala Leu Trp Gly Leu Gly
545                 550                 555                 560

Met Cys Cys Tyr Val Phe Ser Ala Gln Gln Leu Gln Ala Ala Gln Val
                565                 570                 575

Ser Pro Asp Asp Ile Ser Leu Gly Phe Leu Val Arg Ala Lys Gly Val
            580                 585                 590

Val Pro Gly Ser Thr Ala Pro Leu Glu Phe Leu His Ile Thr Phe Gln
                595                 600                 605

Cys Phe Phe Ala Ala Phe Tyr Leu Ala Leu Ser Ala Asp Val Pro Pro
        610                 615                 620

Ala Leu Leu Arg His Leu Phe Asn Cys Gly Arg Pro Gly Asn Ser Pro
625                 630                 635                 640

Met Ala Arg Leu Leu Pro Thr Met Cys Ile Gln Ala Ser Glu Gly Lys
                645                 650                 655

Asp Ser Ser Val Ala Ala Leu Leu Gln Lys Ala Glu Pro His Asn Leu
            660                 665                 670

Gln Ile Thr Ala Ala Phe Leu Ala Gly Leu Leu Ser Arg Glu His Trp
                675                 680                 685

Gly Leu Leu Ala Glu Cys Gln Thr Ser Glu Lys Ala Leu Leu Arg Arg
690                 695                 700

Gln Ala Cys Ala Arg Trp Cys Leu Ala Arg Ser Leu Arg Lys His Phe
705                 710                 715                 720

His Ser Ile Pro Pro Ala Ala Pro Gly Glu Ala Lys Ser Val His Ala
                725                 730                 735

Met Pro Gly Phe Ile Trp Leu Ile Arg Ser Leu Tyr Glu Met Gln Glu
                740                 745                 750

Glu Arg Leu Ala Arg Lys Ala Ala Arg Gly Leu Asn Val Gly His Leu
            755                 760                 765

Lys Leu Thr Phe Cys Ser Val Gly Pro Thr Glu Cys Ala Ala Leu Ala
        770                 775                 780

Phe Val Leu Gln His Leu Arg Arg Pro Val Ala Leu Gln Leu Asp Tyr
785                 790                 795                 800

Asn Ser Val Gly Asp Ile Gly Val Glu Gln Leu Leu Pro Cys Leu Gly
                805                 810                 815

Val Cys Lys Ala Leu Tyr Leu Arg Asp Asn Asn Ile Ser Asp Arg Gly
            820                 825                 830

Ile Cys Lys Leu Ile Glu Cys Ala Leu His Cys Glu Gln Leu Gln Lys
        835                 840                 845

Leu Ala Leu Phe Asn Asn Lys Leu Thr Asp Gly Cys Ala His Ser Met
850                 855                 860

Ala Lys Leu Leu Ala Cys Arg Gln Asn Phe Leu Ala Leu Arg Leu Gly
865                 870                 875                 880

Asn Asn Tyr Ile Thr Ala Ala Gly Ala Gln Val Leu Ala Glu Gly Leu
                885                 890                 895

Arg Gly Asn Thr Ser Leu Gln Phe Leu Gly Phe Trp Gly Asn Arg Val
            900                 905                 910

Gly Asp Glu Gly Ala Gln Ala Leu Ala Glu Ala Leu Gly Asp His Gln
                915                 920                 925

Ser Leu Arg Trp Leu Ser Leu Val Gly Asn Asn Ile Gly Ser Val Gly
        930                 935                 940
```

```
Ala Gln Ala Leu Ala Leu Met Leu Ala Lys Asn Val Met Leu Glu Glu
945                 950                 955                 960

Leu Cys Leu Glu Glu Asn His Leu Gln Asp Glu Gly Val Cys Ser Leu
            965                 970                 975

Ala Glu Gly Leu Lys Lys Asn Ser Ser Leu Lys Ile Leu Lys Leu Ser
        980                 985                 990

Asn Asn Cys Ile Thr Tyr Leu Gly Ala Glu Ala Leu Leu Gln Ala Leu
        995                 1000                1005

Glu Arg Asn Asp Thr Ile Leu Glu Val Trp Leu Arg Gly Asn Thr Phe
    1010                1015                1020

Ser Leu Glu Glu Val Asp Lys Leu Gly Cys Arg Asp Thr Arg Leu Leu
1025                1030                1035                1040

Leu

<210> SEQ ID NO 3
<211> LENGTH: 37443
<212> TYPE: DNA
<213> ORGANISM: Homo sapiens
<220> FEATURE:
<221> NAME/KEY: exon
<222> LOCATION: (63)..(106)
<220> FEATURE:
<221> NAME/KEY: exon
<222> LOCATION: (3908)..(4406)
<220> FEATURE:
<221> NAME/KEY: exon
<222> LOCATION: (12307)..(12412)
<220> FEATURE:
<221> NAME/KEY: exon
<222> LOCATION: (15010)..(16825)
<220> FEATURE:
<221> NAME/KEY: exon
<222> LOCATION: (21017)..(21100)
<220> FEATURE:
<221> NAME/KEY: exon
<222> LOCATION: (21321)..(21404)
<220> FEATURE:
<221> NAME/KEY: exon
<222> LOCATION: (24355)..(24438)
<220> FEATURE:
<221> NAME/KEY: exon
<222> LOCATION: (27052)..(27135)
<220> FEATURE:
<221> NAME/KEY: exon
<222> LOCATION: (27730)..(27813)
<220> FEATURE:
<221> NAME/KEY: exon
<222> LOCATION: (29917)..(30000)
<220> FEATURE:
<221> NAME/KEY: exon
<222> LOCATION: (34244)..(34327)
<220> FEATURE:
<221> NAME/KEY: exon
<222> LOCATION: (36123)..(37443)

<400> SEQUENCE: 3
tcaccatata actggtattt aaagccacaa gagcaggtgg gctcatctag ggatggagtg      60
atatggagaa gagaagggt ctaaccattg agtgctgggg cccccagtgt taggaaccag     120
ccaagaagac agaagagtg aaaatcagag agttggggtg tcctggagga aatgaagaaa     180
atgccccaaa gaggaaggag ggaacaaata tgaccaatgc ccctggcaga gcaagcaggc     240
tgagggctga ggattgagca atgggaggtc actggtgaca gtttcactgg agctggatgg     300
ggaactagag ggaatgggag gggatgggag gacttgggga cagcagtaca ggcaacagac     360
aagggggcct gctgtaaagg gagcagataa atgggattgg agccaaatga agaaggggag     420
```

```
tgtcaagaga gtgctttact tttacaatgg agaattagag tgcattgtgc actggtgggg      480
ggatttgatc tcttagggag agaacagtgt tagggaggga gaatgcagga tagctggggg      540 agggtgggg gcttggcccc agcagagact caggacactt gggaagttga gcttccctgg       600
gcttcccctc ctctcctgtc tgcaaggggt cagtgggctg agatttcagc acttaagcaa      660
agcatttgct cttggcccca gagaaaccgg gctggctgtg gtctcaggaa ggaaggaggt      720
gtccaggctc aggcctgggc ctgggtttca gggagggccc acgtgggtca ccccttgacc      780
ctctctttca gcaaggaagt gatcctttct ctacatgggc ctcaccttgg ggaggacaat      840
ggtgtctttg aagttgtagt aactgaagta gagatcaaaa ggcaatgcag atagactgac      900
agatttcgcc tgaagagggg aagcccgacc aggtaataaa ggagtaagag gaaggatgtt      960
aaggacaatt ttaggaaaca gataatgagt gaatattttt tctctctctt tcccaattta     1020
aactgaagca ggagaaactg aagctagaca taatgattaa cttcccaagc tggtgagctt     1080
cctgagctgg ttagtgagaa cagcactaag gccaggttct cctccccaga tgtttaagat     1140
gagacaggac aatgcctgct cagagacagg gcctggctga attggccctc aggattctct     1200
ctgctctgag gtttctggaa gaaggccagg gcagaggtgt ggtgatgtag ctgctgggag     1260
gacagagctc cgagtcacgt ggcttgggcg ggcctcccct tcctggtgtc cacagaagcc     1320
caacgtcact agctggggtg tgtatggctc acacgtaggc caggctgccc taggcttggt     1380
gtgcaaggga ggggccccta cttacttgtg gcctgtcccc tcgtgaatgt gtctcatgtc     1440
cccagtgggg tttttcagtg agggtcatgg tctccaggat gcacaaggct ttgtgccaga     1500
attgcttgga attgcctagt tctgaaggc tggttggcca actctggcct ccggcttttc      1560
ctttgggaat ttcccttgaa ggtggggttg gtagacagat ccaggctcac cagtcctgtg     1620
ccactgggct tttggcattc tgcacaaggc ctacccgcag atgccatgcc tgctccccca     1680
gcctaatggg ctttgatggg ggaagagggt ggttcagcct ctcacgatga ggaggaaaga     1740
gcaagtgtcc tcctcggaca ttctccgggt aagaggagca ggcattgtcc cgtcccagct     1800
tgatcctcag ccttctttca tccttggccg cgacatgctc ccaggcctgg ggtcagatgg     1860
ggagtgctga ctctgttcct gggctgtttt ctggggagaa tgggtcggcg gttttttttc      1920
cccaggacct gggcagggtc aatggtgggg gccgctgtcg catccttggc tggtgtttcc     1980
acagctgaga accactccag ggccaagccc agagcttatt ctaccctttt ttgtcctctc     2040
ttcccctgtc ctcggccacc ccaccctctt ggctcctctg cttagatgtg ggcacaagga     2100
ggagaactcc ttggcctgag agaactacct tagatcctgg cttccagtgg cctctgcagg     2160
ggggtacacc ctctctccca agcagccaga cacacaagta acctcattgc ctcagtttcc     2220
ccatctgacc agcacagggc cccctgtgcc ccagcagcgt tctgagagat tggagctttc     2280
tccttttgct taccttggct accgtatgag gacggataca gagtgttccc cccaccccca     2340
gcccagggga tatttgattc atgaacattc cctcagtgtc tttgtggggg acaatgctgt     2400
gccaggctca gggatgccag gacgagtaag acccaggctc ccacgtggcc caggcaggga     2460
gagagacaca taaacaacca tcaggaaaga ggtaaaatcc ccaggccact tggcatctgc     2520
tcccttgagt gtctgggaat gtccctgatt tataaaaaga agctgacggc cctcttttgtt    2580 gtccatgcct acacccttt actttcgttt cttcgggca ctgcagcagc ccttgtccac       2640 agacccatg acaatcgcag aactgaccat gctgagagat tttcttggct gctcagggac      2700
cctgccaggg cttgaagctc ctggagggtc acttgccctc aaattcccag aacgcacagc     2760
aggtcactga tgatagcagt ggcagcagtc tgtgcacggt ggtttcgagg gcgtgggagg     2820
```

```
gaggtgaggg ccctagggca agtgtgtgtg ggaagtgttg atgggggaca aggcaccaga    2880
acgctcggaa acaacttagt ttgcaccgta attttcact tcgcctagga caggaccttt     2940
agagcaatat tctgagtcta ccccttggag tagcagtgtg caaaacacac agcacgggct    3000
tggggccccc gtggggaacc caaatgtaag agttagagac atgcattccg gagtcataca    3060
tggctcgtgt tgaaatcctg actctgcctg tctagctgtg acacatcgta caaatcactt    3120
agcttcttgg tgcctcagtg tcttcctctg tagaatggga agatcatagg cactacttca    3180
gagtggctgg gagggttcag tgaattcctg caggagagca cttagaatgg cacttggtgt    3240
gtagtttatg cttaattaat attagccgtt actgaaactg ctgtagcctg aatccagcca    3300
gcatgaaaga gcccctctca ccctgcttcg aagagaatga attccctgat tgtttggaag    3360
atctctctct ctctctctgt ctttttttt tttttttgag aaacggtctt gctctcttgc     3420
ccaggctgga gcgcaatggt gccatcttgg ctcactgcaa cctctgcctc cgggttcaa     3480 gtgattctcc tgtctcagcc tcctgagtag ctgggattac aggcgctcgc caccacgcct    3540
ggctaatttt tgtattttta gtagagacag cgtttcaccg tgttggccgg gctggtctag    3600
cgctcctgat ctcaagtgac cttgggagat ctccttgctcc taatattacc tcaagccttt   3660
ttaaacgttt taagccggag accaagcatg gatatgggag ttaggggtct tgatttaatt    3720
cttggttgct tcaaactctg tggaaccttg aggtgtttct tgccttctct gggtctcaat    3780
tttcacatct atatggtggg gagcttggat tgggtaatgt ctgaggctag aaccatggcc    3840
aactcgggtt ctgctggggc tgacttgccc tggccttccc tgaccaccct gcatctggct    3900
tctggagaag tccctcactg accttgttct cctccccagg ttgtgaaatg tgctcgcagg    3960
aggcttttca ggcacagagg agccagctgg tcgagctgct ggtctcaggg tccctggaag    4020
gcttcgagag tgtcctggac tggctgctgt cctgggaggt cctctcctgg gaggactacg    4080
agggcttcca cctcctgggc cagcctctct cccacttggc caggcgcctt ctggacaccg    4140
tctggaataa gggtacttgg gcctgtcaga agctcatcgc ggctgcccaa gaagcccagg    4200
ccgacagcca gtcccccaag ctgcatggct gctgggaccc ccactcgctc cacccagccc    4260
gagacctgca gagtcaccgg ccagccattg tcaggaggct ccacagccat gtggagaaca    4320
tgctggacct ggcatgggag cggggtttcg tcagccagta tgaatgtgat gaaatcaggt    4380
tgccgatctt cacaccgtcc cagagggtga ggcactcctg gtgtgcatca cagagttctc    4440
aggaaagggg tgcttagtca ccaagactga tttgtcctca tgaagtcagc ctgtggggta    4500
acttggtccg tgggatttcc cctaaaaagg tagccaggca ggtaaaattt gctcttgact    4560
cttggcagga aacatacaac tctttctttc ttcttttctt ttcttttct cactctgtta     4620 ccctggctag aatgcagtgg cacaatcata gctcactgta gccttgaatt cctgcgctca    4680
agtgatcttc tggccttaga gtagctggga ctacggctgc tgtaccacca tgaacagcta    4740 atttttttt tttcttttag atgggggtg ttgctatgtt gcccaggctg gtctccagct      4800
cctggcttta agcaatcctc ccgccttggc ctcccaaact gttgggattg caggcatgag    4860
ccactttgcc tggccaacag aacacttctg ccgagaggaa gtgtgtggtg gccaggaact    4920
cagattctgg agccagaatg gtgcaggctc aaggtcaacc ctgtgtgatc tcaggcttcc    4980
ctatggagcc tctccagcct cagtctccct tgtttcagtt tcctcatcta caaaacaatg    5040
ttaatagtca aatggtgcct atcctataag gctcttggga ggattcagtg agttaatttg    5100
agtaatgctt aggatagtgt ctattaccac tggctgctat ttattatttc tgttatgagt    5160
```

```
gatactctgt acttgtacac ttttatttct gtctgtttta aattaacagc acaacagacc   5220
ataacactgc agtatattga atttatttta taattaacat agcatattat aaactaatat   5280
agcttaaatg tttatgtagg atttctgaca tgaaattgca ttagatcata gatgttcaga   5340
gttggtatat aacagcccct gagaatgtag taactcagca gagaccagaa ggtcagagaa   5400
atgaccactg agtattttg aaactctttt gttttcttcc aaatagtgat tcttagggct    5460
cctgagaggc agatggaaca atcattaaca ttccacttta taaatcggga agttgagacc   5520
aaggaaagta gtttgaataa gctcacagta gttaatgagg gggccagtgc tggaccaatt   5580
ggccagcact ggtcattgac ttattcatcc atcattcatt tattcagcca gaatctatta   5640
ggtgcttcat acatatttgc ttaaagtttg ttgtgttcat agagctttgc acacggtagg   5700
tactccataa acatttgttg atgaaataag tgagttactg aatgaatgat tgaattagaa   5760
tgacactgca gtgttaaaat gggctgggtt ggggaacatt ttagtttttg tttttgtctg   5820
ttttccaaaa atgtatgtgt tgttcacatg agtctggata accctagatt gagattgatg   5880
acataaataa atttgtcttc aaggctgcac taaagctggc tcacatggct aggtatttac   5940
agagcagaag tggtgcagtc ctctctgatt agttgcacgt acagaagaca tattcgttat   6000
tggactgacc ttagttttctc ttataatttg ttaggggaat tgaatcagcc catctgagaa   6060
gttacaagat tgtgtcttgt catctttaaa agttcagcaa tgtgatgtgg tacagatggt   6120
ctgaggggtt tggagaaggt agcctagatc cctagggccc agagaagaca ggatgtgaac   6180
agaggaagta catggattgg tgaagaaaag aaatgggata actcatgggt caagaagaa    6240 atcatgatgg aaatcagaaa atattcagaa ccatacaata atgagaatat tatttatcaa   6300
aatctattgg atgcagctaa agcaggacat aggggaaat ttacaacctt aggtgcctag    6360
attaggaaag aaggaaggca tttgtttatt tatttgttta tttatttatt tgagatgggg   6420
gtctcactgt gtcacccagg ctgctggagt gcagtagcac gatcataaat cactgaagtc   6480
tcgaacttct gggctgaagt gatcctcccg cctcagcctt ccaagtaggt gggacacagg   6540
ctagcaccac cataccaggc taatttttt tttgtagaca cagggtcttg ctatgttgag    6600
gtctcaaact cctgggctca agtaatcctc ctccctcggc ttcccaaagt gctgggatta   6660
caggcatgag ccactgcgcc catctaaggc tgaattttaa tgagctaaga attcatctta   6720
agaaagggct aaatagacag caaaagcaaa cattgaaggt tgggactgag ctgagtgggt   6780
agcagggatg ggagacaaca gatctgagga gagcaggaga ttttgaaagg attgcactgc   6840
ctgaggttta agcctttaga atccagctct ctctgagctc cctttgagct ctgacattct   6900
gtgactctga tttggtggcc ttcccttagt ggccttactg atttcatttg gatggtgctt   6960
gtggtatatc caaccaacat gtcttcccaa atggccttt aatttcctat aaagaagtag    7020
ttgtcattga ttgcaggtta gggacagaaa atgctgtgga atgaaacaaa atgcaagtta   7080
aagaactaaa ttccaaaaat acccattgct actattgact gagtgaattc ctactgtgtg   7140
ccagacactg tacccagtcc attccctgta ttgttttatt taagcctcac aagggtatag   7200
tgtgactaca ctgtttctta acaatgaaga aactgcccaa atcgcccatc tgggaagcgg   7260
cccagctaga atttgaatcc aggcctgttt tcctccagag cttgtgctat tctctgtctg   7320
tcataaaatg tgggggcttt gtgtggtaaa cttgctcagt gggcatagc agttgttagg    7380 aaacctgagg ctggtaacac cagctgtaat accagctgtc cgtctgactc atgcaactgt   7440
taaagttgat agggctgagg tgtcagactg agctctgaat tgcctgattc ctataacaat   7500
attaacttaa acatttttta aattgggaaa tgcaccatgc atacagaaga gtgtgtatat   7560
```

```
ttcatatgta tagtgtaaac tgttcccatc acccaggtta aaaaacagga tgttgccagt    7620
acctggggcc ttctttaact gcaactgcta gaggtaaaca ctggcttgac ttttgtgtaa    7680
atcatctctt tgccttttctt taatgtttta gcatctttta aaataaatcc ccaaataatg   7740
tattgttcta ttttgaaaaa ctgagtagca agccaaaaat agctgtgtaa agaaaggtca    7800
cttaaattag gctgggtgca gtggctcaag cctttaatcc cagtactttg ggaggctgag    7860
gcaggtggat cacaaggtca ggagatcgag accatcctgg ccaacatgga gaaacccgt    7920 ctctactaaa aatacaaaaa attagccaag aatagtggca tgtgcctgta gtcccagcta   7980
ctcgggaggc tgaggcagga gaatcgcttg aacccgggag gcagatgttg cagtgagctg   8040
agatcgcact gcttgaaccc gggaggcaga ggttgcagtg agccaagatc gcaccactgc   8100
actctagcct gggtcacaga gcaagactct gtctcaaaaa aaaaaaaaaa aaaaagaaag   8160
gttactattg cctttctta tgaaggtt cccaaggcag ggaaagctaa gtggagtctc     8220
agggacttgg tctggctttt ccttccctgg gaatttataa ggacctcttc tgggaagtca   8280
gtcggcaatg ccatgaatga gtctggggaa atattgggct cattgcaact ggagggtctg   8340
gtaggactga tgtgaattag gtgctgtgtc cggaggaaaa tggccagagg aagtgggctg   8400 cttttgtacag tcagtggtaa agttgccaaa ggctattata gctcacagga atgggccaag   8460
gctaaacact cctgtggagt gaaatgaatg tcctcagctg actgaggcag cgggagttga   8520
gaagaaacga tattagttca tggtgaagac aagtcaaata tagataaagg ttagggtcag   8580
gcttgcctgg acatctagga gataactgcc ctcaacttgt ttgaatcttg agtcactgct   8640
ccattttgtt tgaactggtg gccatctact tatagtatac agccatcaac ctgagatttc   8700
cctacatggt cttcctgcct tggtctcctg tatcctgaat cctatggcct cttcttccct   8760
ggtttactac attttgctag accgtatcct ccagtcaatt ccttagaatg aatgtatgaa   8820
agttaaaatt tctgaggtct cacatgtctt aaagttccct catactggat tgatagtttg   8880
gctgggtata aaattctggg ctggccatca ttttccttca gaattttgat tgcattattc   8940
cattatcctc tcttttcaat attgcttcta agaattccaa aacctttttt tttttttctt   9000
tttgagacag tgtctcactc tgtcacccag gctggaatgc agtagtgtga tctcagctca   9060
ctgcaacctc cacctcctgg gtttaagcga ttcttcttcc tcagcctcct gagcagctgg   9120
gattacaggc acccaccacc acaccctta gtagagatgg ggttttgcta tgttggccag   9180
gctggtcttg aacttctgac tttaggtgat ctgcctactt cggcctccca aagtgctggg   9240
attaaaggcg tgagccacca cacccagcct ccaaaaccat tttaaaactc tttctggaag   9300
cttttaaaat tttcttttag tccccagaat tttaaaattt caattatgtg ccttggtgtt   9360
cttccattat attagtcacc caagaggtac tttcaatctg gaaacttctc tatgttttgg   9420
gaaatgttct tgattagttt acaggtgatt tcttcctctc cattttatct cttctcttttt  9480 catgaaacta ctattaattc aatgttagaa ttccttgact gatcatttaa ttttcttcta   9540
ttttccatct ctgtgtcttt tgctctact tttctatgat agtcacagct ctatctttaa    9600
actcttgagt ttttcatttt tgatgtcatg attttaattt gcaagaggta ggtttgactg   9660 attcttttt gtagtatctt actcttgttt tatggatgca acatcttctt tgacttaagg    9720
atcataagat aggtgggttc tttgtttgtt tgtttgactg ttttcacccc tatgtaaact   9780
ttttctacaa gttctcttcc ccttcccccc ttttggctt ctatctccca cattagatgc    9840
tttctctggg ctcatgatac tctttggttt tcttttctcaa gattgacagg taggacttta   9900
```

```
aaacttgttg agcatgcggg tgaaacttgt ctaccatgaa tttcactgta gatattttgg    9960
agattgacag tgtttatatc tttagatctc acctcctggg ttgatcaagt tatctgagta   10020
caccacagac cttttgcctg gggataaacc agaaatctgt ttcagaaacc actttgattc   10080
agtcttcctt gttttagtca tttccttcag ttccggaggt ccgtcatgct gatcattcca   10140
gagcccttta cagatcctag ggtacacact gcatggtttt caactttctt gttttggggt   10200
taagatttgg ctttcaggag tctcctcagt ccgttactat tcattcaatc agcaagtcct   10260
tgagcacctg atttgtgcca gacattcttc taggtgttag ggatacctca gtgaacaaaa   10320
cagacaaaaa tctttgtctt ggaaatacac acactccagt caggggagag ggacaataag   10380
ccaaaggaag gaaattacag cgtgtgctag aaggtgataa gtgctgtaga aagtaagtaa   10440
agtgggtttg ggagttgaga gtttgggaag gggataaatg atggcaattg taaatagagt   10500
agtcagagtt ctcacttaga aggtgaaatt caagtaaaga cttgaaggag gacagggaat   10560
tagccacatg gatggctagg ggaaggcttc caagctgaga ggacagccag agccaaggcc   10620
cagaggcagg agcatacctg gtagttttag gaaacaggag gccaggatgc tgagtggagt   10680 aagaggggc atgaaaggag aaacttgggt ccacgtggtt ctagacaggt attttgtct   10740 gttttgggcc ctgaaggtta ctattggact tggactctta ctctgaggaa ataggacgc   10800 tattgggacg tttgtacagg agcaatgtga cctgagtttt gtttgtaaag gattagactc   10860
tggctgtggc attaaggcta ggctgtgggg gcaggaacag aagcagggg accagttttg   10920 cagcctgtgc agctttccag ataagcaggg attgtggctt ggaggaggat ggtatagagg   10980
aggtgacaag aaatgactct atgtctggta tgtagatatt ggccacagat ggcatttgag   11040
cactagagac ctggctggtc cacatggagt ttccataagc acataataca catcagattt   11100
caaagactta atatgaaaaa aaaaatttaa cgggccccgg gaattttttt ctttttttt    11160 tttttgaga cccagtcttg ctctgtcacc caggctggag tgcagtggtg tgatctcggc   11220
tcactgcaac ctccgcctcc caggttcaag tgattctcct gcctcagcct cctgagtacc   11280
tgggactaca ggcacctgcc accacgcctg gctaatttt tgtatttta gtagtgatgg   11340 ggtttcacca tgttgtccag gctggtctgg aactccggac cttagggat ctacccgcct   11400 tggcctccca aattgctggg attacaggca tgagccacca tgctcagcca tatcttgcta   11460
ttttctacat ggattacatg ttgaaatggt aatgttttgg ctattgtgga ttaaatagaa   11520
tatatgatta aagttgattt catctatttc ttttaacttt aaaaaatatg tctgttagag   11580
gatttgaaat tccacatgcg gcttgcattt gtgacctgca tttcatttct gtggaacagt   11640 gcccttttg ggacatgctt tgaaggtgga gtcaacagga tttggcagat tacagacgag   11700
aggcttcaag ggtgactcca agacttcggg gcagagcacc tggaagaaag gggttaatat   11760
tagccaagat gaggaaggct gtcggtttgg caggtgcatg ggcaggttag gagtttagtt   11820
ttgaatatgt tggaggtgtt tatgaaactt ttaagtggag atggaaaata ggcagttgga   11880
tgtgcaagtc cagggttcag ggagacagtt caggctggag atgaagatgt gggagtctga   11940
ggagagattg tattcaaata ttcaatccat gagacttgat gaaatcactt ctcttccaaa   12000
tgatttacag cctgcagaat cattttccct atctttgtag gttatgtct tcattttgtt   12060 tcatttattt ttcagttatt cactgttta gtgagttttg agtaggagcc agattggatg   12120
catgcgttca attcaccatc caacactgta ttaactactt gaaactcatg tggttgttcg   12180 gttgttttt tgacccttta ttctggatgg aagagagatg cttatgaagt tgcagtaatc   12240
agtaagcctt cccacattgc tccatcagcc ttcctggaag aataatgtct tctgcctttc   12300
```

```
ctgtaggcaa gaaggctgct tgatcttgcc acggtgaaag cgaatggatt ggctgccttc    12360
cttctacaac atgttcagga attaccagtc ccattggccc tgcctttgga aggtaggtgt    12420
atgttctcag ttaatcagaa agggaagggc agtcagtgca gatccatggt taagagcaga    12480
acacacctcg gttaacatcc catatgctgg cagtatagcc tccctatgac tcaatttcct    12540
tgttttaagg ctagcaccac cccgtctcat tgggattttg ggagcattaa aaggacaaaa    12600
gcgtgtaatg ttagctatta gctttcatta tctcccacac agtatactga caattgggct    12660
accatatatt gagggctaac taaaggtgtt acttaccatc caaactctca ttatctgtac    12720
cgaaaagata tggacacatg ttttgagtta gggctggtat ctcttgatct ctgaaattta    12780
gcagctcaca atgggaaact caagaaccaa gtggatctag agactctggt atccctcagt    12840
gcccagggtc accacccaaa ctcaggaaca ggaggggctt ggaccgcacc acttgaacat    12900
accaggcatc ctgccaggtg ctttatggac aatgtctacc ctttgcaaca accctgagaa    12960
gtaggtggtg tttttttcca ccttatagat gtggaaactg gcagggagg ttaagtgacg    13020 agggagggga agatgggtct gattgtaaat tgtccccacc tacactttct cttttcttgg    13080
gagaagaaat gtcagttgta aagagagagt gcaagcctgg cactctttag ggcttgttcc    13140
tacaccactg tagggaaagc tcattggcac tgaagccccc tgagctgtgt gtggtgctgg    13200
cagatgggtc tatcaccctg gactgtgtcc tctgggcagc aagcaagcct gtgggcgggg    13260
tggctggaag tctgtgcctg gcactcgcga gtgcaccgtc tcattgaaga acaggatcta    13320
aacatcagtg cgccacagca gggtgcgcgg cacggagtgc aggccctggt ttggcccttg    13380
gttgaggttt gctgttgaca tcatcaagca cagctagtca ctgtaagacc aggccagggt    13440
gcaagattcc ccacacttct aaaggtgaca attggtgtat ttatttctct ataaaatgac    13500
attttttttt tctggagaat tttagtatca ttggtgatga ctgaaaaacc tgcatcagaa    13560
atcaggtcgg aagaggaaga tatatatctg atatgtactg gagaggaaga tatctatctt    13620
atggtctaag ttcagggatc ctggtatatt cagagggcag aaagctcagc aataatcatc    13680
aactctggga acagaggtga cataaacaca gggcgtcccc tttgtgtgac tgcagatagt    13740
catcagtgag ctcagagctc tatgaaaatt acttgctagt ttttgggttg aaaatagtgg    13800
gccagtgttt ggttggggc agtgaggctg tgatggcggg ggaccatgcc aagctcctac    13860
cagcctggga cgctaaacca gcacttcccc atttcctgaa aggggaacta aactctgaca    13920
caggaaatgg tttgcttgca ttactttcag gatgagaaag gaagagcact ggccttccaa    13980
acacaccccg tgcatgaaaa ctctccctgc atggggtgca tggggaggat ggggaagtgg    14040
aggcaggatc acagactctt gttcgagtgc tcagctgggg caccccggtg accccgaggc    14100
cttcccttgc taggtccacc cagatcaatc aggatcatct ccccatctcg aagtttaact    14160
ttatcacatc tcagagttcc ttttgccacg taaggtaaca tattcacagg ttctgagaat    14220
ccggacatga acatctttga gggtctattg ttgtgcctac tatatccatg aataataatg    14280
ataataagca ccattttttg agagtttgcc atgtcagata ttcttttaaa ctgtatttta    14340
tctcgctgcc tcctgaaaaa atccttccag gtgtatattg tccccatttt tacagatgag    14400
agaactgagg cccagaaagg ctaaatggct tgcccaagtg tatggtggac ccaggttttc    14460
aaactcaggt gtgtctggct tcagagactg ggctcctgag cccttaagcc ctttgttccc    14520
ctttagaaaa agtcacctga ggctgagtgg tgaagggatt tatccaaagc cacccggcca    14580
ctatggcagg acagatatca gaatacaggt cttccgatcc cagcccagag ccccttcccg    14640
```

| | |
|---|---|
| tcatctagaa ctcctcctgg tgtcagtaat gataacggca gtcactgatg tcttttgagc | 14700 |
| acttactttg tgttgagcac ttacactgtg ctaagcactt gacataggtc atcttagttg | 14760 |
| atccgtgtaa aactctgtga ggtagtgacc aacatttctc ccaccttaca gaggtggaaa | 14820 |
| ctgagggtta ggaagtttcc ttgactgtcc tcaaagtgca cagcttgtga atggaggagc | 14880 |
| caggatgggc gcccgctggc tctcctatcc cttcagttat gtcagcgtcc cccgcagcag | 14940 |
| cccattgtct ggttaggtcc cgtcttcacc atggtgccac cttcatctgc ctcttcttct | 15000 |
| gccttccagc tgccacatgc aagaagtata tggccaagct gaggaccacg tgtctgctc | 15060 |
| agtctcgctt cctcagtacc tatgatggag cagagacgct ctgcctggag gacatataca | 15120 |
| cagagaatgt cctggaggtc tgggcagatg tgggcatggc tggatccccg cagaagagcc | 15180 |
| cagccaccct gggcctggag gagctcttca gcacccctgg ccactcaat gacgatgcgg | 15240 |
| acactgtgct ggtggtgggt gaggcgggca gtggcaagag cacgctcctg cagcggctgc | 15300 |
| acttgctgtg ggctgcaggg caagacttcc aggaatttct ctttgtcttc ccattcagct | 15360 |
| gccggcagct gcagtgcatg gccaaaccac tctctgtgcg gactctactc tttgagcact | 15420 |
| gctgttggcc tgatgttggt caagaagaca tcttccagtt actccttgac caccctgacc | 15480 |
| gtgtcctgtt aacctttgat ggcttgacg agttcaagtt caggttcacg gatcgtgaac | 15540 |
| gccactgctc cccgaccgac cccacctctg tccagaccct gctcttcaac cttctgcagg | 15600 |
| gcaacctgct gaagaatgcc cgcaaggtgg tgaccagccg tccggccgct gtgtcggcgt | 15660 |
| tcctcaggaa gtacatccgc accgagttca acctcaaggg cttctctgaa cagggcatcg | 15720 |
| agctgtacct gaggaagcgt catcatgagc ccggggtggc ggaccgcctc atccgcctgc | 15780 |
| tccaagagac ctcagccctg cacggtttgt gccacctgcc tgtcttctca tggatggtgt | 15840 |
| ccaaatgcca ccaggaactg ttgctgcagg aggggggtc cccaaagacc actacagata | 15900 |
| tgtacctgct gattctgcag catttctgc tgcatgccac cccccagac tcagcttccc | 15960 |
| aaggtctggg acccagtctt cttcggggcc gcctccccac cctcctgcac ctgggcagac | 16020 |
| tggctctgtg gggcctgggc atgtgctgct acgtgttctc agcccagcag ctccaggcag | 16080 |
| cacaggtcag ccctgatgac atttctcttg gcttcctggt gcgtgccaaa ggtgtcgtgc | 16140 |
| cagggagtac ggcgcccctg gaattccttc acatcacttt ccagtgcttc tttgccgcgt | 16200 |
| tctacctggc actcagtgct gatgtgccac cagctttgct cagacacctc ttcaattgtg | 16260 |
| gcaggccagg caactcacca atggccaggc tcctgcccac gatgtgcatc caggcctcgg | 16320 |
| agggaaagga cagcagcgtg gcagctttgc tgcagaaggc cgagccgcac aaccttcaga | 16380 |
| tcacagcagc cttcctggca gggctgttgt cccgggagca ctggggcctg ctggctgagt | 16440 |
| gccagacatc tgagaaggcc ctgctctggc gccaggcctg tgcccgctgg tgtcggccc | 16500 |
| gcagcctccg caagcacttc cactccatcc cgccagctgc accgggtgag gccaagagcg | 16560 |
| tgcatgccat gccgggttc atctggctca tccggagcct gtacgagatg caggaggagc | 16620 |
| ggctggctcg gaaggctgca cgtggcctga atgttgggca cctcaagttg acattttgca | 16680 |
| gtgtgggccc cactgagtgt gctgccctgg cctttgtgct gcagcacctt cggcggcccg | 16740 |
| tggccctgca gctggactac aactctgtgg gtgacattgg cgtggagcag ctgctgcctt | 16800 |
| gccttggtgt ctgcaaggct ctgtagtgag tgttactggg cattgctgtt caggtatggg | 16860 |
| ggagcaccat caaggctaag tgtgggagca ccgagctggg ctctagaagt ctgggcccag | 16920 |
| cttcgcctct gccaccctgc tttgcaacac tgcccagatc ccttcccttc tgggccttaa | 16980 |
| tttcaatatg tgatgatgac agccacactt tattgactgg cctatgtgct gggtctggtg | 17040 |

```
ctatgctttc cggaatgacc tcatctaatc tctacaacca ccctgggggg taggcaggaa   17100
tgttattatc tccattatcc ttgacttgag gctcagagaa gtgaagtaac ttgtccagga   17160
aatggcagag ctggggttca caaattgcat cattctgatt acaggttttc tgcctcccac   17220
cagtctatgg atacacttca gaggctccct gaaaaccttg aggtcacttg cagaaagttt   17280
tgtgtagtat gtgtccgtat caggaacaac accaaatcag aggtgacttg tgccccatca   17340
gagactttaa caccccaacc agatgggaat tcaggaccc aagaaataga aagtggctgc    17400
agggttacaa ctactgttgg attcctgagg tagcacagtg tccaaacagg atttcagcac   17460
tacccgtatt gcttagagcc ccagccaaag atgtgaggtt tgccctttg gagaatctgt    17520 gcccctgaac tcgggggcct ctttccacat cttggggggca ggcaagggca gagggtgtgc  17580
ctaggcctgc ggatcagcat gcgacagatt ccccaacatc cttccagctt gaaaggggat   17640
tgccctgctt ctatttagaa cctataggaa agcagaagtt ctagattgaa gttaaaattg   17700
attcccagcc tccaggggct ttgggctaca cctggatgac cttaattgac cctaagcatg   17760
ggacaaacca cttcctgaga gtattaggat ggtatacatc ttctctgggg gcaaagcaac   17820
aagatttatt tttcatcatg gaccaaacac atggatacc actagaaact gtgtagtgaa     17880
ttttgttaac cctgacatag gaccatggt ctttaggtta aagcataata acaacataat     17940
acataacata tatagcgaat atatatatgt attatatgca atgaatgtaa atatgattat   18000
acccatcatg gtcttggagg aaacagatga cacacttaaa atgggtgttt tgaggagagt   18060
ttgaaaaaca gattgtttac aagccatggg caggagttag gaaagagtgag agggttggtg  18120 caggggcctg gggttagtaa cagctggggg agggtagact tgaaggggga aggggaggga   18180
gactaattag ctgggggggaa ggtatggaga cggctgcctg agcttctgca aagtggaaga  18240
atactgcttg gccctaactc ctcaccccaa ctcttgctcg tggccagcgc cttccaccag   18300
ctggacccat cagggaggcc gagtgggctg tctgctggag tagtccccag gcatcagcct   18360
cccaggagcc agggacgggt agagaagggg gagagtggat ctggccaggc aaatggaaaa   18420
cagccagcac caaactctat ttccctagga gggaggatca tgatactttg agtgggaatt   18480
tggaaacctg tctgttggag caatttccct gatagaaata agaatgtgca ttttcctggg   18540
tagtagactc agttttttacc ccaagaggcc aggcatcact ggcctgtgtg atcctcatag   18600
gccagtccat ctctggaatt cttgaatgga tcatccatcc ttgattaggg atgtccccgt   18660
gattaccagg gtgtgcagaa gggctctggg aaacctgtgg gtctgtctct gtgttcagag   18720
aaaggtgagg gtggcctggt tctagctcat ggtgctcaga ctgtggtgtg taaaggcact   18780
cgtggcaatg cagattcctg ggcctgcctc tagtgattcc cattcagtag gtttggggtg   18840
gggcccagga aatctatatt tttcacagac acccctggtg attctgatac aagtggtctc   18900
gccctgggag aactactggt ctgcagcaac cagcttggtt ttccattagc aattactgtc   18960
cttgagcgag ttttactgct cttcaccttta cacacactaa aactgccaag gccgtagggg  19020
aggggaagca accatgaggt tgctgtgagt gcactgtgtg tgtgtgtgtg tgtgtgtgtg   19080
tgtgtgtgtg tgtatgagag agagagagag attgagaaag agaggaaggg aggaaggggg   19140
agggcacagg ctcctctccc acagtgccaa cctgcctctc tcccacttga gcgtttcca    19200 tgccaactga aatcctcagc ctctaggaaa ccctatatac acagtgcccc tatataggtt   19260
tctttagact ctggctctct cagactctag agtgatggct ttaaaagttt tatgttaccc   19320
acagagagag agcacgcacc accatgtaaa catggaacct aagtttcaca aaatgacttc   19380
```

```
gctttatgaa ctctgagaca ctctgctctc ttctgttctg ttctatttcc attttagaaa   19440
tgctgctcag gaccttcaaa atgatttgca tgacctgcaa cctgcagtct gaaaaatcac   19500
tgcactacag aagtggccat aagaggccct gagggagaag ctgcacaatg tcatggttaa   19560 gagtgggggtt tggagccaag ccgcctaggc tcaaagcctt tatgtgccgt acaaccttgg   19620
caaagtcact tcgcttgtct gtgcctcagt ttctttctca cgaatgctca taataatggt   19680
tcccatttca ctggcttgtt gtgaggatga aatagtgtta ttattgagaa gtggtaaggg   19740
tagtgatcag tgctagcgat catgattcta ggtgacttttt actgtgtacc gggtgctcac   19800
aaggctttat gtgcacagcc tggtgaggct gataatacta ttgttccctc tttttttttt   19860
ttggaaacgg agtctcgttc tgttgcccag gctgggggta cagtggcaca atctcggctc   19920
atgcaatctc tgcctcccgg gttcacgcca ttctcctgcc tcagcctccc aagtagctgg   19980
gactacaggc gcctgccacc acgcccggct aattttttttg tattttttggt agcgacaggg   20040 tttcactgtg ttaaccagga tggtctcgat ctcctgacct cgtgatccgc ccgcctcggc   20100
ctcccaaagt gctgggatta caggcgtgag ccaccgtgcc cggcctgttc cctcttttat   20160
agatgaagag accagcaaat aactagtaag tcgctgatca ggatcacaat atccagctga   20220
ggcactccag agcctgagct gttaaccatt cagtcagggc ctcccaagtt tgcctaaaga   20280
taaagaatca tgtgcacagt tgttaaaata tacagattcc tgggccccac cccgcagata   20340
cttgattgcc agctccaggg tatgggcctg agaatctgtc ttttagggaa gctttcagat   20400
gatgttgtga tcaggtgagt tttgggaatg gtgccccaag aggagtggca gacagggctt   20460
gctcggcagg gactagcctg ttggagtggt gccattgggg ttaaggactg ggcagcaggg   20520
cctcactaac cacagcctat atgcctgttt ctgaagttttt ggccactctc atccagctgg   20580
tctactgtct gctgacctag atgatggtaa attgtcccca ggggtagcct gtctagttca   20640
ggctgcacct ttcgcatata tcagctcctt tccaccatca tccccttttgt gaggctgctg   20700 tgattatcat gttccttttg cagagatgga acattgcct caaattagct ctgtcatttc   20760
ctaaggattc cagggttctt tagtaggggg tctggatcct acgtcctggg ccatccccat   20820
catagtgcac cacgtcacct ccctggccag ggaccgtggg gtctccactt ttttggggtg   20880
ctccatctat gcagggtttc ctggaagcac agatgctggc acttcaggga tgaatgaaag   20940 tcttttttggg ggatttgtag atttttttttct tgtcttacta gctccatttt caaatgtatt   21000
tattttgtct ctttagtttg cgcgataaca atatctcaga ccgaggcatc tgcaagctca   21060
ttgaatgtgc tcttcactgc gagcaattgc agaagttagc gtaagtcagc ctgggctgtg   21120
gacaatgggc tccaagtgcc ctggtctcac cccaggtcgt gcagcctggg aagctgtgag   21180
tgatgggctg gggcagggggc tgtttgcatg atggggggtg caggtgattc ctgcccagag   21240
gggaagggca accctgggat ttggtgctca ctgtccaatg tgctttgctt ctgtgtctcc   21300
tctcttctgg aactgaacag tctattcaac aacaaattga ctgacggctg tgcacactcc   21360
atggctaagc tccttgcatg caggcagaac ttcttggcat tgaggtgagc ccaggttttc   21420
cttattccct ggaaactatt ttttgcccca ttcctgagtc agtctgatct ggtcttggcc   21480
tggcactgcc cacactggct cctgacctcc tgattgaatg cagggacagt gtctcatttt   21540
aagcaggggt tctctaatgc tgtgatctcc ccagtaaact ctggactagc tctgctgagg   21600
acttcctgtc ttttgacctt tagcccgtag ggcaagaaag cttttctagg cccctttcct   21660
tttctgtgtc taagagtgtc acagcttttct ggggttacta agttccacga tgcatgttga   21720
gctcgtcctg gtgggggagg catacacagt tacttgccac cccagctgtg gcagcgagtt   21780
```

```
gctgcaacac tcccaggagg tcctttcacc actcagagca tgcaaggttt gcagtccatc   21840
tggttctgca tttctgctac tccagtgtct cccagtttca acaggagtct ctctctctcc   21900
tacctgatgc ctttaaattg cccctctagc tggccgctgg gttggcctgg cttctctctc   21960
cttctctctc tctcagatat tcttgcctcc tgtgatttgt gaggcagtaa aaaaagacaa   22020
agtaaagaat tgcttccatc tattctttta cctcttgggc tgggtttgtg gatgggagcc   22080
gccattttaa aatggcgggc cacatagctc agtctcggca agggctactg agatcagaac   22140
cacaggtgcc aatttgtaca aaggactcag tcctgctacc actgcctgat ccctcagact   22200
cacaagcctg gaataggctg tggccagacc tggctggccc atccctgaga agggtgctag   22260
tttcagaaat ggaggctgag tttgtggcca acacagtagt cctccggtat gtgcaggaga   22320
gatgttctaa gacccagtg gatgcctgaa accatggaga gtatcaagcc ctacacatac    22380
catgcttttc ccaataccta cacacctgca ataaagtgta gtttataaat taggctcagt   22440
aagagagtaa tagcaactca taataaaata gaacaattat aacaatcaat atactataat   22500
aacactatgt gaatgtggac tctctccatc tccctcaaaa tatcttcttg tactgtactc   22560
acccttcttc ttgggaagat gtgtggtggt aaaatgcctg tgtgatggga ggaagtgagg   22620
tggatgacgc atgcagcact gtgctctagc gctgggctgc tgttgacctg accacacttc   22680
agaaggagaa tcatctgctc ccagagatcc ctaatctttg agcaacaatg aggtcggcag   22740
ctggatgtca ggagcagacg atcttgatga ttaccaaatg ggagcgtata gagcgtggat   22800
gcgctggacg gggggctgat tcacgtcctg ggtgggatgg agctggatgg cacgtgatca   22860
gaatagcatg caatttaaaa tgtatgaatt gtttatctct agaattttcc atttaatatt   22920
tttggactgc agttgatttc agataactga aaccatagaa ggcgaagctg cggataagca   22980
gggggcaggg attaccgtat atcattgtaa tagagagcac aggctctgga gccagactgc   23040
ccgaggtttg aaccctcatt agctgcgtga cctcaggtca gcccaatgtc tgtgtgcctc   23100
cgtttcccct tctgtagaat ggaggtaata accctggcta cctcacaggc tgtagtgatg   23160
agcaagcaag ttaatccaca tgaagggctg caccgtctgg cagggctttt atatagtaag   23220
cgagtggctg aaagatgatg ggtaaatcac acaagcactc agcttgtttc tccttatgtg   23280
agtccggtcc tccaagcagg gattcaatgt gccacccatt tattgggaa aagtcctaaa    23340 aggggaagtg gggaagggag ctgggggagg ctgggaggtg tgtccctgag tgaaggagag   23400
agggaaggaa ggaaggttga gactgggcac cttggacttc agtgcagtcc taagacatct   23460
tggcaaggct gatgaggagt tcttgaacca aattcaccag gcaggggagc ctgatgtctc   23520
aggcaggggc tggcaagtgc agatgcgagg atgttagatt ttggagcaca gcagctgggg   23580
cccttggcta cctccaagga gctgaggctg agacctgaa aggcgagttc tcctagctgc    23640
cacacccctt ctccaaggat acaataatat ctgccttata ggattgttgt gagctgagtg   23700
gcttgacgtt ccttgaaaga atgaaagcgt atagttatcc caggaagcct agggttgcag   23760
gtgagagctc tggggcttct ccgaagctct ccgaggtgtc tggattcagt tgcagcagga   23820
gccttccttg ctgggatctt ccccaccccc tagccttggc cctccctctc tccttcccttt  23880 ctggaaggct cagtgggccc cacccctccc tccagccacc tggacctgcc cagcgctctt   23940
gtgcaacagg taaagcctac ctgtagcaac aacagatctg ggaaggctgc agagggcacg   24000
atggggtctg gatcgagggc ggctgagacc agagggaaag gtgtgaccct gagtcaccct   24060
cgctgtcccg gggaaaccac ctcccaggac agctgcctac tgtggctcct gcctggaatt   24120
```

```
gtcacactgc tgtgcaaaca gcgtcccgct gcccctttcc ctttgctggg ggaaaatgaa    24180
gttgtgggag ccgctgagta aactagacct agcagcgagg gcacctgatg tggctgctgc    24240
ctcccgggca ggtcttcaat gctttcttcc tgtgtttccc tggccagggc acagacggcc    24300
ctccttttct gcctgccgct gtgttctctc agcctcctct gtcttccctt ccaggctggg    24360
gaataactac atcactgccg cgggagccca agtgctggcc gaggggctcc gaggcaacac    24420
ctccttgcag ttcctggggt aggttggatt ccaggaagag ggacctgcat ggaggggctt    24480 gggactttttg aggatttagg ggcaggtgaa actcttcagc caggaggccc cagaggcagc    24540
ccagctccag tggggaggac aagccaggga gagagtgggc ggcccttgac tgccaccttc    24600
atacttggtc tatgcctgac aaacaggaag tttgggatgt tggggctagg ggaggacagt    24660
gcccacgagc tggtgacagg aagccctctg atcctcaggg ggcgctaggg ctgtacttta    24720
gctgcatatt aaaaccacct ggaagcttct aaacactatt gccaggcctc ccaccccaga    24780
ctgatgaaat gcaaatatct aggtgcaagg cccaggtatc aggagtttta aaaagcttcc    24840
caggggatgt acagccaggg gtgaggaccc ctgacctaag aaagagaagg aaatgggaa    24900 ggataggaag gcacccagga taagaggggc tgtgctaggt ccctcggagc tcttgctccc    24960
tgtaggacca tgctagggcc tgccaggag gggagtaccc caacctgcag ccccagggtg    25020
ggcttcctct gtttgctagg cacccaggct tgcacctgtg ctgtttccag cagcctctct    25080
cctatcctgt catgccctag tgtgaactgg agtccatttg acaagaactg ggagttttag    25140
aacctgggac tgtaggaaga gagaataacc ttagggccta ggtgttccag cccatttcac    25200
agggaggcaa gttgccccca agctcagttt tttgttttgt tttgttttgt ttgagatgta    25260
gtctcactct gttgcccagg ctagagtgca gtggcacgat cttggctcac tgcaacctcc    25320
gcctccttgg ttcaagcgat tcacctgcct cagcttctca gtagctggg attataggca    25380 cccaccacca cgcccagcta attttttgtat ttttagtaga cagggtttt caccatgttg    25440 gcccggctgt tcttgaactc ctgatctcag atgatccgcc cgcctcggcc tcccaaagtg    25500
ctgggattac aggtgtgagc caccgcaccc ggcccccaag ctcagtttga ccacaaatg    25560 ggactatgtt gctctagaaa tcaacatctt ttccacactg cattagtagc aacagagtct    25620
agaacaaagg aggccacagc cccactgaac tctcttctgc ttgaggtcac atctgccaca    25680
tcaggggtat ttacctcttt caacacatat ttattagggc acctgtctgg gccaggcgtt    25740
gtgctaaaac ccccaaacgc tgtcatatga tacaaagtgt tctgtaactt gcttggtttt    25800 ttttttttgtt tgtttgtttg ttttgttttg ttttttgttgt tgttttttttt tgcttcgcca    25860 tatattatag gaattttttt aggtcattat gacctcttta tttacttaat tatctatttta    25920 tttatttttac taatatttac agaaagggtc tcactctgtc acccaggctg gagtgcagtg    25980
gttgcaatca tagctcattg tagccttgaa ctcctgagct caagtgatct tcctacctcg    26040
gcctcctgag tagctgggac tacaggcaca agccaccatg cctggccgat attttttatgt    26100 tttgtagaga cggggtctca ctatgttgcc caggctggtc tcaaactcct gggctcaggt    26160
gatcctccct cctttgcctc ccaaagtatt gggattacac aagtgagcca ccttgctcag    26220
cctgacctca ttttttcaaag agctgcagag tgttacataa tgtattttaac tggtcacttt    26280 ttgatgacta ttaagttgtt ttcaggtttt ttgttattac agtgtcatat ccctgggca    26340 cagagcagtg ctggcacata gccagagctc aatcgataca tacctaatga atgaaagtac    26400
agtggacatc ctaattcagc cattcttttgc taacttgtgt acatacctgt ccagggtagg    26460
tccctagaat acagtcaata agtcagaagg tgtgagttgg gatctacctt ttggaaaggg    26520
```

```
atgttttcaa actacagtga gtcagaggag gatggcccag aagctggggg agttgaagct    26580
gatggcgtga aggaattagg ggtgttagga agaagcagga gataaagagc tagcttgcag    26640
aagaagtgtt agacttgtta tgggcaggta ctggagggta gctaaggact tgtgggtggc    26700
agttaccagg aagcgtatct gaactaagtg tcagaaaaag tgtcacaact gtaaattact    26760
cttgtcagtg agttcctgtc cttaaggggtt agggctgggt agccctctac tattctctaa    26820
gtctgtaatg taaagccact gaaaactctt gggttaagtt tggccatccc acccaaaaga    26880
tggaggcagg tccactttgc tgggaccagg agcccagtg aggccactct gggattgagt    26940
ggtcctgccc ctctggctgg gactgcagag ggaggaggac tgttagttca tgtctagaac    27000
acatatcagg tactcactga cactgtctgt tgactctttt ggccttttca gattctgggg    27060
caacagagtg ggtgacgagg gggcccaggc cctggctgaa gccttgggtg atcaccagag    27120
cttgaggtgg ctcaggtaag cttcagagtc tatcctgcag ttttcttggg gagatcaggt    27180
gaagagggag gagctggggc cagttctgaa ggtctttgaa cttttatttct accccacaat    27240 gttaggcaat ggagtaagga aaaagacca ttggatttca agagaggaca cttgagtctt    27300
tctgggtgac ttggaaatgt cccttgtcct ctcaggggttt tgatacagta tctgtaaatt    27360
gaagatattg ggctggatca ggtacatttt atcttaaggg ccaattccaa tccattggta    27420
gtgggtgccc agtgcaccac attaaaaaga attctaaggc tgcacctggg cttaaagaag    27480
agcactataa tcaattagtg atgtctaaaa aagctaaaaa aaaaaaaaa gagcactgca    27540 ttcaattagt gatgtctaaa aagggtagaa aaaaaaaaaa aaagaaaaaa gaaagagcac    27600
cgcaatcaat tagtgatgtc tgaaatggag cagaccagga gagcaccacg aattttgccc    27660
tccataggtt agctcatctc tgaggtcttt ccctgctctg acatacttt tgttccatgat    27720 tacctccagc ctggtgggga acaacattgg cagtgtgggt gcccaagcct tggcactgat    27780
gctggcaaag aacgtcatgc tagaagaact ctggtgagtt tgggggattc tctgctctgg    27840
ggaagtggat cacaatctct gttgatcccc tggcctcatc cataggagcg gttgtgtgga    27900
cagacaaagg tggatgattg agtgattgac tgattgattg attgtgtttg tctttatatg    27960
tactgagtgg tatgaagctt atagagcctg gtatgtacat gctaattttt ttatttaata    28020
aaatatatgg gtttgctggt ttggtgactg cctccacatg gcataagtgt taagagcaca    28080
gactctgtaa tcaagcaggc cgtgatctta ggcaagttaa ataacaattt cagaatctca    28140
agtttcatgt ctgtaaaatg agggtaagaa tacttccaac cataaaggat ttttgcaaga    28200
attagataaa gtagtgcctg tgaagacctt aatatagtgc ctggcatatt tgtaagtgct    28260
ccataaatgt taaattagaa taatggcagg gttactacta ctattactgc tgctgctgct    28320
gctgctgctg ctacaactac tatagtactg tgactactac tactaataaa gttttgttat    28380
tttaaagtga ttttgagttc ctaggagcac tgggtattca agtcttaggt cattttggaa    28440
ggtgtaatgg agttttgata gttgaaagag gaaccatgaa tcatgcttat actgttgacc    28500
tgaagcagat tctaagtttc tcatcccttta gatgccacta gtatagtttt ctgacatgtt    28560
ctgggcagct tcagattatg tcagggagat aaaatactga atgtttgatt ttcccgggaa    28620
gcagaaaggc actgcaacat atgggcattg ccataaacag attttatgga tggaccttgg    28680
ctgttgcagg gcttactagc tctactcaag tatgattgat tctatcctga ctggattttg    28740
ccacttggaa tttcttagta gaggagaacc ttgttatgag agcatcagtt atgattactg    28800
ttaaaagaaa aactttaggc aaattaaatt tagcagaact ggtttgaaca tacagcaatt    28860
```

```
tatgaattgg gcagcattca gaactgggag tgctccaccc agcaaggtag gcaagcagta   28920
tctatagaca ggaaaaggaa gtgatgtaca aaacagcttg attggttgca gctgggcatt   28980
tgccttatat gggcatggtg tgatgaggca ttttctttat atggatatag actgatcagc   29040
tggtagactg tgactgactg aagcctggct gctgtgattg gctaagactt agctgtttgt   29100
tataaggata tgttgttagg ttgcagtttg ctacatagga actcaaagta cagaggcagt   29160
ctcaggccaa atttagttta actatatgtt aagctgcagg tgacagaata cctccatcta   29220
tagaggttta aacaaggaaa gggtttattt tttcctgtat aggcagctgg atgtaggcag   29280
tgtagggttt gtacagtggc tacaagaggc caggaggggt ctcagctctg tctcattctc   29340
ttcctgttcc atcatcctta gcctgtaact tcattcacat ggttggttgt ctcatgatca   29400
caggatggct gctccaggtg cagcactact tctgtattcc cggattcgat ctatataccc   29460
aggaaagcca tctgggttct ctcctttaaa aagcattcct ggaagcccca cctgtcgact   29520
tccccttatg tatcaaccat gtgtatgtca cttgaccaac ccacttgtat gttgtttgac   29580
cagccctggc tgcaatggag agtgggaaat acagttttt caccaagtgc atggctgtcc   29640
aaatgaaatg agacttccat taataaggaa gaaaggaaag atggagatca ggaagctggg   29700
ggatcaggga acttattaca ttgagagccc ttggagtgaa ttctcttgca aatatgtccc   29760
tggaattgag aatccccaca acgtctttat ctgttctttc tttatccatg agtttgggtt   29820
ttcagatgtt ggatttccta tatggggggc atgtgagttc atcatcttcc ataatcaatg   29880
ttgtatcaac tggattttct ctcttcttct caccagcctg gaggagaacc atctccagga   29940
tgaaggtgta tgttctctcg cagaaggact gaagaaaaat tcaagtttga aaatcctgaa   30000
gtaaggaacc cataagcagg aaacaggaca ataattgctg gcctttggaa ggggcatttc   30060
tgattaagat ctgggccgct ctccgctggg ctaactcatg tgaggtggcc tggtagaaca   30120
gcttgccttg gtctaggtgg acaaggattc cagtgcaagt tgtttatctg ggaggtggtc   30180
ccagtaaatg ctgataggag agtggtgaag tgagatgggg aagtgaaggt aaccaataaa   30240
ggggagttat caagccagtt atcaatgagg gaaattggag ctcagtactc tggggcactc   30300
ctggagccag tgcagaacac acatggtcac ctacccaacc aatgggcaag aaagccatgg   30360
catttatcca ccaaccctct gtccttccta tgttgatgtg cgctcatggg gcactgattc   30420
tccagcactt ccagctcacc ctcacccagc tgaacatgct tctggggtca ggagaatggc   30480
ctcaggcaga gagtggcagg tcttctctgc aagcagtggc tggggaggtg atgtgatggg   30540
gagtactgtg gcctcctcca gtggctgact cagtggcttg ggacttgtgc cacaaagaga   30600
tggacagctc aggtgaacat gaacccacct agtgaccatc atgggtttgt cagggtgctc   30660
tctgaggctg atgccaaaat tcttatttca agtagacctc aggaaccccca tcagatggct   30720 ccttttgctg gaggaaagtg gcatctgcct aggcaaatgt ggtcctagga aaacgcttgc   30780
ctttagagac agacagacag acagctgcct ctgtgagtgc cagctttgct gccaggctgc   30840
tacccactct ggcgacactc atttgtgttg cttcacaag ctaggaagtt ccaaatatt   30900 tggagaaaac acttccacta attatttggg tggaaatggg ctgggaagtt ggggtgaagc   30960
ccggatgtgt ctgagccaga tgccagcttt gcactgaggg tcggcctttg gaataccaa   31020 gcccattatc aaccaggtgt ggatatggca ggtttgtctt ccctccttgt cacagcctta   31080
ctccacttga ctcccatgga tgccaggcaa tgaggctggg gttggtccca tgccaccctg   31140
tcatcagcct tattttcag catcctaaac tatatcatcc cccacaaaaa ttgaacttct   31200
gatatatctt ttataaaaaa gagaaatgcc tacatctttc ttttccagga ttagtttctg   31260
```

```
ccaagagttg gttgagagcc caggcttgct gggtgcagtg gctcacacct gtaatcccag   31320
cactttggga ggctgaggcg ggtggatcac ctgaggtggg gagttccata ccagcctgac   31380
caacatggag aaaccccatc tctactaaaa atacaaaatt agccgggcgt ggtggcatac   31440
acctgtaatc ccatctactc aggaagctga ggcaggagaa tcacttgaac ctgggaggtg   31500
gaggttgcca tgagccaaga tcacaccatt gcaccctaga ctggacaaga gagaaacttc   31560
catctcaaaa aaaaaaaaaa ggatgagaaa aataataatt taaaaaaaag agtccaggct   31620
ctggaaccag acagcctggg tcttacccct gctccaccat taccagccag ttcttcttgg   31680
atgagtgcct cagttgcctc aagtgtaaat ggagataatg gctggacctt cattataggc   31740
catgagcatt cactgagaga atgtagctaa caaagtgag ttgtaggttg gagcaaaagt   31800
aattgtggtt tcagaccatg aactttaaat tattataact aggctaaaat acatctttat   31860
taatcaaaat aggaaccatt aaaatcaaca cattttgcc aataagaaat aagtttgttt   31920
attcctgtag cataaaaatt catgcttcgg gattcaacaa actcttggaa agcattttct   31980
gcatcctcct ggttgtggaa gcattttcc tgcagaaagt tgtcaagatt cttgaagaaa   32040
tggtagtcag ttggctagag gtcaggtaaa tatggcggat gaggcaaaac ttcatagtcc   32100
aattcattca acttttgaag ctttggttgt gtgacatgca gtccggttgt tgtcgcggag   32160
aattggaccc tttctgttga cgaatgccgg ttgcaggtgt tgcagttttc agtgcatctc   32220
attgacttgc cgagcatact tctcatatgt aatggtttcg cagggattca gaaagctgta   32280
ggggatcaga ctagcagcag accaccagtg accatgacct tttttttttg gtgcgaattt   32340
gcctttggga agtgctttgg agcttcttct cggtccaacc actgagctag tcattgccag   32400
ttgtataaaa tccactttc atcgcacgtc acaatcagat caagaaatgg ttcgctgttg   32460
ttgtgtagaa taagagaaga tgacacttca aaatgacgat tttcttggtt ttcactcagc   32520
tcatgaggca cacacttatc gaggttttc accttttccaa tttgcttcaa atgctgaatg   32580
accatggaat ggtcgatgtt gagttctcaa gtagttgtaa gaaaatcagc tttgatgatt   32640
gctctcaatt ggtcattgtc agcttctgat ggcctgccag tacactcctc atcttcaagg   32700
ctcttatctc cttcgcaaaa cttcttgaac caccactgca ctatacgtta gttagcagtt   32760
cctgggccaa atgcattgct gatgttgtga gttgtctccg ctgctttaca acccattttg   32820
aattcaaata agaaaattgc ttgaatttgc tttttgtcta acatcatttt catagtctaa   32880
aataaatata aaataaacag aaagtattaa gtcattagca aaaaatcata aagtgagaat   32940
tgtgcattaa aatgatgtat agcataacca catttattta agaatgtatt ccaatatcaa   33000
atggcaaatt tcaacaatgc aaaaactgca attacttttg caccaatcta atagaagttc   33060
aataaatact ggcaattaca attggcattg ccttagggtc aacttgtaag acattcctga   33120
aattgtggga aaggggagg acctggagtg gacattattg gaaggcaaag ctgtaaccaa   33180
aagagcaacc tgggaaacac atgactcctc tgttgctgtc cctggcccta tcctgtctcc   33240
cctccctgtt gtcagctacc tcatatgttc tctaatctct gtctctgtgc cctcaaagac   33300 cccccctgaaa atagaaatat tactgctcat tggttatttt ctatcaatta agtactgtat   33360
tagtccgttt tcatgctgat gataaagata tacccaagac tgggcacttt atgaaagaaa   33420
gagttttatt gaacttacag ttccacgtgg ctggggaggt ctcacaatca tggctgaagg   33480
tgaaaggcac atctcacatg gcagcagaca ggagaagagg gcttgttcag ggaaactccc   33540 cttttttaaaa ccatcagata tcatgaaact tatttactgt aatgagaaca ggatgggatt   33600
```

```
caattacctt ccactgggtc gctcccacaa cacgtgggaa ttcaagagat ttgggtgggg   33660
acacagccaa accatatcaa gtactgtgca agtgttttag gcatgcagag agtggtgggt   33720
cttcccagca agcagagtgt ggggaggtaa tgggggactg gtggctgact taatggccca   33780
ggacccatgc cacaaggaga tggatggtgg atgtgaatag gagcctgctt acacccatca   33840
caatttagat tcttatgctc gatggcacgg gtactctttt aggcccattt taccaatgag   33900
gagattggga ctaatttgct cgagatcaaa aagaagtgg tgtaggtggg atttaaaccc    33960
aggatgtcta gcactaaaat gcaggtactt aaccactatc ctaagggagt ggctacttaa   34020
tttgataaac tcatctagtg aatggaagag agacggttac atttcactga tggtactgag   34080
cctttgttga tgagctcatt gggaatctca gacatgagca ggatgtgtct aagggacagg   34140
tgggcttcag tagactggct aactcctgca gtctctttaa ctggacagtt tcaagaggaa   34200
aaccaagaat ccttgaagct caccattgta tcttcttttc caggttgtcc aataactgca   34260
tcacctacct aggggcagaa gccctcctgc aggcccttga aaggaatgac accatcctgg   34320
aagtctggta aggcccctgg gcaggcctgt tttagctctc cgaacctcag tttttctatc   34380
tgtaaaatgg ggtgacggga gagaggaatg gcagaatttt gaggatccct tctgattctg   34440
acattcagtg agaatgattc tgcatgtgaa ggatctgatt ctctgtctaa gaagaagtc    34500
tttacctctt taagtaggga gcaatgattt cattttaaa ccttgactat ttattcagca    34560
acttctctgc tctatgagat agtgtaggaa tggggatgtg gttgaagaat gaaagaaaa    34620
gtcagctccc gccctcctag aaattgcatc tgccttcaca ggtcaaggat attggatcag   34680
accttctgcg gttctgaatg gagattacac aggttaggag caggttgcac agtgtttcca   34740
attctctata attaaagcca tagactttca tgtattgaaa aaagcaagaa ttgcattctt   34800
gacagattct ttcattgcct taaaagaat gactagcctt gggagtctgg gcagctgggt    34860
ccagtgttgt agactttctc tctgctgagc cacagcttca aagatttgtc cttcttgttt   34920
ccagggatct atttctcaga caataagtaa aggctttccc tggcctaatg tgctgtaagt   34980
gaatgctact atatatgttc caggcactgg gctagagact aatatttaaa gccaggaaa    35040
tttcctatag aaaatctata tctcaggbtt ttctcaaaag agctgggaac tctggatgcc    35100
cattcatgat tccagtagtt aaccagagta caagaagggc tgagtcttct cagatgggca   35160
aacccactct ggctgactgc agatccacca agcctattgt cttagaccag gaccctttgg   35220
caactcattc ccataagcct gtgacccttg ctttaaatat gcaggccttg tcttctctca   35280
aaaagcacat caaggctgca gcgaatgcag atatcaaatg atgaagttaa aaacaaaagc   35340
tttgctgggc gtggcagctc acacctgtaa tcctagcact ttgggaggct gaggcaggag   35400
gatcactta ggccagaggt tcaacaccag accttgtctc tcaaaaaata aaaaattcag    35460
ctgggtgcgg tgtagttcct agccacttgg gaggctggga tggaaggatc ccttgaaccc   35520
aggagttcaa ggctgcagtg ggccatgatt gcatcactgc acaggcgaca gaattagatc   35580
ccatctctta aaaaataaa aaatttaaaa gtgacttcaa aaatctatgc tgtgatggag    35640
agatttttcc ttctgtatga ttgtgatagc tctgtggcct atgacgtcat caggttctgg   35700
gcaaagtgta ggttttctgt ttcttttgttt ttgaaaccat tgcacagtcc taagaaacat  35760
cacattctgg gtcctgggca ccagccaaca tgaggtgagg gcaccagggt ttgctcattg   35820
cattcttgac agattctctt attgccttaa aagaatcac tggccttggg gagtctgtgg    35880
ctggctgggt gcagtgttgt ggactctctc tgcagagtca tggagccttg ttcagaatgc   35940
ttcctgagct gccctggttg gccaagggta aaaacagccc tgacttccct gcaagaaaca   36000
```

```
ctgcagctgg gccagagagt cagcccatcc caggcatggg tttaaaaagt ggaggctttt    36060
gtttgaaagc cctgctctaa ttttgtcctc actcaaacct ctgttcactt gatctgcttt    36120
aggctccgag ggaacacttt ctctctagag gaggttgaca agctcggctg cagggacacc    36180
agactcttgc tttgaagtct ccgggaggat gttcgtctca gtttgtttgt gagcaggctg    36240
tgagtttggg ccccagaggc tgggtgacat gtgttggcag cctcttcaaa atgagccctg    36300
tcctgcctaa ggctgaactt gttttctggg aacaccatag gtcacctttta ttctggcaga    36360 ggagggagca tcagtgccct ccaggataga cttttcccaa gcctacttttt gccattgact    36420 tcttcccaag attcaatccc aggatgtaca aggacagccc ctcctccata gtatgggact    36480
ggcctctgct gatcctccca ggcttccgtg tgggtcagtg gggcccatgg atgtgcttgt    36540
taactgagtg cctttggtg gagaggcccg gcctctcaca aaagaccect taccactget     36600 ctgatgaaga ggagtacaca gaacacataa ttcaggaagc agctttcccc atgtctcgac    36660
tcatccatcc aggccattcc ccgtctctgg ttcctcccct cctcctggac tcctgcacac    36720
gctccttcct ctgaggctga aattcagaat attagtgacc tcagctttga tatttcactt    36780
acagcacccc caaccctggc acccaggggtg ggaagggcta caccttagcc tgccctcctt   36840
tccggtgttt aagacatttt tggaaggggga cacgtgacag ccgtttgttc cccaagacat   36900
tctaggtttg caagaaaaat atgaccacac tccagctggg atcacatgtg gacttttatt   36960
tccagtgaaa tcagttactc ttcagttaag cctttggaaa cagctcgact ttaaaaagct    37020
ccaaatgcag cttttaaaaaa ttaatctggg ccagaatttc aaacggcctc actaggcttc    37080
tggttgatgc ctgtgaactg aactctgaca acagacttct gaaatagacc cacaagaggc    37140
agttccattt catttgtgcc agaatgcttt aggatgtaca gttatggatt gaaagtttac    37200
aggaaaaaaa attaggccgt tccttcaaag caaatgtctt cctggattat tcaaaatgat    37260
gtatgttgaa gcctttgtaa attgtcagat gctgtgcaaa tgttattatt ttaaacatta    37320
tgatgtgtga aaactggtta atatttatag gtcactttgt tttactgtct taagtttata    37380
ctcttataga caacatggcc gtgaactttta tgctgtaaat aatcagaggg gaataaactg    37440
ttg                                                                   37443
```

<210> SEQ ID NO 4
<211> LENGTH: 1315
<212> TYPE: DNA
<213> ORGANISM: Homo sapiens
<220> FEATURE:
<221> NAME/KEY: CDS
<222> LOCATION: (117)..(1118)

<400> SEQUENCE: 4

```
cgatcagaag caggtcacac agcctgtttc ctgttttcaa acggggaact tagaaagtgg     60
cagcccctcg gcttgtcgcc ggagctgaga accaagagct cgaaggggcc atatga cac    119
                                                                His
                                                                 1 tcc tcc cgg acc cct gga cac aca cag ccc tgg aga ctg gag cct tgg      167
Ser Ser Arg Thr Pro Gly His Thr Gln Pro Trp Arg Leu Glu Pro Trp
        5                  10                 15 agc atg gca agt cca gag cac cct ggg agc cct ggc tgc atg gga ccc      215
Ser Met Ala Ser Pro Glu His Pro Gly Ser Pro Gly Cys Met Gly Pro
    20                 25                  30 ata acc cag tgc acg gca agg acc cag cag gaa gca cca gcc act ggc      263
Ile Thr Gln Cys Thr Ala Arg Thr Gln Gln Glu Ala Pro Ala Thr Gly
 35                 40                  45 ccc gac ctc ccg cac cca gga cct gac ggg cac tta gac aca cac agt      311
```

|  |  |  |  |  |  |  |  |  |  |  |  |  |  |  |
|---|---|---|---|---|---|---|---|---|---|---|---|---|---|---|
| Pro | Asp | Leu | Pro | His | Pro | Gly | Pro | Asp | Gly | His | Leu | Asp | Thr | His | Ser |
| 50 |  |  |  | 55 |  |  |  | 60 |  |  |  | 65 |

```
ggc ctg agc tcc aac tcc agc atg acc acg cgg gag ctt cag cag tac      359
Gly Leu Ser Ser Asn Ser Ser Met Thr Thr Arg Glu Leu Gln Gln Tyr
                70                  75                  80 tgg cag aac cag aaa tgc cgc tgg aag cac gtc aaa ctg ctc ttt gag      407
Trp Gln Asn Gln Lys Cys Arg Trp Lys His Val Lys Leu Leu Phe Glu
                85                  90                  95 att gct tca gct cgc atc gag gag aga aaa gtc tct aag ttt gtg gtg      455
Ile Ala Ser Ala Arg Ile Glu Glu Arg Lys Val Ser Lys Phe Val Val
                100                 105                 110 tac caa atc atc gtc atc cag act ggg agc ttt gac aac aac aag gcc      503
Tyr Gln Ile Ile Val Ile Gln Thr Gly Ser Phe Asp Asn Asn Lys Ala
            115                 120                 125 gtc ctg gaa cgg cgc tat tcc gac ttc gcg aag ctc cag aaa gcg ctg      551
Val Leu Glu Arg Arg Tyr Ser Asp Phe Ala Lys Leu Gln Lys Ala Leu
130                 135                 140                 145 ctg aag acg ttc agg gag gag atc gaa gac gtg gag ttt ccc agg aag      599
Leu Lys Thr Phe Arg Glu Glu Ile Glu Asp Val Glu Phe Pro Arg Lys
                150                 155                 160 cac ctg act ggg aac ttc gct gag gag atg atc tgt gag cgt cgg cgc      647
His Leu Thr Gly Asn Phe Ala Glu Glu Met Ile Cys Glu Arg Arg Arg
                165                 170                 175 gcc ctg cag gag tac ctg ggc ctg ctc tac gcc atc cgc tgc gtg cgc      695
Ala Leu Gln Glu Tyr Leu Gly Leu Leu Tyr Ala Ile Arg Cys Val Arg
            180                 185                 190 cgc tcc cgg gag ttc ctg gac ttc ctc acg cgg ccg gag ctg cgc gag      743
Arg Ser Arg Glu Phe Leu Asp Phe Leu Thr Arg Pro Glu Leu Arg Glu
195                 200                 205 gct ttc ggc tgc ctg cgg gcc ggc cag tac ccg cgc gcc ctg gag ctg      791
Ala Phe Gly Cys Leu Arg Ala Gly Gln Tyr Pro Arg Ala Leu Glu Leu
210                 215                 220                 225 ctg ctg cgc gtg ctg ccg ctg cag gag aag ctc acc gcc cac tgc cct      839
Leu Leu Arg Val Leu Pro Leu Gln Glu Lys Leu Thr Ala His Cys Pro
                230                 235                 240 gcg gcc gcc gtc ccg gcc ctg tgc gcc gtg ctg ctg tgc cac cgc gac      887
Ala Ala Ala Val Pro Ala Leu Cys Ala Val Leu Leu Cys His Arg Asp
                245                 250                 255 ctc gac cgc ccc gcc gag gcc ttc gcg gcc gga gag agg gcc ctg cag      935
Leu Asp Arg Pro Ala Glu Ala Phe Ala Ala Gly Glu Arg Ala Leu Gln
                260                 265                 270 cgc ctg cag gcc cgg gag ggc cat cgc tac tat gcg cct ctg ctg gac      983
Arg Leu Gln Ala Arg Glu Gly His Arg Tyr Tyr Ala Pro Leu Leu Asp
275                 280                 285 gcc atg gtc cgc ctg gcc tac gcg ctg ggc aag gac ttc gtg act ctg     1031
Ala Met Val Arg Leu Ala Tyr Ala Leu Gly Lys Asp Phe Val Thr Leu
290                 295                 300                 305 cag gag agg ctg gag gag agc cag ctc cgg agg ccc acg ccc cga ggc     1079
Gln Glu Arg Leu Glu Glu Ser Gln Leu Arg Arg Pro Thr Pro Arg Gly
                310                 315                 320 atc acc ctg aag gag ctc act gtg cga gaa tac ctg cac tgagccggcc     1128
Ile Thr Leu Lys Glu Leu Thr Val Arg Glu Tyr Leu His
                325                 330 tgggaccccg cagggacgct ggagatttgg ggtcaccatg gctcacagtg ggctgtttgg   1188
ggttcttttt ttttattttt ccttttcttt tttgttattt gagacagtct tgctctgtca   1248
cccagactga agtgcagtgg ctcaattatg tctcactgca gcctcaaact cctgggcaca   1308
agcaatc                                                             1315
```

<210> SEQ ID NO 5
<211> LENGTH: 334
<212> TYPE: PRT
<213> ORGANISM: Homo sapiens

<400> SEQUENCE: 5

```
His Ser Ser Arg Thr Pro Gly His Thr Gln Pro Trp Arg Leu Glu Pro
 1               5                  10                  15
Trp Ser Met Ala Ser Pro Glu His Pro Gly Ser Pro Gly Cys Met Gly
            20                  25                  30
Pro Ile Thr Gln Cys Thr Ala Arg Thr Gln Gln Glu Ala Pro Ala Thr
        35                  40                  45
Gly Pro Asp Leu Pro His Pro Gly Pro Asp Gly His Leu Asp Thr His
    50                  55                  60
Ser Gly Leu Ser Ser Asn Ser Ser Met Thr Thr Arg Glu Leu Gln Gln
65                  70                  75                  80
Tyr Trp Gln Asn Gln Lys Cys Arg Trp Lys His Val Lys Leu Leu Phe
                85                  90                  95
Glu Ile Ala Ser Ala Arg Ile Glu Glu Arg Lys Val Ser Lys Phe Val
            100                 105                 110
Val Tyr Gln Ile Ile Val Ile Gln Thr Gly Ser Phe Asp Asn Asn Lys
        115                 120                 125
Ala Val Leu Glu Arg Arg Tyr Ser Asp Phe Ala Lys Leu Gln Lys Ala
    130                 135                 140
Leu Leu Lys Thr Phe Arg Glu Glu Ile Glu Asp Val Glu Phe Pro Arg
145                 150                 155                 160
Lys His Leu Thr Gly Asn Phe Ala Glu Glu Met Ile Cys Glu Arg Arg
                165                 170                 175
Arg Ala Leu Gln Glu Tyr Leu Gly Leu Leu Tyr Ala Ile Arg Cys Val
            180                 185                 190
Arg Arg Ser Arg Glu Phe Leu Asp Phe Leu Thr Arg Pro Glu Leu Arg
        195                 200                 205
Glu Ala Phe Gly Cys Leu Arg Ala Gly Gln Tyr Pro Arg Ala Leu Glu
    210                 215                 220
Leu Leu Leu Arg Val Leu Pro Leu Gln Glu Lys Leu Thr Ala His Cys
225                 230                 235                 240
Pro Ala Ala Val Pro Ala Leu Cys Ala Val Leu Leu Cys His Arg
                245                 250                 255
Asp Leu Asp Arg Pro Ala Glu Ala Phe Ala Ala Gly Glu Arg Ala Leu
            260                 265                 270
Gln Arg Leu Gln Ala Arg Gly His Arg Tyr Tyr Ala Pro Leu Leu
        275                 280                 285
Asp Ala Met Val Arg Leu Ala Tyr Ala Leu Gly Lys Asp Phe Val Thr
    290                 295                 300
Leu Gln Glu Arg Leu Glu Ser Gln Leu Arg Arg Pro Thr Pro Arg
305                 310                 315                 320
Gly Ile Thr Leu Lys Glu Leu Thr Val Arg Glu Tyr Leu His
                325                 330
```

<210> SEQ ID NO 6
<211> LENGTH: 8135
<212> TYPE: DNA
<213> ORGANISM: Homo sapiens
<220> FEATURE:
<221> NAME/KEY: exon
<222> LOCATION: (1)..(161)
<220> FEATURE:
<221> NAME/KEY: exon
<222> LOCATION: (3812)..(3950)
<220> FEATURE:
<221> NAME/KEY: exon
<222> LOCATION: (5426)..(5577)
<220> FEATURE:
<221> NAME/KEY: exon
<222> LOCATION: (7273)..(8135)

<400> SEQUENCE: 6

```
cgatcagaag caggtcacac agcctgtttc ctgttttcaa acggggaact tagaaagtgg      60
cagcccctcg gcttgtcgcc ggagctgaga accaagagct cgaagggcc atatgacact      120 cctcccggac ccctggacac acacagccct ggagactgga ggtcagtatt tgatcccaag     180
ctcagctgtc ctctgcctgc tgtggcctga gtcccttct cctggggccc tgcctggcac      240
```

```
ctgctggggg cagggtggga gggggaagag ttagtgacag ccgctgtgtc tggagctctc      300
cttagcacac tgaggcagag gaagggacag ctcctggacc ttccatcacc tccattcctt      360
ttgaaatgct aggcgcttgt acaacccatc ttgggcctgg agaataagtc accacacctg      420
tgtttctcaa aagaacagtg tcagggaacc cctgcctcag cacagcctta gaggactcat      480
ggaaaatgca gaatccaggc ctgttcaatg gcaccttcct atgttagcag ccaggaaacc      540
tgctcttgga caagccctg ggatcccacc cccaccccac caggggattc ttacacacac      600
tgggttggga gccctggct ttggcaaggc ttctcaggtg agcgtccagt tgttggaggg      660
tacccaccct ttccccaaga gaggcagcca cacatccaac atcctgggat ctctgtctcc      720
cagcgtgggc catgtgcttt atttcacccc ctagaggctc atccccatg aaaagtcctc      780
cgcaggccct cagaaagata gtgtggcctc tgtgtgccca gcagaagaag gactggactt      840
ggcagtcagc tcttggagag ggggtggtta ggacacctgg ggacaggagg aggagaatga      900
ctgtctgtgc acacacggct ggaaggtaca ggaggctggg aagctgctct gtcccctggg      960
ccaactacag gcccccaggc caacagcaac aacactttta gtattttgtt ataaagtcaa     1020
gaaatctttg ctacagaggg tgaggagagg gaaggaaagg gccatggaac cgtctatgtg     1080
gctatcccca gagagctttt agagtgacag gattgctttc ccatttcaca gatgaggaaa     1140
ctgaggcctg gagagggatg ggaagctacc caaggcccca tggatacacc agtgcacaac     1200
tctttccttc cccctcctct ttaaatgggt gattcccaat gaaacctgta agagacaacc     1260
ataagggagc tgactgtggc tgctgaattt gattttattc taaggcctgg ttttataatc     1320
agctttctca gtctttactg gagtgtcaag ccgaggcatc atttctaggg tcttacaggg     1380
tctctgggcc aatagtgccc tgcttctgac ctggagccag ctgcctggtc atgaaagcag     1440
atctgcaaag gctggggccc ctgaggccaa ggccactcgc catcacccat tttacagaag     1500
tgctgagcat aggagtgccc tgggccccca gaatcccag ccaccaagaa tcacgtaaac     1560
catccactgt ctcacttagg caccagtcag aatgtaggga acccacccct agtcatccat     1620
catcttatca acaggacggg gcttgtagcc acatttatca ggtagggaaa ctgaagccta     1680
gagatattaa agcacttgct taaggacaca cggttggtca ggatggaagg cgatgtctcc     1740
tgactccctg acaggcacaa gagacaagcg agaggtgccc gtgacggcat gctcaagaac     1800
gtgcagccct gggccagcca ggccctgct ccgtgcctct gtttgcccat ctgtaaaagg     1860
tgaggttgga tcgagggtcc ctgagggccg cccactggat ggctgtgcag agccaaacgg     1920
agaaggcccc agggttcctt tcacccgaca cagcaagcac ttccccctga agtgcaggct     1980
ccaggcccca gctgacctcc cctctcccag gccagcggct ctcaccccct gagcaaggga     2040
caggcgctgg ctgtgctcag ggacatgcat gactcccgcc cccatctgtg ctcagggggt     2100
gccagggagg cactggctct atctttctct aggccgtagt cagcccaggg gttcagacca     2160
agagcccaga atccaacaga tcagagttca agtcccagct ctacctctat gttccactgg     2220
cagcttcctc aggtcatttg caccttcctt gtcttgaatt tccatgccta accagtatac     2280
cagctactcc ctccagccga tctaatgttt taattgtccc tttctctaag ttgtctcaaa     2340
catttgtaat tctattccaa tccaccttaa tttagtcatt tatttcacaa atatttctgg     2400
aaacatctag cacttaacag acactaaaag cgggggtact acacagtccc tgggatggac     2460
agggccctga gctgaggctt cagagtctgc ctgactgaat cctcacccca gccttgtgaa     2520
cgtgggttct gttattatcc ccaatttata ggaaacagaa gcacagagaa gttgagtcac     2580
ttgccagcta ccaggtcatc ccttccactt atccgggtca cagacagagt tattatgtaa     2640
```

```
accagatccc agctgcctgt tctccctccc tgagtaaggt ggagagaatt ctgaagtcag    2700
cccagcctgg gtctgtatcc tgcccaccac tcaccagctc ctcatctttg caactctaa    2760 gtctcagttc ccttatcata aaagggagat gtaaacagtc ctgagtgcag acagtgttca    2820
ggttagtgca agagtgtgtg ctgggtgtga agtgcacagc cagcacgtca caagcactgg    2880
agacaaattc agctttgctt gttgcgcaca ctcaccagct gcgtgacttt agacctcagt    2940
tttctcatct gttatgtggt ggtaatgata gacttttgtg agcattaaac tagattaggg    3000
gctatggaga acctagatgg gtatgaagtg ggtataataa gctatcagtt aattttgctg    3060
atagatagat tattgattga ttgatcgata gaagattcat accagtatct acctgctctg    3120
aacactgacc tttctttttt tcttttggag atggtcttgt tctgtcaccc agactggagt    3180
gcagtggcat catcatagct cactgcagcc tcagtctctt gggcttaagg gatcctcctg    3240
tctcagcctc ccaagtagct gggaccacag gcgtgcatcc tggataattt ttttttattt    3300
tttctagaga cggggtctca ctacattggc caggctggtc tcaaattcct gggctcaagt    3360
gatccttcta acccagcctc ccaaagcgct gggattacag gcatgagtgg ccatgttcaa    3420
cttgaacact gagacttcat tcgcatgtgt aacataaaac tgagtatcta gacaagccag    3480
catctttctt tcaagtaatc actaaagcca atacttttac ttgaaatcat ctcatttaaa    3540
actctgagca atacgtaagg atcacctcaa taacatatgg atcatcgcaa taggtgaagg    3600
gtcttctctg ccttggagta acctgcccag caaaggggca gacccagatt tgggatctgg    3660
cagctgggag agtggggaag gttgagccgt ggggcccttg tcattccctc tgcctgccag    3720 gaggggcat gacacagctc ctaggcaccc caggagccac cgggaacccc aactggagtg    3780
ggtcctcact gttctctttt tcctctggca gccttggagc atggcaagtc cagagcaccc    3840
tgggagccct ggctgcatgg gacccataac ccagtgcacg gcaaggaccc agcaggaagc    3900
accagccact ggccccgacc tcccgcaccc aggacctgac gggcacttag gtgggcttga    3960
ggcttgagac tcggtctggg ggagaggtct gaagacattc aaagtacaaa tgtgggtcac    4020
tttgggggat gcagcaagag gcccgggcag ctcttgtaac ttgggttatc ccaaaacaga    4080
cactgagaca cagatctagt gcaagctgtt tatccgggag acggtcctag gagtcatggc    4140
aggggagtgg gaatgaaagg aaagggcaag aggccagggc aggacatcag tgaacagata    4200
ggcacggtag gtggctgaag ctcaaccccca gcggggggtct tctgggagac cctgaacat    4260 atctctgggt tgtcctatcc taggggtgag gaagccgggc tgttatctac cagtcctgcc    4320
ctgcatagga gaagggacgc tcctgggcct gctgctatgg ccctagaaag ccctcaggga    4380
agccagtggc atgttctgga aaagtgggtg ccaagagggc acggtccagc ctggggcatg    4440
gacagcatct gctgtagtgc catctcctgg aacagatctt ttcttacagt ccttcgagat    4500
gccctattca atacctgctc tgttcctggc cctatgcagg gcactggaga acagaaaca    4560 ggaagaaatc aaaacactgca ctagtcctga ggtttggtag agaaacagat cagtgagaaa    4620
cagttacacg tgccacgaga aataaataaa taaaatgaaa aacctgtagg aacaaggtgg    4680
gaagctctta ctctaatgcc aaggggcatt tgcagtgatg tggggctgg gtcttgaagg    4740 gtagactgga aaagggctgg gacccatgcc ctttgcaata aaatgcacaa ttatttgtgc    4800
ttcttaagaa cctcagagtg gcgcagggct caagtggggt ttaagaaaca ctgtgttcgt    4860
tttccaggcg tggaaataga gggttggatg caaggcagag cagtgcacgt ccagaaagag    4920
cccggcatgt gggcagttag atgagaaggt taggaagggc cagcccgctg aggctggaac    4980
```

```
ataacatcct cctcactgcc tccctgccc actgatgtgt gctcaaggag tcgtggcaac    5040
agtcacgaag tcagggctgc agggagcaca gaaacacaca agccaccgtc tctgcttgtc    5100
cagagcaggg atttcaccat ggccaatcta cagaccagaa gtggacgatg caaagtgccc    5160
gcaccgcatt ccaaagctgt gaaaccactt ggggtgatg ggctatttgg gattgtcggt      5220
ggtagggtgg attctgccag gctgggcaca gaggtctgtc tgatgcccca attgggccta    5280
taaatggcgg ggtgggagag agggatattc aatactcttc aggagttctg atatgccatc    5340
tcagatagac ccagccatct ccccaagccc atgcctcgga agtgcactga cagggtgcag    5400
atccttaagg gtgttgtcct tccagacaca cacagtggcc tgagctccaa ctccagcatg    5460
accacgcggg agcttcagca gtactggcag aaccagaaat gccgctggaa gcacgtcaaa    5520
ctgctctttg agatcgcttc agctcgcatc gaggagagaa aagtctctaa gtttgtggta    5580
agcagagatt gggaaatggt ggagcctctt tcactctgct tccttcctgg ccctgaataa    5640
gtcttgtaga gcctcaggtt tcccaactat gaaatgggtc aacacactaa ctcacagctt    5700
tcttctggag aaaatggcca aagagcaaga tttcaggctc agcacctgct agggtctgtg    5760
aggattcgaa ccatataagt catatttctt ggtcccaaga aggaaatagc ccagtttaat    5820
cccatcttat caggtgtcag tcacctgtgt cctttcttca ccaattttgc catatcactg    5880
tatctgttct aattattatt acttattttt ttctttaaat tggatcactt tttaaaaaca    5940
tgaagcacat ttatttcaaa gagaaatacc ttaaatggaa aaccaatatc acatggcaca    6000
aagcaaaagt aacatactag aaaagtcgat acaaggaaag tcaatacaag gaaagctatg    6060
tgctgttatt aaattctagc tggttactgt ggcttcggga aagccctgtg cctgggagct    6120
gctcctctcc ctgttagaat ggaatttag cttgtgttaa gggatgttaa agactgccta    6180
agagccacac ttcatccttc tccttcactt acctgggacc gggataaata acatagctac    6240
cactgaatgc caatggcatg ccgggcacag ctccatgtgg tttcagtgca ttaactcatt    6300
taatcctcac tgggtgaggt aggcactatg cctatccttg ttttatgaat gagaaaagtg    6360
agactcggag aggttaaatt actcatctaa aaccacacag ctagaccatg gtagggctat    6420
aattacaacc catgcaatct ggctctggag tcagatgcat gggttataat tgcccttaat    6480
atataattgc ccgtaatcag gattctcttg aaagatgatt gaaaaggatt gattttctta    6540
ccatataacg gcatcaccag tgtacctaaa tgatgttata ttgtacgtaa aactaattcc    6600
caagtgtgaa acatttggaa aacacagcat ctcagttcag aaaacagagg cccagtttta    6660
gcaagtaaag ccaagaggga ccccagcagc ctgcagggca ggaccctctg ccctttctcc    6720
tcccagatgt ccccaccttg ctgtgttgtt gttccagggt tgactcagct gatgccaata    6780
gcaatttaaa acagaattgg gccaggtgca gtggctcatg cctgtaatcc cagcactttg    6840
ggaggcccag gtaggaggat cgcttgagcc caggagttgg agaccagcct gggcaacaca    6900
gccagacccc atcttttaaa aagaatcaaa aaatctgcca ggtagtgggt gtgcctgtag    6960
tcccagctac tcaggaggct caggtgggca ggtcaattga gcccataagt tcaaggttgc    7020
agtgaggtat gatcgcatca ctgtactcca gcctgggtaa cagtgcgaga ccctgtctct    7080
aaaaataaat aaataaataa ataaataaat aaataaacaa acaaacaaac aaacaaacaa    7140
tcaattgcat ataaggatcg cccgttttca gggcatgctt tacaccggcc tggttaactt    7200
tactctgggt gtgctccgtc cgccgcagcc ccgccgggga ggtggccaca gctctctctg    7260
gttgcgccct aggtgtacca aatcatcgtc atccagactg ggagctttga caacaacaag    7320
gccgtcctgg aacggcgcta ttccgacttc gcgaagctcc agaaagcgct gctgaagacg    7380
```

```
ttcagggagg agatcgaaga cgtggagttt cccaggaagc acctgactgg gaacttcgct     7440
gaggagatga tctgtgagcg tcggcgcgcc ctgcaggagt acctgggcct gctctacgcc     7500
atccgctgcg tgcgccgctc ccgggagttc ctggacttcc tcacgcggcc ggagctgcgc     7560
gaggctttcg gctgcctgcg ggccggccag tacccgcgcg ccctggagct gctgctgcgc     7620
gtgctgccgc tgcaggagaa gctcaccgcc cactgccctg cggccgccgt cccggccctg     7680
tgcgccgtgc tgctgtgcca ccgcgacctc gaccgccccg ccgaggcctt cgcggccgga     7740
gagagggccc tgcagcgcct gcaggcccgg gagggccatc gctactatgc gcctctgctg     7800
gacgccatgg tccgcctggc ctacgcgctg ggcaaggact tcgtgactct gcaggagagg     7860
ctggaggaga gccagctccg gaggcccacg ccccgaggca tcaccctgaa ggagctcact     7920
gtgcgagaat acctgcactg agccggcctg ggaccccgca gggacgctgg agatttgggg     7980
tcaccatggc tcacagtggg ctgtttgggg ttcttttttt ttattttttcc tttttctttt     8040 tgttatttga cacagtcttg ctctgtcacc cagactgaag tgcagtggct caattatgtc     8100
tcactgcagc ctcaaactcc tgggcacaag caatc                                8135

<210> SEQ ID NO 7
<211> LENGTH: 16
<212> TYPE: DNA
<213> ORGANISM: Homo sapiens

<400> SEQUENCE: 7
ctgggtgcga ttgctc                                                        16

<210> SEQ ID NO 8
<211> LENGTH: 16
<212> TYPE: DNA
<213> ORGANISM: Homo sapiens

<400> SEQUENCE: 8
ccaggcccca tgacag                                                        16

<210> SEQ ID NO 9
<211> LENGTH: 25
<212> TYPE: DNA
<213> ORGANISM: Homo sapiens

<400> SEQUENCE: 9
tggtcccggc ccaatcccaa tgctt                                              25

<210> SEQ ID NO 10
<211> LENGTH: 28
<212> TYPE: DNA
<213> ORGANISM: Homo sapiens

<400> SEQUENCE: 10
ttcctcatgt ataaattggg tgtggcca                                           28

<210> SEQ ID NO 11
<211> LENGTH: 25
<212> TYPE: DNA
<213> ORGANISM: Homo sapiens

<400> SEQUENCE: 11
acagagtgag gacccccatct ctatc                                             25

<210> SEQ ID NO 12
```

```
<211> LENGTH: 25
<212> TYPE: DNA
<213> ORGANISM: Homo sapiens

<400> SEQUENCE: 12
tccaactgct gggattacag gcaca                                              25

<210> SEQ ID NO 13
<211> LENGTH: 22
<212> TYPE: DNA
<213> ORGANISM: Homo sapiens

<400> SEQUENCE: 13
agtccccgag accagggcaa ac                                                 22

<210> SEQ ID NO 14
<211> LENGTH: 23
<212> TYPE: DNA
<213> ORGANISM: Homo sapiens

<400> SEQUENCE: 14
tccatttctg cagtacacat gca                                                23

<210> SEQ ID NO 15
<211> LENGTH: 20
<212> TYPE: DNA
<213> ORGANISM: Homo sapiens

<400> SEQUENCE: 15
ctctccccat agaaggcatc                                                    20

<210> SEQ ID NO 16
<211> LENGTH: 20
<212> TYPE: DNA
<213> ORGANISM: Homo sapiens

<400> SEQUENCE: 16
ggatagagac gttctcttaa                                                    20

<210> SEQ ID NO 17
<211> LENGTH: 20
<212> TYPE: DNA
<213> ORGANISM: Homo sapiens

<400> SEQUENCE: 17
caggctgaat gacagaacaa                                                    20

<210> SEQ ID NO 18
<211> LENGTH: 20
<212> TYPE: DNA
<213> ORGANISM: Homo sapiens

<400> SEQUENCE: 18
attgaaaaca actccgtcca                                                    20

<210> SEQ ID NO 19
<211> LENGTH: 25
<212> TYPE: DNA
<213> ORGANISM: Homo sapiens

<400> SEQUENCE: 19
atactcactt ttagacagtt caggg                                              25
```

```
<210> SEQ ID NO 20
<211> LENGTH: 21
<212> TYPE: DNA
<213> ORGANISM: Homo sapiens

<400> SEQUENCE: 20
ggctcagttc ctaaccagtt c                                              21

<210> SEQ ID NO 21
<211> LENGTH: 20
<212> TYPE: DNA
<213> ORGANISM: Homo sapiens

<400> SEQUENCE: 21
agtcagtctg tccagaggtg                                                20

<210> SEQ ID NO 22
<211> LENGTH: 20
<212> TYPE: DNA
<213> ORGANISM: Homo sapiens

<400> SEQUENCE: 22
tgaatcttac atcccatccc                                                20

<210> SEQ ID NO 23
<211> LENGTH: 17
<212> TYPE: DNA
<213> ORGANISM: Homo sapiens

<400> SEQUENCE: 23
gatcttccca aagcgcc                                                   17

<210> SEQ ID NO 24
<211> LENGTH: 17
<212> TYPE: DNA
<213> ORGANISM: Homo sapiens

<400> SEQUENCE: 24
tcccgtcagc caagcta                                                   17

<210> SEQ ID NO 25
<211> LENGTH: 20
<212> TYPE: DNA
<213> ORGANISM: Homo sapiens

<400> SEQUENCE: 25
aagcttgtat ctttctcagg                                                20

<210> SEQ ID NO 26
<211> LENGTH: 20
<212> TYPE: DNA
<213> ORGANISM: Homo sapiens

<400> SEQUENCE: 26
atctaccttg gctgtcattg                                                20

<210> SEQ ID NO 27
<211> LENGTH: 20
<212> TYPE: DNA
<213> ORGANISM: Homo sapiens

<400> SEQUENCE: 27
cctccataat catgtgagcc                                                20
```

-continued

```
<210> SEQ ID NO 28
<211> LENGTH: 20
<212> TYPE: DNA
<213> ORGANISM: Homo sapiens

<400> SEQUENCE: 28
aatctcccca actcaagacc                                                  20

<210> SEQ ID NO 29
<211> LENGTH: 20
<212> TYPE: DNA
<213> ORGANISM: Homo sapiens

<400> SEQUENCE: 29
ggatgcctgc tctaaatacc                                                  20

<210> SEQ ID NO 30
<211> LENGTH: 19
<212> TYPE: DNA
<213> ORGANISM: Homo sapiens

<400> SEQUENCE: 30 cccagggtc aaacttaat                                                    19

<210> SEQ ID NO 31
<211> LENGTH: 21
<212> TYPE: DNA
<213> ORGANISM: Homo sapiens

<400> SEQUENCE: 31
ggtttgaaag tatctccagg g                                                21

<210> SEQ ID NO 32
<211> LENGTH: 21
<212> TYPE: DNA
<213> ORGANISM: Homo sapiens

<400> SEQUENCE: 32
ggtttgaaag tatctccagg g                                                21

<210> SEQ ID NO 33
<211> LENGTH: 20
<212> TYPE: DNA
<213> ORGANISM: Homo sapiens

<400> SEQUENCE: 33
gtgcatgtgt tcgtatcaac                                                  20

<210> SEQ ID NO 34
<211> LENGTH: 20
<212> TYPE: DNA
<213> ORGANISM: Homo sapiens

<400> SEQUENCE: 34
tcatctccaa aggagtttct                                                  20

<210> SEQ ID NO 35
<211> LENGTH: 18
<212> TYPE: DNA
<213> ORGANISM: Homo sapiens

<400> SEQUENCE: 35
aaagccaacc ttgcttca                                                    18
```

-continued

```
<210> SEQ ID NO 36
<211> LENGTH: 20
<212> TYPE: DNA
<213> ORGANISM: Homo sapiens

<400> SEQUENCE: 36
tcttggaaac aggtaagtgc                                                 20

<210> SEQ ID NO 37
<211> LENGTH: 18
<212> TYPE: DNA
<213> ORGANISM: Homo sapiens

<400> SEQUENCE: 37
attgccctca agaacagc                                                   18

<210> SEQ ID NO 38
<211> LENGTH: 17
<212> TYPE: DNA
<213> ORGANISM: Homo sapiens

<400> SEQUENCE: 38
gtgctatgcc atcccag                                                    17

<210> SEQ ID NO 39
<211> LENGTH: 20
<212> TYPE: DNA
<213> ORGANISM: Homo sapiens

<400> SEQUENCE: 39
ccacaccagc gttttctaa                                                  20

<210> SEQ ID NO 40
<211> LENGTH: 24
<212> TYPE: DNA
<213> ORGANISM: Homo sapiens

<400> SEQUENCE: 40
cacactttac acacacctat accc                                            24

<210> SEQ ID NO 41
<211> LENGTH: 22
<212> TYPE: DNA
<213> ORGANISM: Homo sapiens

<400> SEQUENCE: 41
aagccatatt aggtctgtcc at                                              22

<210> SEQ ID NO 42
<211> LENGTH: 19
<212> TYPE: DNA
<213> ORGANISM: Homo sapiens

<400> SEQUENCE: 42
gcttgggtta aatgcgtgt                                                  19

<210> SEQ ID NO 43
<211> LENGTH: 20
<212> TYPE: DNA
<213> ORGANISM: Homo sapiens

<400> SEQUENCE: 43
```

```
agcagtttgg gtaaacattg                                              20

<210> SEQ ID NO 44
<211> LENGTH: 20
<212> TYPE: DNA
<213> ORGANISM: Homo sapiens

<400> SEQUENCE: 44
aaatatgcct tctggaggtg                                              20

<210> SEQ ID NO 45
<211> LENGTH: 20
<212> TYPE: DNA
<213> ORGANISM: Homo sapiens

<400> SEQUENCE: 45
ggaggatcag gggagtttat                                              20

<210> SEQ ID NO 46
<211> LENGTH: 24
<212> TYPE: DNA
<213> ORGANISM: Homo sapiens

<400> SEQUENCE: 46
caaagtaaat gaatgtctac tgcc                                         24

<210> SEQ ID NO 47
<211> LENGTH: 23
<212> TYPE: DNA
<213> ORGANISM: Homo sapiens

<400> SEQUENCE: 47
ccaactctgt agtttcaaag agc                                          23

<210> SEQ ID NO 48
<211> LENGTH: 20
<212> TYPE: DNA
<213> ORGANISM: Homo sapiens

<400> SEQUENCE: 48
tcacagccta cttgcttggt                                              20

<210> SEQ ID NO 49
<211> LENGTH: 25
<212> TYPE: DNA
<213> ORGANISM: Homo sapiens

<400> SEQUENCE: 49
gacagcctca aatgaaatat aacac                                        25

<210> SEQ ID NO 50
<211> LENGTH: 25
<212> TYPE: DNA
<213> ORGANISM: Homo sapiens

<400> SEQUENCE: 50
gctctcagct agggtagttg tttat                                        25

<210> SEQ ID NO 51
<211> LENGTH: 25
<212> TYPE: DNA
<213> ORGANISM: Homo sapiens
<220> FEATURE:
<221> NAME/KEY: modified_base
```

```
<222> LOCATION: (20)
<223> OTHER INFORMATION: a, t, c, g, other or unknown

<400> SEQUENCE: 51 attttttaagg aatgtaaagn acaca                                          25

<210> SEQ ID NO 52
<211> LENGTH: 20
<212> TYPE: DNA
<213> ORGANISM: Homo sapiens

<400> SEQUENCE: 52
gaccaggagt cagtaaaagg                                                 20

<210> SEQ ID NO 53
<211> LENGTH: 20
<212> TYPE: DNA
<213> ORGANISM: Homo sapiens

<400> SEQUENCE: 53
gtccaaaaca ccaccctcta                                                 20

<210> SEQ ID NO 54
<211> LENGTH: 24
<212> TYPE: DNA
<213> ORGANISM: Homo sapiens

<400> SEQUENCE: 54
gaagtagatc agtcatcttg ctgc                                            24

<210> SEQ ID NO 55
<211> LENGTH: 19
<212> TYPE: DNA
<213> ORGANISM: Homo sapiens

<400> SEQUENCE: 55
tcctctgggg gattcactc                                                  19

<210> SEQ ID NO 56
<211> LENGTH: 20
<212> TYPE: DNA
<213> ORGANISM: Homo sapiens

<400> SEQUENCE: 56
gggacatcac caagcacaag                                                 20

<210> SEQ ID NO 57
<211> LENGTH: 25
<212> TYPE: DNA
<213> ORGANISM: Homo sapiens

<400> SEQUENCE: 57
caggaaaata aatctaacac acata                                           25

<210> SEQ ID NO 58
<211> LENGTH: 20
<212> TYPE: DNA
<213> ORGANISM: Homo sapiens

<400> SEQUENCE: 58
cctgtgggca ctgataaata                                                 20

<210> SEQ ID NO 59
```

-continued

```
<211> LENGTH: 19
<212> TYPE: DNA
<213> ORGANISM: Homo sapiens

<400> SEQUENCE: 59
cccagccccc atctcaccg                                                19

<210> SEQ ID NO 60
<211> LENGTH: 19
<212> TYPE: DNA
<213> ORGANISM: Homo sapiens

<400> SEQUENCE: 60
cccagccccc atctcacca                                                19

<210> SEQ ID NO 61
<211> LENGTH: 19
<212> TYPE: DNA
<213> ORGANISM: Homo sapiens

<400> SEQUENCE: 61
ctgcggagga ggctgctgg                                                19

<210> SEQ ID NO 62
<211> LENGTH: 19
<212> TYPE: DNA
<213> ORGANISM: Homo sapiens

<400> SEQUENCE: 62
tcactcccac cacccttt c                                               19

<210> SEQ ID NO 63
<211> LENGTH: 20
<212> TYPE: DNA
<213> ORGANISM: Homo sapiens

<400> SEQUENCE: 63
agaagtttag tgtggcgtgg                                               20

<210> SEQ ID NO 64
<211> LENGTH: 17
<212> TYPE: DNA
<213> ORGANISM: Homo sapiens

<400> SEQUENCE: 64
gccatctccc caagccc                                                  17

<210> SEQ ID NO 65
<211> LENGTH: 18
<212> TYPE: DNA
<213> ORGANISM: Homo sapiens

<400> SEQUENCE: 65
tcgatgcgag ctgaagcg                                                 18

<210> SEQ ID NO 66
<211> LENGTH: 18
<212> TYPE: DNA
<213> ORGANISM: Homo sapiens

<400> SEQUENCE: 66
tcgatgcgag ctgaagca                                                 18
```

<210> SEQ ID NO 67
<211> LENGTH: 20
<212> TYPE: DNA
<213> ORGANISM: Homo sapiens

<400> SEQUENCE: 67
tgaatgttaa agggctctgg                                           20

<210> SEQ ID NO 68
<211> LENGTH: 19
<212> TYPE: DNA
<213> ORGANISM: Homo sapiens

<400> SEQUENCE: 68
ttggttctca gctccggcg                                            19

<210> SEQ ID NO 69
<211> LENGTH: 19
<212> TYPE: DNA
<213> ORGANISM: Homo sapiens

<400> SEQUENCE: 69
ttggttctca gctccggca                                            19

<210> SEQ ID NO 70
<211> LENGTH: 19
<212> TYPE: DNA
<213> ORGANISM: Homo sapiens

<400> SEQUENCE: 70
agaaaccggg ctggctgtg                                            19

<210> SEQ ID NO 71
<211> LENGTH: 21
<212> TYPE: DNA
<213> ORGANISM: Homo sapiens

<400> SEQUENCE: 71
gcattgcctt ttgatctcta c                                         21

<210> SEQ ID NO 72
<211> LENGTH: 18
<212> TYPE: DNA
<213> ORGANISM: Homo sapiens

<400> SEQUENCE: 72
tgggctcttc tgcgggga                                             18

<210> SEQ ID NO 73
<211> LENGTH: 18
<212> TYPE: DNA
<213> ORGANISM: Homo sapiens

<400> SEQUENCE: 73
tgggctcttc tgcgggg                                              18

<210> SEQ ID NO 74
<211> LENGTH: 20
<212> TYPE: DNA
<213> ORGANISM: Homo sapiens

<400> SEQUENCE: 74
tgcctcttct tctgccttcc                                           20

```
<210> SEQ ID NO 75
<211> LENGTH: 22
<212> TYPE: DNA
<213> ORGANISM: Homo sapiens

<400> SEQUENCE: 75
cgagctgtac ctgaggaagc gt                                           22

<210> SEQ ID NO 76
<211> LENGTH: 24
<212> TYPE: DNA
<213> ORGANISM: Homo sapiens

<400> SEQUENCE: 76
cctgagctgt acctgaggaa gcgc                                         24

<210> SEQ ID NO 77
<211> LENGTH: 20
<212> TYPE: DNA
<213> ORGANISM: Homo sapiens

<400> SEQUENCE: 77
catcatgagc ccggggtggc                                              20

<210> SEQ ID NO 78
<211> LENGTH: 23
<212> TYPE: DNA
<213> ORGANISM: Homo sapiens

<400> SEQUENCE: 78
tttctcttgg cttcctggtg cgt                                          23

<210> SEQ ID NO 79
<211> LENGTH: 25
<212> TYPE: DNA
<213> ORGANISM: Homo sapiens

<400> SEQUENCE: 79
accttctctt ggcttcctgg tgcgg                                        25

<210> SEQ ID NO 80
<211> LENGTH: 26
<212> TYPE: DNA
<213> ORGANISM: Homo sapiens

<400> SEQUENCE: 80
gccaaaggtg tcgtgccagg gctcca                                       26

<210> SEQ ID NO 81
<211> LENGTH: 20
<212> TYPE: DNA
<213> ORGANISM: Homo sapiens

<400> SEQUENCE: 81
atctgagaag gccctgctct                                              20

<210> SEQ ID NO 82
<211> LENGTH: 20
<212> TYPE: DNA
<213> ORGANISM: Homo sapiens

<400> SEQUENCE: 82
atctgagaag gccctgctcc                                              20
```

<210> SEQ ID NO 83
<211> LENGTH: 19
<212> TYPE: DNA
<213> ORGANISM: Homo sapiens

<400> SEQUENCE: 83
cccacactta gccttgatg                                                  19

<210> SEQ ID NO 84
<211> LENGTH: 19
<212> TYPE: DNA
<213> ORGANISM: Homo sapiens

<400> SEQUENCE: 84
atgagttagc ccagcggag                                                  19

<210> SEQ ID NO 85
<211> LENGTH: 19
<212> TYPE: DNA
<213> ORGANISM: Homo sapiens

<400> SEQUENCE: 85
attgagagcc cttggagtg                                                  19

<210> SEQ ID NO 86
<211> LENGTH: 19
<212> TYPE: DNA
<213> ORGANISM: Homo sapiens

<400> SEQUENCE: 86
tgatttcgta agacaagtg                                                  19

<210> SEQ ID NO 87
<211> LENGTH: 20
<212> TYPE: DNA
<213> ORGANISM: Homo sapiens

<400> SEQUENCE: 87
agcaaattct aggagttatg                                                 20

<210> SEQ ID NO 88
<211> LENGTH: 19
<212> TYPE: DNA
<213> ORGANISM: Homo sapiens

<400> SEQUENCE: 88
agctgagatg tccggatcg                                                  19

<210> SEQ ID NO 89
<211> LENGTH: 18
<212> TYPE: DNA
<213> ORGANISM: Homo sapiens

<400> SEQUENCE: 89
agctgagatt ccggatca                                                   18

<210> SEQ ID NO 90
<211> LENGTH: 20

```
<212> TYPE: DNA
<213> ORGANISM: Homo sapiens

<400> SEQUENCE: 90
gtcctcttaa cttcccttcc                                              20
```